United States Patent
Thorne et al.

(10) Patent No.: US 12,372,527 B2
(45) Date of Patent: Jul. 29, 2025

(54) SYSTEMS AND COMPOSITIONS FOR DIAGNOSING BARRETT'S ESOPHAGUS AND METHODS OF USING THE SAME

(71) Applicant: CERNOSTICS, INC., Bethlehem, PA (US)

(72) Inventors: Rebecca Jane Thorne, Pittsburgh, PA (US); Bruce B. Campbell, Pittsburgh, PA (US)

(73) Assignee: CERNOSTICS, INC., Bethlehem, PA (US)

( * ) Notice: Subject to any disclaimer, the term of this patent is extended or adjusted under 35 U.S.C. 154(b) by 711 days.

(21) Appl. No.: 17/529,598

(22) Filed: Nov. 18, 2021

(65) Prior Publication Data
US 2022/0291219 A1   Sep. 15, 2022

Related U.S. Application Data

(63) Continuation of application No. 16/002,098, filed on Jun. 7, 2018, now Pat. No. 11,221,333, which is a continuation of application No. 14/005,409, filed as application No. PCT/US2012/029198 on Mar. 15, 2012, now Pat. No. 10,018,631.

(60) Provisional application No. 61/453,929, filed on Mar. 17, 2011.

(51) Int. Cl.
G01N 33/574 (2006.01)
C12Q 1/6886 (2018.01)

(52) U.S. Cl.
CPC ..... *G01N 33/57407* (2013.01); *C12Q 1/6886* (2013.01); *G01N 2800/14* (2013.01); *G01N 2800/56* (2013.01)

(58) Field of Classification Search
CPC .............................................. G01N 33/57407
See application file for complete search history.

(56) References Cited

U.S. PATENT DOCUMENTS

| | | | |
|---|---|---|---|
| 5,989,835 A | 11/1999 | Dunlay et al. | |
| 6,025,128 A | 2/2000 | Veltri et al. | |
| 6,103,479 A | 8/2000 | Taylor | |
| 6,218,122 B1 | 4/2001 | Friend et al. | |
| 6,416,959 B1 | 7/2002 | Giuliano et al. | |
| 6,573,039 B1 | 6/2003 | Dunlay et al. | |
| 6,633,662 B2 | 10/2003 | Ravkin | |
| 6,671,624 B1 | 12/2003 | Dunlay et al. | |
| 6,727,071 B1 | 4/2004 | Dunlay et al. | |
| 6,759,206 B1 | 7/2004 | Rubin et al. | |
| 6,763,307 B2 | 7/2004 | Berg et al. | |
| 6,875,578 B2 | 4/2005 | Giuliano et al. | |
| 6,939,720 B2 | 9/2005 | Chandler et al. | |
| 6,986,993 B1 | 1/2006 | Ghosh et al. | |
| 7,060,445 B1 | 6/2006 | Dunlay et al. | |
| 7,117,098 B1 | 10/2006 | Dunlay et al. | |
| 7,130,746 B2 | 10/2006 | Friend et al. | |
| 7,219,016 B2 | 5/2007 | Rimm et al. | |
| 7,274,809 B2 | 9/2007 | MacAulay et al. | |
| 7,282,347 B2 | 10/2007 | Bjorn et al. | |
| 8,114,615 B2 | 2/2012 | Gough et al. | |
| 8,597,899 B2 | 12/2013 | Gough et al. | |
| 2001/0029019 A1 | 10/2001 | Waldman et al. | |
| 2001/0039015 A1 | 11/2001 | Sauter | |
| 2003/0059093 A1 | 3/2003 | Rosania et al. | |
| 2003/0096243 A1 | 5/2003 | Busa | |
| 2004/0043436 A1 | 3/2004 | Vlahou et al. | |
| 2004/0101912 A1 | 5/2004 | Rubin et al. | |
| 2004/0157242 A1 | 8/2004 | Ivey et al. | |
| 2006/0014238 A1 | 1/2006 | Gholap et al. | |
| 2006/0094868 A1 | 5/2006 | Giuliano et al. | |
| 2006/0188140 A1 | 8/2006 | Gholap et al. | |
| 2006/0199210 A1 | 9/2006 | Weichselbaum et al. | |
| 2007/0019854 A1 | 1/2007 | Gholap et al. | |
| 2007/0099219 A1 | 5/2007 | Teverovskiy et al. | |

(Continued)

FOREIGN PATENT DOCUMENTS

| | | | |
|---|---|---|---|
| WO | 1992017853 A2 | 10/1992 | |
| WO | 1998035609 A1 | 8/1998 | |

(Continued)

OTHER PUBLICATIONS

Abdel-Latif et al., "NF-kB Activation in Esophageal Adenocarcinoma: Relationship to Barrett's Metaplasia, Survival, and Response to Neoadjuvant Chemoradiotherapy," Annals of Surgery, Apr. 2004, vol. 239: No. 4, pp. 491-500.

Aldulaimi et al., "Barrett's Surveillance is Worthwhile and Detects Curable Cancers. A Prospective Cohort Study Addressing Cancer Incidence, Treatment Outcome and Survival," Eur J. Gastroenterol Hepatol., 17(9):943-950 (2005).

Allameh et al., "Immunohistochemical Analysis Of Selected Molecular Markers In Esophagus Precancerous, Adenocarcinoma and Squamous Cell Carcinoma In Iranian Subjects," CancerEpidemiology, 33(1):79-84 (2009).

(Continued)

*Primary Examiner* — Prema M Mertz
(74) *Attorney, Agent, or Firm* — McDonnell Boehnen Hulbert & Berghoff LLP

(57) ABSTRACT

The invention provides a system, composition, and methods of using the systems and compositions for the analysis of a sample from a subject to accurately diagnose, prognose, or classify the subject with certain grades of or susceptibility to Barrett's esophagus. In some embodiments, the system of the present invention comprises a means of detecting and/or quantifying morphological features, the expression of protein, or the expression of nucleic acids in a plurality of cells and correlating that data with a subject's medical history to predict clinical outcome, treatment plans, preventive medicine plans, or effective therapies. In some embodiments, the invention relates to a method of classifying and compiling data taken from a cell sample from a subject analyzing the data, and converting the data from the system into a score by which a pathologist may calculate the likelihood that the subject develops cancer.

9 Claims, 12 Drawing Sheets

(56) References Cited

U.S. PATENT DOCUMENTS

| | | |
|---|---|---|
| 2007/0212721 A1 | 9/2007 | Fischer et al. |
| 2008/0008349 A1 | 1/2008 | Binnig et al. |
| 2008/0015786 A1 | 1/2008 | Ramer et al. |
| 2008/0057514 A1 | 3/2008 | Goldenring |
| 2009/0170091 A1 | 7/2009 | Giuliano et al. |
| 2009/0317836 A1 | 12/2009 | Kuhn et al. |
| 2013/0078632 A1 | 3/2013 | Krishnadath |
| 2014/0162888 A1 | 6/2014 | Kuslich et al. |
| 2018/0348226 A1 | 12/2018 | Thorne |

FOREIGN PATENT DOCUMENTS

| | | |
|---|---|---|
| WO | 2000070528 A2 | 11/2000 |
| WO | 2001033228 A2 | 5/2001 |
| WO | 2001074405 A1 | 10/2001 |
| WO | 2001081895 A2 | 11/2001 |
| WO | 2004076643 A2 | 9/2004 |
| WO | 2004094992 A2 | 11/2004 |
| WO | 2005050556 A2 | 6/2005 |
| WO | 2005050563 A3 | 6/2005 |
| WO | 2005091203 A2 | 9/2005 |
| WO | 2006020627 A1 | 2/2006 |
| WO | 2006036726 A1 | 4/2006 |
| WO | 2006037622 A1 | 4/2006 |
| WO | 2007044944 A1 | 4/2007 |
| WO | 2007045896 A1 | 4/2007 |
| WO | 2007081968 A1 | 7/2007 |
| WO | 2007092547 A2 | 8/2007 |
| WO | 2007130677 A2 | 11/2007 |
| WO | 2007136724 A2 | 11/2007 |
| WO | 2008060483 A2 | 5/2008 |
| WO | 2009105533 A2 | 8/2009 |
| WO | 2010121266 A1 | 10/2010 |
| WO | 2011088226 A2 | 7/2011 |
| WO | 2012125807 A2 | 9/2012 |
| WO | 2017091658 A1 | 6/2017 |

OTHER PUBLICATIONS

Blankenstein et al., "Modular Concept of a Laboratory on a Chip for Chemical and Biochemical Analysis," Biosensors & Bioelectronics, Elsevier Science Publishers, Barking, GB, vol. 13, No. ¾, 1998, pp. 427-438, XP000700154, ISSN: 0956-5663.

Bobryshev et al., "Dendritic Cell-Associated Immune Inflammation of Cardiac Mucosa: A Possible Factor in the Formation of Barrett's Esophagus," J Gastrointest Surg, 2009, 13, pp. 442-450.

Brabender et al., "A Multigene Expression Panel for the Molecular Diagnosis of Barrett's Esophagus and Barrett's Adenacarcinoma of the Esophagus," Oncogene, 2004, vol. 23, pp. 4780-4788.

Buttar et al., "The Effect of Selective Cyclooxygenase-2 Inhibition in Barrett's Esophagus Epithelium: An In Vitro Study," Journal of the National Cancer Institute, vol. 94, No. 6, Mar. 20, 2002.

Cappello et al., "CDla Expression by Barrett's Metaplasia of Gastric Type May Help to Predict Its Evolution Towards Cancer," British Journal of Cancer, 2005, vol. 92, pp. 888-890.

Critchley-Thorne et al., "A Tissue Systems Pathology Assay for High-Risk Barrett's Esophagus," Cancer Epidemiol Biomarkers Prev, 25(6): 1-11 (2016).

Critchley-Thorne et al., "A Tissue Systems Pathology Test Detects Abnormalities Associated with Prevalent High-Grade Dysplasia and Esophageal Cancer in Barrett's Esophagus," Cancer Epidemiol Biomarkers Prev, 26(2): 240-248 (2017).

Davison et al., "Independent Blinded Validation of a Tissue Systems Pathology Test to Predict Progression in Patients With Barrett's Esophagus," The American Journal of Gastroenterology, Feb. 18, 2020, pp. 1-10.

Ell et al., "Endoscopic Mucosal Resection of Early Cancer and High-Grade Dysplasia in Barrett's Esophagus," Gastroenterology, Apr. 2000, 118:670-677.

European Search Report for corresponding European Application No. 12757085.1 dated Mar. 6, 2015.

Frei et al., "Independent Validation of a Tissue Systems Pathology Assay to Predict Future Progression in Nondysplastic Barrett's Esophagus: A Spatial-Temporal Analysis," Clinical and Translational Gastroenterology, Oct. 8, 2020, vol. 11, pp. 1-8.

Frei et al., "Tissue Systems Pathology Test Objectively Risk Stratifies Barrett's Esophagus Patients With Low-Grade Dysplasia," Am. J. Gastroenterol., Nov. 18, 2020, vol. 00, pp. 1-8.

Gail et al., "Projecting Individualized Probabilities of Developing Breast Cancer for White Females Who Are Being Examined Annually," Journal of National Cancer Institute, vol. 81:1879-1886, Dec. 20, 1989.

Gao et al., "p53 Tumor Suppressor Gene Mutation in Early Esophageal Precancerous Lesions and Carcinoma Among High-Risk Populations in Henan, China," Cancer Research, 54:4342-4346 (1994).

Giuliano et al., "Optimal Characteristics of Protein-Protein Interaction Biosensors for Cellular Systems Biology Profiling," Preprint to be published in High Content Screening: Science, Technology and Applications, ed. Haney, S.A., Wiley Publishers, (2007), Retrieved from the Internet: url:http://www.cellumen.com/downloads/cellumen-2007-Giuliano-PPIBs.pdf; [retrieved on Sep. 1, 2008].

Giuliano et al., "Systems Cell Biology Based on High-Content Screening," Methods in Enzymology, Elsevier Academic Press, Inc., pp. 601-619 (2006), XP009097131, ISSN: 0-12-182819-0(H).

Giuliano et al., "Systems Cell Biology Knowledge Created from High Content Screening," Assay and Drug Development Technologies, 3(5):501-514 (Oct. 2005) XP002473054, ISSN: 1540-658X.

Hamilton et al., "Digital Pathology and Image Analysis in Tissue Biomarker Research," Methods 70 (2014) 59-73.

Helden et al., "Representing and Analysing Molecular and Cellular Function Using the Computer," Biological Chemistry vol. 381, No. 9/10, Sep. 2000, pp. 921-935, XP008032491, ISSN: 1431-6730.

Hormi-Carver et al., "Molecular Markers And Genetics In Cancer Development," Surg Oneal Clin N Am, 18 (3):453-467 (2009).

International Preliminary Report on Patentability for PCT/US2007/011865 dated Nov. 18, 2008.

International Preliminary Report on Patentability for PCT/US2007/023678 dated May 22, 2009.

International Preliminary Report on Patentability for PCT/US2012/029198 dated Sep. 17, 2013.

International Search Report and Written Opinion for PCT/US2007/011865 dated Jan. 11, 2008.

International Search Report and Written Opinion for PCT/US2007/023678 dated Aug. 29, 2008.

International Search Report and Written Opinion for PCT/US2012/029198 dated Oct. 29, 2012.

International Search Report and Written Opinion for PCT/US2016/063482 dated Feb. 1, 2017.

Kyrgidis et al., "Research Review: New Molecular Concepts Of Barrett's Esophagus: Clinical Implications And Biomarkers," Journal of Surgical Research, 125(2): 189-212 (2005).

Levenson et al., "Multispectral Imaging and Pathology: Seeing and Doing More," Expert Opinion Med Diagn. 2008 2 (9): 1067-1081.

Ling et al., "HIF-1α mRNA is Not Associated with Histopathological Regression Following Neoadjuvant Chemoradiation in Esophageal Cancer," Anticancer Research, 2006, vol. 26, pp. 4505-4510.

Macdonald et al., "WnU13-Catenin Signaling: Components, Mechanisms, and Diseases" Developmental Cell vol. 17, Issue 1, Jul. 21, 2009, pp. 9-26.

Malpica et al., "Applying Watershed Algorithms to the Segmentation of Clustered Nuclei," Cytometry: The Journal of the Society for Analytical Cytology, U.S. Aug. 1, 1997, pp. 289-297, XP002242990, ISSN: 0196-4763.

Minghetti, "Cyclooxygenase-2 (COX-2) in inflammatory and degenerative brain diseases," J. Neuropathol Exp Neurol. (Sep. 2004); 63(9):901-10.

Mulrane et al., "Expert Reviews: Automated Image Analysis in Histopathology: A Valuable Tool in Medical Diagnostics," Expert Rev. Mol. Diagn., 8(6): 707-725 (2008).

Osterheld et al., "beta-Catenin Expression and Its Association With Prognostic Factors in Adenocarcinoma Developed in Barrett Esophagus," Am J Clin Pathol 2002, 117, pp. 451-456.

(56) References Cited

OTHER PUBLICATIONS

Phillips et al., "Cdx2 as a Marker of Epithelial Intestinal Differentiation in the Esophagus," Am J Surg Pathol, Nov. 2003, vol. 27: No. 11, pp. 1442-1447.

Prasad et al., "Predictors of Progression in Barrett's Esophagus: Current Knowledge and Future Directions," Am J Gastroenterol. Jul. 2010; 105(7): 1490-1502.

Prichard et al., "TissueCyperTM : A Systems Biology Approach to Anatomic Pathology," J Pathol Inform, 1:48, pp. 1-14 (2015).

Qin et al., "Predicting Progression in Barrett's Esophagus: Is the Holy Grail Within Reach?" Am. J. Gastroenterol., Apr. 14, 2020; 115:841-842.

Rauser et al., "High No. of CD45RO+ Tumor Infiltrating Lymphocytes is an Independent Prognostic Factor in Non-Metastasized (Stage I-IIA) Esophageal Adenocarinoma," BMC Cancer 2010, 10, pp. 608-616.

Rossi et al., "HER-2/neu in Barrett Esophagus: A Comparative Study Between Histology, Immunohistochemistry, and Fluorescence In Situ Hybridization," Diagn Mol Pathol, vol. 15: No. 3, Sep. 2006, pp. 125-130.

Sarbia et al., "Distinction Between Intestinal Metaplasia in the Cardia and in Barett's Esophagus: The Role of Histology and Immunohistochemistry," Institute of Pathology; Human Pathology, vol. 35: No. 3, Mar. 2004, pp. 371-376.

Seibel et al., "Tethered Capsule Endoscopy, A Low-Cost and High-Performance Alternative Technology for the Screening of Esophageal Cancer and Barrett's Esophagus," IEEE Transactions on Biomedical Engineering, vol. 55, No. 3, Mar. 2008, pp. 1032-1042.

Shi et al., "p16, Cyclin D1, Ki-67, and AMACR as Markers for Dysplasia in Barrett Esophagus," Appl Immunohistochem Mol Morphol, Oct. 2008;vol. 16: No. 5, pp. 447-452.

Sikkema et al., "Aneuploidy and Overexpression of Ki67 and p53 as Markers for Neoplastic Progression in Barrett's Esophagus: A Case-Control Study," The American Journal of Gastroenterology, Jul. 28, 2009, vol. 104, pp. 2673-2680.

Szczurek et al., "Single Molecule Localization Microscopy of the Distribution of Chromatin Using Hoechst and DAPI Fluorescent Probes," Nucleus, 5:4, 331-340. (Jun. 19, 2014).

Van Dekken et al., "Immunohistochemical Evaluation Of A Panel Of Tumor Cell Markers During Malignant Progression In Barrett Esophagus," Am J Clin Pathol., 130(5):745-753 (2008).

SYSTEMS AND COMPOSITIONS FOR DIAGNOSING BARRETT'S ESOPHAGUS AND METHODS OF USING THE SAME

RELATED APPLICATION

This application claims the benefit of U.S. Provisional Application No. 61/453,929, filed on Mar. 17, 2011.

The entire teachings of the above application are incorporated herein by reference.

FIELD OF THE INVENTION

The invention relates to a system, composition, and series of methods of using the systems and compositions for the analysis of a cell sample from a subject to accurately diagnose, prognose, or classify the subject with certain grades of or susceptibility to Barrett's esophagus (BE) or cancer of the esophagus. In some embodiments, the system of the present invention comprises a means of detecting and/or quantifying morphological features, the expression of protein, or the expression of nucleic acids in a plurality of cells and correlating that data with a subject's medical history to predict clinical outcome, treatment plans, preventive medicine plans, or effective therapies.

BACKGROUND OF THE INVENTION

Barrett's esophagus results from Gastroesophageal Reflux Disease (GERD) and affects approximately 3 million patients in the United States, with 86,000 new cases being diagnosed each year. Aldulaimi et al., Eur J Gastroenterol Hepatol. 2005 September; 17(9):943-50, discloses that a diagnosis of Barrett's esophagus predisposes patients to develop esophageal adenocarcinoma with a risk calculated as 30-125 times more as compared to patients without a diagnosis. Esophageal adenocarcinoma develops in a defined sequence of changes from benign, to low grade dysplasia, to high-grade dysplasia, and to malignant cancer.

Patients with Barrett's esophagus are frequently screened (every 3 months to every 3 years depending on stage of disease) by endoscopy and biopsies are taken for histopathology. Biopsies are analyzed by manual microscopy analysis with traditional Hematoxylin and Eosin-staining of tissue sections. Diagnosis of Barrett's esophagus is based on established histologic criteria and a minimal set of biomarkers measured singly to detect abnormalities.

The screening process has many limitations. For instance, diagnosis of Barrett's esophagus can be characterized in different stages such as low-grade dysplasia, high-grade dysplasia, and reactive atypia. These "stages" of BE share histological features and are difficult to distinguish using current H&E-based analysis. Frequently, the diagnosis results in "indeterminate/indefinite," misdiagnosis, delayed diagnosis or inappropriate treatment. Furthermore, the current form of histology analysis is insufficient to diagnose the various stages of the BE disease accurately and to predict progression to higher disease stages.

There is a need for pathology informatics/descriptive features of BE to integrate biomarker data, morphological data around a tissue sample, and clinical data into decision-making indices. There is also a need for more accurate diagnostic, prognostic and predictive testing to guide clinical management and prevention of malignant forms of gastrointestinal cancer. There is a need for increased surveillance and stratification BE staging and prediction of effective treatments or prevention of malignant cancer. The invention relates to a system, an apparatus, a composition, a device and method of using the same to extract specific biomarker information from cell samples to improve the accuracy of diagnosis, to enable predictions of disease progression and cancer development, to predict responsiveness to therapeutic interventions, and to improve management of BE or any cancer derived from tissue diagnosed as BE.

SUMMARY OF THE INVENTION

In some embodiments, the invention relates to a composition comprising: (a) a cell sample; (b) a plurality of probes and/or stains that bind to biomarkers of the cell sample; (c) one or more optical scanners that generates digital imaging data about the presence, absence, location, quantity, and/or intensity of at least one probe or stain that binds a biomarker of the cell sample; (d) one or more data processors that, either individually or collectively: (i) receives the digital image data from the optical scanner and, optionally, transmutes said digital imaging data into a digital imaging signal; and (ii) analyzes the digital image data to identify, measure, or quantify one or more descriptive features from the plurality of probes and/or stains; and (iii) converts the one or more descriptive features into a score, wherein (iii) optionally comprises integrating stored data about a subject or group of subjects to convert the one or more descriptive features into a score; (e) one or more monitors that comprises a screen and that receives a component of the digital images, or, optionally, receives the digital imaging signal from the data processor and projects a digitally addressable image onto its screen; and (f) one or more data storage units; wherein the one or more optical scanners, the one or more data processors, the one or more monitors, and the one or more data storage units are in digital communication with each other by a means to transmit digital data.

In some embodiments, the invention relates to a system or apparatus comprising: (a) a cell sample; (b) a plurality of probes and/or stains that bind to biomarkers of the cell sample; (c) one or more optical scanners that generates digital imaging data about the presence, absence, location, quantity, and/or intensity of at least one probe or stain that binds a biomarker of the cell sample; (d) one or more data processors, each in operable communication with at least one optical scanner, that, either individually or collectively: (i) receives the digital image data from the optical scanner and, optionally, transmutes said digital imaging data into a digital imaging signal; and (ii) analyzes the digital image data to identify, measure, or quantify one or more descriptive features from the plurality of probes and/or stains; and (iii) converts the one or more descriptive features into a score, wherein (iii) optionally comprises integrating stored data about a subject or group of subjects to convert the one or more descriptive features into a score; (e) one or more monitors, each in operable communication with at least one data processor, that comprises a screen and that receives a component of the digital images, or, optionally, receives the digital imaging signal from the data processor and projects a digitally addressable image onto its screen; and (f) one or more data storage units, each in operable communication with at least one processor.

In some embodiments, the invention relates to a system or apparatus comprising: one or more data processors, each in operable communication with at least one optical scanner, that, either individually or collectively: (i) receives the digital image data from the optical scanner and, optionally, transmutes said digital imaging data into a digital imaging signal; and (ii) analyzes the digital image data to identify, measure, or quantify one or more descriptive features from the plurality of probes and/or stains; and (iii) converts the one or more descriptive features into a score, wherein (iii) optionally comprises integrating stored data about a subject or group of subjects to convert the one or more descriptive features into the score or scores.

In some embodiments, the invention relates to a system or apparatus comprising: one or more data processors, each in operable communication with at least one optical scanner, that, either individually or collectively: (i) analyzes the digital image data to identify, measure, or quantify one or more descriptive features from the plurality of probes and/or stains; and (ii) converts the one or more descriptive features into a score, wherein (ii) optionally comprises integrating stored data about a subject or group of subjects to convert the one or more descriptive features into the score or scores.

In some embodiments, the invention relates to a system comprising: (a) a cell sample; (b) a plurality of probes and/or stains that bind to biomarkers of the cell sample; (c) one or more optical scanners that generates digital imaging data about the presence, absence, location, quantity, and/or intensity of at least one probe or stain that binds a biomarker of the cell sample; (d) one or more data processors that, either individually or collectively: (i) receives the digital image data from the optical scanner and, optionally, transmutes said digital imaging data into a digital imaging signal; and (ii) analyzes the digital image data to identify, measure, or quantify one or more descriptive features from the plurality of probes and/or stains; and (iii) converts the one or more descriptive features into a score, wherein (iii) optionally comprises integrating stored data about a subject or group of subjects to convert the one or more descriptive features into a score; (e) one or more monitors that comprises a screen and that receives a component of the digital images, or, optionally, receives the digital imaging signal from the data processor and projects a digitally addressable image onto its screen; and (f) one or more data storage units; wherein the one or more optical scanners, the one or more data processors, the one or more monitors, and the one or more data storage units are in digital communication with each other by a means to transmit digital data.

In some embodiments, the invention relates to a system comprising: (a) a cell sample; (b) a plurality of probes and/or stains that bind to biomarkers of the cell sample; (c) one or more optical scanners that generates digital imaging data about the presence, absence, location, quantity, and/or intensity of at least one probe or stain that binds a biomarker of the cell sample; (d) one or more data processors that, either individually or collectively: (i) receives the digital image data from the optical scanner and, optionally, transmutes said digital imaging data into a digital imaging signal; and (ii) analyzes the digital image data to identify, measure, or quantify one or more descriptive features from the plurality of probes and/or stains; and (iii) converts the one or more descriptive features into a score, wherein (iii) optionally comprises integrating stored data about a subject or group of subjects to convert the one or more descriptive features into a score; (e) one or more monitors that comprises a screen and that receives a component of the digital images, or, optionally, receives the digital imaging signal from the data processor and projects a digitally addressable image onto its screen; and (f) one or more data storage units; wherein the one or more optical scanners, the one or more data processors, the one or more monitors, and the one or more data storage units are in digital communication with each other by a means to transmit digital data; and wherein the cell sample is taken from a subject identified as having or suspected of having Barrett's esophagus or esophageal cancer. In some embodiments, the cell sample comprises a tissue from a brushing, biopsy, or surgical resection of a subject.

In some embodiments, the descriptive features are at least one or a combination of features chosen from: the presence or absence of one or more biomarkers, the localization of a biomarker within the cell sample, the spatial relationship between the location of biomarker and its position in or among the cell sample or subcellular compartments within a cell sample, the quantity and/or intensity of fluorescence of a bound probe, the quantity and/or intensity of a stain in a cell sample, the presence or absence of morphological features of cells within the plurality of cells, the size or location of morphological features of cells within the plurality of cells, the copy number of a probe bound to a biomarker of at least one cell from the plurality of cells.

In some embodiments, the cell sample comprises a plurality of cells and/or biomaterials. In some embodiments, the cell sample comprises esophageal cells. In some embodiments, the system comprises a cell sample from a subject suspected of or was previously diagnosed with having a disorder of the gastrointestinal tract. In some embodiments, the cell sample is room temperature or frozen. In some embodiments, the cell sample is freshly obtained, formalin fixed, alcohol-fixed and/or paraffin embedded.

In some embodiments, the composition or system comprises an optical scanner, wherein the optical scanner utilizes bright field and/or fluorescence microscopy. In some embodiments, the system measures the localization, position, absence, presence, quantity, intensity or copy number of more than one biomarker. In some embodiments, the composition or system comprises an optical scanner and cell sample, wherein the system simultaneously measures the localization, position, absence, presence, quantity, intensity or copy number of one or more probes or stains bound or intercalated to a cell and/or biomaterial.

In some embodiments, the invention relates to a composition or a system comprising: (a) a cell sample; (b) a plurality of probes and/or stains that bind or intercalate to biomarkers of the cell sample; (c) one or more optical scanners that generates digital imaging data about the presence, absence, location, quantity, and/or intensity of at least one probe or stain that binds a biomarker of the cell sample; (d) one or more data processors that, either individually or collectively: (i) receives the digital image data from the optical scanner and, optionally, transmutes said digital imaging data into a digital imaging signal; and (ii) analyzes the digital image data to identify, measure, or quantify one or more descriptive features from the plurality of probes and/or stains; and (iii) converts the one or more descriptive features into a score, wherein (iii) optionally comprises integrating stored data about a subject or group of subjects to convert the one or more descriptive features into a score; (e) one or more monitors that comprises a screen and that receives a component of the digital images, or, optionally, receives the digital imaging signal from the data processor and projects a digitally addressable image onto its screen; and (f) one or more data storage units; wherein the one or more optical scanners, the one or more data processors, the one or more monitors, and the one or more data storage units are in digital communication with each other by a means to transmit digital data; wherein the data storage units comprise stored data that comprises clinical history of a subject or group of subjects. In some embodiments, the subject or group of subject is suspected of having or has been diagnosed with a gastrointestinal tract disorder. In some embodiments, the subject or group of subjects is suspected of having or has been diagnosed with Barrett's esophagus. In some embodiments, the subject or group of subjects is suspected of having or has been diagnosed with Barrett's esophagus, Barrett's esophagus with high-grade dysplasia, Barrett's esophagus with low-grade dysplasia, Barrett's esophagus with reactive atypia, Barrett's esophagus indefinite for dysplasia or indeterminate Barrett's esophagus. In some embodiments, the subject or group of subjects has been misdiagnosed with a stage of Barrett's esophagus.

In some embodiments, the composition or system comprises one or more data storage units, wherein the one or more data storage units is in digital communication with the one or more optical scanners, one or more monitors, one or more data processors from a remote location.

In some embodiments, the composition or system comprises a microscope. In some embodiments, the plurality of probes comprises at least two probes that comprise a fluorescent tag.

In some embodiments, the invention relates to a composition or system comprising: (a) a cell sample; (b) a plurality of probes and/or stains that bind or intercalate to biomarkers of the cell sample; (c) one or more optical scanners that generates digital imaging data about the presence, absence, location, quantity, and/or intensity of at least one probe or stain that binds a biomarker of the cell sample; (d) one or more data processors that, either individually or collectively: (i) receives the digital image data from the optical scanner and, optionally, transmutes said digital imaging data into a digital imaging signal; and (ii) analyzes the digital image data to identify, measure, or quantify one or more descriptive features from the plurality of probes and/or stains; and (iii) converts the one or more descriptive features into a score, wherein (iii) optionally comprises integrating stored data about a subject or group of subjects to convert the one or more descriptive features into a score; (e) one or more monitors that comprises a screen and that receives a component of the digital images, or, optionally, receives the digital imaging signal from the data processor and projects a digitally addressable image onto its screen; and (f) one or more data storage units; wherein the one or more optical scanners, the one or more data processors, the one or more monitors, and the one or more data storage units are in digital communication with each other by a means to transmit digital data; wherein the system identifies the location, position, absence, presence, quantity or intensity of fluorescence of at least two fluorescent probes simultaneously. In some embodiments the biomarkers are chosen from a combination of two or more of the following proteins: p16, p53, Ki-67, beta-catenin, alpha-methylacyl-CoA racemase (AMACR, P504S), matrix metalloproteinase 1, CD1a, NF-kappa-B p65 (NF-κB), cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha.

In some embodiments, the composition or system comprises a cell sample with one or more different cell types. In some embodiments, the cell sample comprises a combination of any two or more of the following cell types: epithelial cells, multilayered-epithelial cells, endothelial cells, peripheral mononuclear lymphocytes, T cells, B cells, natural killer cells, eosinophils, mast cells, macrophages, dendritic cells, neutrophils, fibroblasts, goblet cells, dysplastic cells, and non-goblet columnar epithelial cells.

In some embodiments the plurality of probes and/or stains comprises at least one stain that binds nucleic acid. In some embodiments, the plurality of probes comprise at least one or a combination of probes that identify the presence or absence of 9p21, 8q24.12-13, 17q11.2-q12, or centromeres.

In some embodiments, the composition or system creates an image with high resolution or a three-dimensional image.

In some embodiments, the invention relates to a method of quantifying one or more biomarkers in a cell sample comprising: providing a cell sample, contacting a plurality of probes and/or stains with cell sample either serially or simultaneously, and determining relative quantity of probes bound to a plurality of biomarkers using a composition or system comprising: (a) a cell sample; (b) a plurality of probes and/or stains that bind or intercalate to biomarkers of the cell sample; (c) one or more optical scanners that generates digital imaging data about the presence, absence, location, quantity, and/or intensity of at least one probe or stain that binds a biomarker of the cell sample; (d) one or more data processors that, either individually or collectively: (i) receives the digital image data from the optical scanner and, optionally, transmutes said digital imaging data into a digital imaging signal; and (ii) analyzes the digital image data to identify, measure, or quantify one or more descriptive features from the plurality of probes and/or stains; and (iii) converts the one or more descriptive features into a score, wherein (iii) optionally comprises integrating stored data about a subject or group of subjects to convert the one or more descriptive features into a score; (e) one or more monitors that comprises a screen and that receives a component of the digital images, or, optionally, receives the digital imaging signal from the data processor and projects a digitally addressable image onto its screen; and (f) one or more data storage units; wherein the one or more optical scanners, the one or more data processors, the one or more monitors, and the one or more data storage units are in digital communication with each other by a means to transmit digital data.

In some embodiments, the method comprises biomarkers derived from a single cell. In some embodiments, the method comprises biomarkers derived from two or more cells. In some embodiments, the method comprises a cell sample or tissue sample prepared from a biopsy of a subject. In some embodiments, the method comprises a cell sample prepared from a punch biopsy of a subject. In some embodiments, the method comprises a cell sample prepared from a biopsy of a subject diagnosed with Barrett's esophagus or suspected of having Barrett's esophagus. In some embodiments, the method comprises the cell sample is from a subject or group of subjects diagnosed with or suspected of having Barrett's esophagus, Barrett's esophagus with high grade dysplasia, Barrett's esophagus with reactive atypia, or indeterminate Barrett's esophagus. In some embodiments, the method comprises the cell sample is from a subject or group of subjects that has been misdiagnosed with a stage of Barrett's esophagus.

In some embodiments, the method comprises a plurality of probes comprising at least two probes that each comprises a fluorescent tag. In some embodiments, the method comprises a system that measures the quantity or intensity of at least two probes measures fluorescence of at least two fluorescent tags simultaneously. In some embodiments, the biomarkers are chosen from a combination of two or more of the following proteins: p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha. In some embodiments, the method comprises a cell sample comprising a combination of any two or more of the following cell types: epithelial cells, multilayered-epithelial cells, endothelial cells, peripheral mononuclear lymphocytes, T cells, B cells, natural killer cells, eosinophils, mast cells, macrophages, dendritic cells, neutrophils, fibroblasts, goblet cells, dysplastic cells, and non-goblet columnar epithelial cells. In some embodiments, the method comprises a plurality of probes and/or stains comprising at least one stain that binds nucleic acid. In some embodiments, the method comprises a plurality of probes comprising at least one or a combination of probes that identify the presence or absence of 9p21, 8q24.12-13, 17q11.2-q12, or centromeres. In some embodiments, the method uses a system that creates an image with high resolution or a three-dimensional image. In some embodiments, the quantified biomarkers are of at least partly known nucleic acid sequence, and the plurality of probes comprises a probe set for each nucleic acid to be quantified, the probe set comprising a plurality of probes perfectly complementary to a nucleic acid sequence. In some embodiments, the method comprises a plurality of probes comprising a probe set for between 1 and about 20 biomarkers. In some embodiments, the method comprises a plurality of probes comprising a probe set for between 1 and about 15 biomarkers. In some embodiments, the method comprises a plurality of probes comprising a probe set for between 1 and about 10 biomarkers.

In some embodiments, the method further comprises comparing the ratio of bound probes to determine the relative expression levels of the biomarkers.

In some embodiments, the invention relates to a method of quantifying one or more biomarkers in a cell sample comprising: providing a cell sample, contacting a plurality of probes and/or stains with cell sample either serially or simultaneously, and determining relative quantity of probes bound to a plurality of biomarkers using a composition or system comprising: (a) a cell sample; (b) a plurality of probes and/or stains that bind or intercalate to biomarkers of the cell sample; (c) one or more optical scanners that generates digital imaging data about the presence, absence, location, quantity, and/or intensity of at least one probe or stain that binds a biomarker of the cell sample; (d) one or more data processors that, either individually or collectively: (i) receives the digital image data from the optical scanner and, optionally, transmutes said digital imaging data into a digital imaging signal; and (ii) analyzes the digital image data to identify, measure, or quantify one or more descriptive features from the plurality of probes and/or stains; and (iii) converts the one or more descriptive features into a score, wherein (iii) optionally comprises integrating stored data about a subject or group of subjects to convert the one or more descriptive features into a score; (e) one or more monitors that comprises a screen and that receives a component of the digital images, or, optionally, receives the digital imaging signal from the data processor and projects a digitally addressable image onto its screen; and (f) one or more data storage units; wherein the one or more optical scanners, the one or more data processors, the one or more monitors, and the one or more data storage units are in digital communication with each other by a means to transmit digital data; and wherein the relative expression levels of 5 or more biomarkers are determined simultaneously. In some embodiments, the relative expression levels of 10 or more biomarkers are determined simultaneously. In some embodiments, the relative expression levels of 15 or more biomarkers are determined simultaneously.

In some embodiments, the invention relates to a method of diagnosing Barrett's esophagus comprising: (a) providing a cell sample of tissue; (b) contacting a plurality of probes and/or stains with the cell sample; (c) identifying one or more descriptive features; (d) determining one or more scores based upon the presence, absence, or quantity of descriptive features; and (e) correlating the score to a subclass of Barrett's esophagus. In some embodiments, the method further comprises identifying a subject suspected of or having been previously diagnosed with a gastrointestinal tract disorder, wherein the cell sample is taken from the subject suspected of or having been previously diagnosed with a gastrointestinal tract disorder. In another embodiment, the method of diagnosing Barrett's esophagus comprises using any one of the aforementioned systems or compositions. In some embodiments, the descriptive features comprise one or a combination of more than one of morphological features chosen from: the presence of goblet cells; the presence of cytological and architectural abnormalities; the presence of cell stratification; the presence of multilayered epithelium; the maturation of the surface epithelium; the degree of budding, irregularity, branching, and atrophy in crypts; the proportion of low grade crypts to high grade crypts; the presence of splaying and duplication of the muscularis mucosa; the presence, number and size of thin-walled blood vessels, lymphatic vessels, and nerve fibers; the frequency of mitoses; the presence of atypical mitoses; the size and chromicity of nuclei; the presence of nuclear stratification; the presence of pleomorphism; the nucleus: cytoplasm volume ratio; the presence of villiform change; the presence of the squamocolumnar junction (Z-line) and its location in relation to the gastroesophageal junction; the presence of ultra-short segment Barrett's esophagus; the intestinal differentiation in nongoblet columnar epithelial cells; the presence of longated, crowded, hyperchromatic, mucin-depleted epithelial cells; the degree of loss of cell polarity; the penetration of cells through the original muscularis mucosa; the infiltration of dysplastic cells beyond the basement membrane into the lamina propria. In some embodiments, the descriptive features are determined by measuring the presence, absence, quantity, or copy number of probes and/or stains bound to or intercalated with biomarkers derived from a single cell type.

In some embodiments, the biomarkers are expressed in two or more cells. In some embodiments, the probes and/or stains used in the method comprise a plurality of probes with one or more fluorescent tag. In some embodiments, the probes and/or stains used in the method comprise a plurality of stains that fluoresce when exposed to natural, visible, or UV light.

The invention also relates to a method of diagnosing Barrett's esophagus comprising: (a) providing a cell sample of tissue; (b) contacting a plurality of probes and/or stains with the cell sample; (c) identifying one or more descriptive features; (d) determining one or more scores based upon the presence, absence, or quantity of descriptive features; and (e) correlating the score to a subclass of Barrett's esophagus; wherein the cell sample comprises a tissue from a brushing, punch biopsy, or surgical resection of a subject. In some embodiments, the method further comprises identifying a subject suspected of or having been previously diagnosed with a gastrointestinal tract disorder, wherein the cell sample is taken from the subject suspected of or having been previously diagnosed with a gastrointestinal tract disorder.

In some embodiments, the method further comprises identifying a subject who is at risk of developing dysplasia, tumor growth, or malignant cancer in the gastrointestinal tract, wherein the cell sample is taken from the subject who has been identified as a subject at risk of developing dysplasia, tumor growth, or malignant cancer in the gastrointestinal tract.

In some embodiments, the method comprises the use of any aforementioned composition or system comprising an optical scanner, wherein the optical scanner that measures the quantity or intensity of at least two probes measures fluorescence of at least two fluorescent tags simultaneously.

In some embodiments, the method comprises the use of any aforementioned composition or system comprising the detection of biomarkers expressed by cells in the cell sample, wherein the biomarkers are chosen from a combination of two or more of the following proteins: p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha. In some embodiments, the method comprises analyzing a cell sample comprising a plurality of cells, wherein the plurality of cells comprise a combination of any two or more of the following cell types: epithelial cells, multilayered-epithelial cells, endothelial cells, peripheral mononuclear lymphocytes, T cells, B cells, natural killer cells, eosinophils, mast cells, macrophages, dendritic cells, neutrophils, fibroblasts, goblet cells, dysplastic cells, and non-goblet columnar epithelial cells. In some embodiments, the probes and/or stains comprise at least one stain that binds nucleic acid. In some embodiments, the probes and/or stains comprise at least one probe that binds nucleic acid. In some embodiments, the probes and/or stains comprise at least one stain that intercalates to nucleic acid. In some embodiments, the method comprises a plurality of probes and/or stains, wherein the plurality of probes and/or stains comprise at least one or a combination of probes or stains that identify the presence or absence of 9p21, 8q24.12-13, 17q11.2-q12, or centromeres.

The invention also relates to a method of diagnosing Barrett's esophagus comprising: (a) providing a cell sample of tissue; (b) contacting a plurality of probes and/or stains with the cell sample; (c) identifying one or more descriptive features; (d) determining one or more scores based upon the presence, absence, or quantity of descriptive features; and (e) correlating the score to a subclass of Barrett's esophagus; wherein the method comprises one of the aforementioned system or composition to identify one or more descriptive features, wherein the system or composition generates an image with high resolution or a three-dimensional image. In some embodiments, the one or more descriptive features comprise quantification of a partly known nucleic acid sequence, and the wherein said quantification is determined by quantifying a probe set comprising a plurality of probes perfectly complementary or partially complementary to a nucleic acid sequence. In some embodiments, the method comprises a plurality of probes and/or stains that comprise a probe set for between 1 and about 20 biomarkers. In some embodiments, the method comprises the plurality of probes and/or stains that comprise a probe set for between 1 and about 15 biomarkers. In some embodiments, the method comprises the plurality of probes and/or stains that comprise a probe set for between 1 and about 10 biomarkers. In some embodiments, the method comprises the plurality of probes and/or stains that comprise a probe set for between 1 and about 5 biomarkers. In some embodiments, the method comprises the plurality of probes and/or stains that comprise a probe set for between 1 and about 4 biomarkers. In some embodiments, the method comprises the plurality of probes and/or stains that comprise a probe set for between 1 and about 3 biomarkers.

The invention also relates to a method of diagnosing Barrett's esophagus comprising: (a) providing a cell sample of tissue; (b) contacting a plurality of probes and/or stains with the cell sample; (c) identifying one or more descriptive features; (d) determining one or more scores based upon the presence, absence, or quantity of descriptive features; and (e) correlating the score to a subclass of Barrett's esophagus; wherein the method comprises use of one of the aforementioned system or composition to complete any one or more steps (a), (b), (c), (d), and (e).

The invention also relates to a method of diagnosing Barrett's esophagus comprising: (a) providing a cell sample of tissue; (b) contacting a plurality of probes and/or stains with the cell sample; (c) identifying one or more descriptive features; (d) determining one or more scores based upon the presence, absence, or quantity of descriptive features; and (e) correlating the score to a subclass of Barrett's esophagus; wherein the method comprises one of the aforementioned system or composition to identify one or more descriptive features, wherein identifying one or more descriptive features comprises comparing the ratio of the specific binding of probe and/or stain to a biomarker to the non-specific binding of probes and/or stains in order to determine the relative expression levels of the biomarkers. The invention also relates to a method of diagnosing Barrett's esophagus comprising: (a) providing a cell sample of tissue; (b) contacting a plurality of probes and/or stains with the cell sample; (c) identifying one or more descriptive features; (d) determining one or more scores based upon the presence, absence, or quantity of descriptive features; and (e) correlating the score to a subclass of Barrett's esophagus; wherein the method comprises one of the aforementioned system or composition to identify one or more descriptive features, wherein identifying one or more descriptive features comprises comparing the ratio of bound to unbound probes and/or stains to determine the relative expression levels of the biomarkers. In some embodiments, the identifying one or more descriptive features comprises analyzing the relative expression levels of 2 or more biomarkers simultaneously. In some embodiments, the identifying one or more descriptive features comprises analyzing the relative expression levels of 3 or more biomarkers simultaneously. In some embodiments, the identifying one or more descriptive features comprises analyzing the relative expression levels of 4 or more biomarkers simultaneously. In some embodiments, the identifying one or more descriptive features comprises analyzing the relative expression levels of 5 or more biomarkers simultaneously. In some embodiments, the identifying one or more descriptive features comprises analyzing the relative expression levels of 8 or more biomarkers simultaneously. In some embodiments, the identifying one or more descriptive features comprises analyzing the relative expression levels of 10 or more biomarkers simultaneously. In some embodiments, the identifying one or more descriptive features comprises analyzing the relative expression levels of 12 or more biomarkers simultaneously. In some embodiments, the identifying one or more descriptive features comprises analyzing the relative expression levels of 15 or more biomarkers simultaneously. In some embodiments, the identifying one or more descriptive features comprises analyzing the relative expression levels of 20 or more biomarkers simultaneously.

In some embodiments, the invention relates to a method of prognosing a clinical outcome of a subject comprising: (a) providing a cell sample; (b) contacting a plurality of probes and/or stains with the cell sample; (c) identifying one or more descriptive features; (d) determining one or more scores based upon the presence, absence, or quantity of descriptive features; and (e) correlating the score to a subclass of Barrett's esophagus or a certain clinical outcome.

In some embodiments, the invention relates to a method of prognosing a clinical outcome of a subject comprising: (a) providing a cell sample; (b) contacting a plurality of probes and/or stains with the cell sample; (c) identifying one or more descriptive features; (d) determining one or more scores based upon the presence, absence, or quantity of descriptive features; and (e) correlating the score to a subclass of Barrett's esophagus or a certain clinical outcome; wherein the method comprises use of one of the aforementioned systems or compositions to complete any one or more steps (a), (b), (c), (d), and (e).

The invention also relates to a method of determining patient responsiveness to a therapy for one or a combination of gastrointestinal tract disorders comprising: (a) providing a cell sample; (b) contacting a plurality of probes and/or stains with the cell sample; (c) identifying one or more descriptive features; (d) determining one or more scores based upon the presence, absence, and/or quantity of descriptive features; and (e) predicting patient responsiveness to a therapy to treat or prevent a gastrointestinal disorder based upon the score.

The invention also relates to a method of compiling a cellular systems biological profile comprising: (a) providing one or more cell samples from a set of subjects; (b) contacting a plurality of probes and/or stains with the one or more cell samples; (c) identifying one or more descriptive features for each cell sample; (d) determining one or more scores for each cell sample based upon the presence, absence, or quantity of descriptive features; and (e) compiling the scores of each subject; and, optionally, (f) stratifying each subject according to the one or more scores. In some embodiments, the subject or subjects are identified as being susceptible to or at risk for developing, or having been previously diagnosed with one or more gastrointestinal tract disorders.

In some embodiments, the invention relates to a method of compiling a cellular systems biological profile comprising: (a) providing one or more cell samples from a set of subjects; (b) contacting a plurality of probes and/or stains with the one or more cell samples; (c) identifying one or more descriptive features for each cell sample; (d) determining one or more scores for each cell sample based upon the presence, absence, or quantity of descriptive features; (e) compiling the scores of each subject; and, optionally, (f) stratifying each subject according to the one or more scores, further comprising correlating the scores of each subject with a diagnosis of one or more gastrointestinal disorders, a prognosis of a gastrointestinal disorder, or a responsiveness to therapy to treat or prevent one or more gastrointestinal disorders. In some embodiments, the gastrointestinal disorder is Barrett's esophagus or a subclass thereof.

In some embodiments, the invention relates to a method of monitoring gene or protein expression in a subject comprising: contacting a plurality of probes and/or stains with a first and second cell sample of a subject; determining the relative binding or intercalating of the plurality of probes and/or stains to biomarkers from the first and second cell samples; and comparing the presence, absence, or quantity of biomarkers from the first sample to the presence, absence, or quantity of biomarkers from the second cell sample.

In some embodiments, the invention relates to a method of classifying gastrointestinal tract cell samples, comprising: determining a biomarker expression profile of each of a plurality of cell samples; and classifying the cell samples in clusters determined by similarity of biomarker expression profile. In some embodiments, the method of classifying gastrointestinal tract cell samples further comprises use of any one of the compositions or systems described herein.

The invention also relates to a method of monitoring differentiation, morphology, or progression of tumor growth, or the progression of tumor malignancy in a subject comprising: providing two or more cell samples from said subject; determining an expression profile of each of the cell samples; classifying the cell samples into clusters determined by similarity of biomarker expression profile; ordering the clusters by similarity of biomarker expression profile; and determining a time course of biomarker expression levels for each of the plurality of biomarkers at different stages of differentiation, morphology, or tumor growth progression in the cell samples.

The invention also relates to a method for identifying differentially expressed biomarkers, comprising: determining a biomarker expression profile of each of a set of cell samples at different time points; classifying the profile in clusters determined by similarity of biomarker expression; ordering the clusters by similarity of biomarker expression; determining a time course of biomarker levels for each of the plurality of biomarkers at different time points; and identifying differentially expressed biomarkers as between cell samples in the same and different clusters. In some embodiments, the method comprises identifying differentially expressed biomarkers further comprises use of any one of the compositions or systems described herein.

The invention also relates to a method of identifying a specific cell type within a cell sample that contains a plurality of cells comprising: determining a biomarker expression profile of a plurality of cells; classifying the plurality of cells in clusters determined by similarity of biomarker expression profile; and determining the nature and function of the plurality of cells.

In some embodiments, the invention relates to a method of determining, testing, calculating, or assessing a risk of progression of Barrett's esophagus in a subject comprising: a) detecting a subset of biomarkers in a sample from the subject, wherein two or more biomarkers in said subset are selected from the group consisting p53, HIF-1alpha, beta-catenin, and COX-2; and b) determining at least one or more descriptive features listed in Table 4 or 5 associated with said biomarkers, wherein the presence, absence, location, ratio, or quantity of descriptive features determines a score, relative to a control, wherein the score correlates to the risk of progression of Barrett's esophagus in the subject.

In another embodiment, the method of determining, testing, calculating, or assessing a risk of progression of Barrett's esophagus in a subject comprises: a) analyzing, locating, identifying, or quantifying a subset of biomarkers in a sample from the subject, wherein two or more biomarkers in said subset are selected from the group consisting p53, HIF-1alpha, beta-catenin, and COX-2; and b) determining at least one or more descriptive features listed in Table 4 or 5 associated with said biomarkers, wherein the presence, absence, location, ratio, or quantity of descriptive features determines a score, relative to a control, wherein the score correlates to the risk of progression of Barrett's esophagus in the subject.

In another embodiment, the sample comprises a brushing, biopsy, or surgical resection of cells and/or tissue from the subject.

In another embodiment, the descriptive features are identified, located, analyzed, determined, or detected in subcellular and/or tissue compartments.

In another embodiment, at least one or more biomarkers detected are selected from the group consisting of p16, Ki-67, alpha-methylacyl-CoA racemase (AMACR, P504S), matrix metalloproteinase 1, CD1a, NF-kappa-B, CD68, CD4, forkhead box P3, CD45RO, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, and FasL.

In another embodiment, the method further detects at least one or more biomarkers selected from the group consisting of AMACR, CD1a, CD45RO, CD68, CK-20, Ki-67, NF-κB, and p16.

In another embodiment, the subject has an increased risk of progression to low grade dysplasia, high grade dysplasia or esophageal cancer.

In another embodiment, the subject is diagnosed with no dysplasia, reactive atypia, indefinite for dysplasia, low grade dysplasia, or high grade dysplasia.

In another embodiment, the sample is at room temperature or frozen. In another embodiment, the sample is freshly obtained, formalin fixed, alcohol fixed, or paraffin embedded.

In another embodiment, the method further comprises detecting the subset of biomarkers using probes that specifically bind to each of said biomarkers. In another embodiment, at least 10, at least 20, at least 30, at least 40, at least 50, or 60 descriptive features from Tables 4. In another embodiment, at least 10, at least 20, at least 30, at least 40, at least 50, at least 60, at least 70, at least 80, or 89 descriptive features from Table 5.

In another embodiment, the sample comprises a brushing, biopsy, or surgical resection of cells and/or tissue from the subject.

In another embodiment, the descriptive features are identified, located, analyzed, determined, or detected in subcellular and/or tissue compartments.

In another embodiment, the descriptive features further comprise one or more morphometric markers selected from the group consisting of nuclear area, nuclear equivalent diameter, nuclear solidity, nuclear eccentricity, gland to stroma ratio, nuclear area to cytoplasmic area ratio, glandular nuclear size, glandular nuclear size and intensity gradient, and nuclear texture.

In another embodiment, the sample is at room temperature or frozen. In yet another embodiment, the sample is freshly obtained, formalin fixed, alcohol fixed, or paraffin embedded.

In another embodiment, the probes are fluorescent and/or comprise a fluorescent tag, preferably wherein each probe is labeled with a different fluorophore.

In another embodiment, the subset of biomarkers comprises at least 3 biomarkers and wherein the 3 biomarkers are an epithelial biomarker, immune biomarker and/or a stromal biomarker. In yet another embodiment, the method further detects a stem cell biomarker. In another embodiment, the method detects 2 or more, 3 or more, 4 or more, 5 or more, 8 or more, or 12 or more biomarkers are determined simultaneously. In yet another embodiment, the subject is a human.

In one embodiment, the invention relates to a method of classifying Barrett's esophagus in a subject, comprising: a) detecting a subset of biomarkers in a sample from the subject, wherein two or more biomarkers are selected from the group consisting of HIF-1alpha, p53, CD45RO, p16, AMACR, CK-20, CDX-2, HER2/neu, CD1a, COX-2, NF-κB, and a nucleic acid biomarker; and b) determining at least one or more descriptive features listed in Table 6 associated with said biomarkers, wherein the presence, absence, location, ratio, or quantity of descriptive features determines a score, relative to a control, wherein the score correlates to the classification of Barrett's esophagus.

In one embodiment, the invention relates to a method of classifying Barrett's esophagus in a subject, comprising: a) analyzing, locating, identifying, or quantifying a subset of biomarkers in a sample from the subject, wherein two or more biomarkers are selected from the group consisting of HIF-1alpha, p53, CD45RO, p16, AMACR, CK-20, CDX-2, HER2/neu, CD1a, COX-2, NF-κB, and a nucleic acid biomarker; and b) determining at least one or more descriptive features listed in Table 6 associated with said biomarkers, wherein the presence, absence, location, ratio, or quantity of descriptive features determines a score, relative to a control, wherein the score correlates to the classification of Barrett's esophagus.

In another embodiment, the method further detects at least one or more biomarkers selected from the group consisting of Ki-67, beta-catenin, matrix metalloproteinase 1, CD68, CD4, forkhead box P3, thrombospondin-1, C-myc, fibroblast activation protein alpha, cyclin D1, EGFR, Interleukin-6, PLAU plasminogen activator urokinase (uPA), Fas, and FasL.

In another embodiment, the classification of Barrett's esophagus comprises no dysplasia, reactive atypia, low grade dysplasia, and high grade dysplasia.

In another embodiment, the method further comprises one or more probes that specifically bind to each of the biomarkers.

In another embodiment, at least 10, at least 20, at least 30, at least 40, at least 50, at least 60, at least 70, or 71 descriptive features from Table 6.

In another embodiment, the sample comprises a brushing, biopsy, or surgical resection of cells and/or tissue from the subject.

In another embodiment, the descriptive features are identified, located, analyzed, determined, or detected in subcellular and/or tissue compartments.

In another embodiment, the descriptive features further comprises one or more morphometric markers selected from the group consisting of nuclear area, nuclear equivalent diameter, nuclear solidity, nuclear eccentricity, gland to stroma ratio, nuclear area to cytoplasmic area ratio, glandular nuclear size, glandular nuclear size and intensity gradient, and nuclear texture.

In another embodiment, the sample is at room temperature or frozen. In yet another embodiment, the sample is freshly obtained, formalin fixed, alcohol fixed, or paraffin embedded.

In another embodiment, the probes are fluorescent and/or comprise a fluorescent tag, preferably wherein each probe is labeled with a different fluorophore.

In another embodiment, the subset of biomarkers comprises at least 3 biomarkers and wherein the 3 biomarkers are an epithelial biomarker, immune biomarker and/or a stromal biomarker. In yet another embodiment, the method further detects a stem cell biomarker. In another embodiment, the method detects 2 or more, 3 or more, 4 or more, 5 or more, 8 or more, or 12 or more biomarkers are determined simultaneously. In yet another embodiment, the subject is a human.

In another embodiment, the invention relates to a kit for determining, testing, calculating, or assessing a risk of progression of Barrett's esophagus in a subject comprising: a) one or more probes that is capable of detecting at least two or more biomarkers from the group consisting of p53, HIF-1alpha, beta-catenin, and COX-2; and b) instructions for using the probes to determine one or more descriptive features to generate a score from a cell and/or tissue sample of a subject.

In another embodiment, the kit further comprises probes that are capable of detecting at least one or more biomarkers detected are selected from the group consisting of p16, Ki-67, alpha-methylacyl-CoA racemase (AMACR, P504S), matrix metalloproteinase 1, CD1a, NF-kappa-B, CD68, CD4, forkhead box P3, CD45RO, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, and FasL.

In another embodiment, the kit further comprises probes that are capable of detecting at least one or more biomarkers selected from the group consisting of AMACR, CD1a, CD45RO, CD68, CK-20, Ki-67, NF-κB, and p16.

In another embodiment, at least 10, at least 20, at least 30, at least 40, at least 50, or 60 descriptive features from Tables 4. In another embodiment, at least 10, at least 20, at least 30, at least 40, at least 50, at least 60, at least 70, at least 80, or 89 descriptive features from Table 5.

In another embodiment, the present invention relates to a kit for classifying Barrett's esophagus in a subject, comprising: a) one or more probes that is capable of detecting at least two or more biomarkers from the group consisting of HIF-1alpha, p53, CD45RO, p16, AMACR, CK-20, CDX-2, HER2, CD1a, COX-2, NF-κB, Ki-67, CD68, Beta-catenin, and nucleic acid; and b) instructions for using the probes to determine one or more descriptive features to generate a score from a cell and/or tissue sample of a subject.

In another embodiment, the kit further comprises probes that are capable of detecting at least one or more biomarkers selected from the group consisting of Ki-67, beta-catenin, matrix metalloproteinase 1, CD68, CD4, forkhead box P3, thrombospondin-1, C-myc, fibroblast activation protein alpha, cyclin D1, EGFR, Interleukin-6, PLAU plasminogen activator urokinase (uPA), Fas, and FasL.

In another embodiment, at least 10, at least 20, at least 30, at least 40, at least 50, at least 60, at least 70, or 71 descriptive features from Table 6.

In another embodiment, the score is predictive of the clinical outcome of Barrett's esophagus in the subject and/or diagnostic of the subclass of Barrett's esophagus in the subject. In another embodiment, the probes comprise antibody probes that specifically bind to said biomarkers. In another embodiment, the probes are fluorescent and/or comprise a fluorescent tag.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
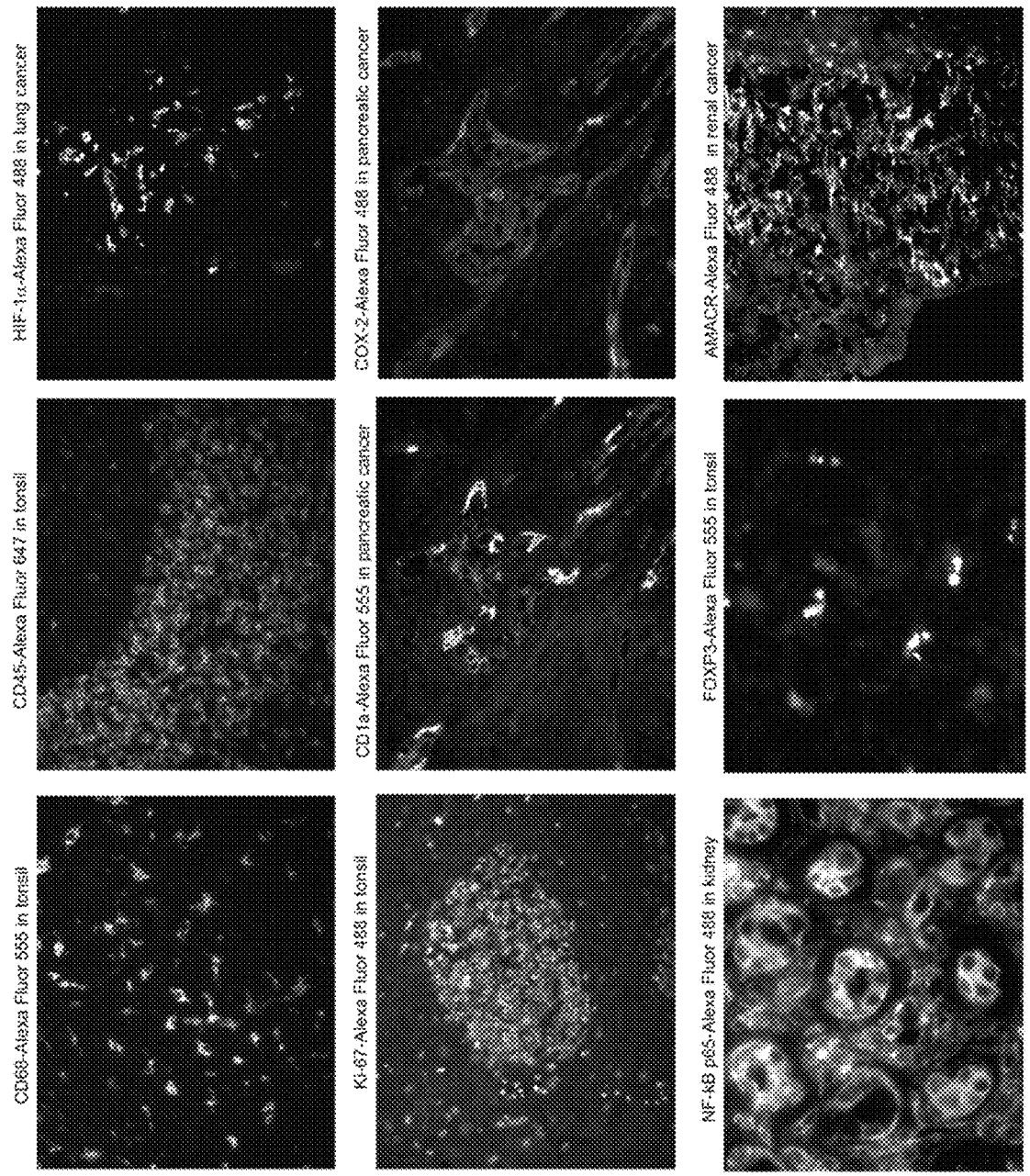
FIG. 1 depicts a multiplexed fluorescence labeling and digital imaging of biomarkers in sections of various tissues including tonsil tissue.
Figure 2:
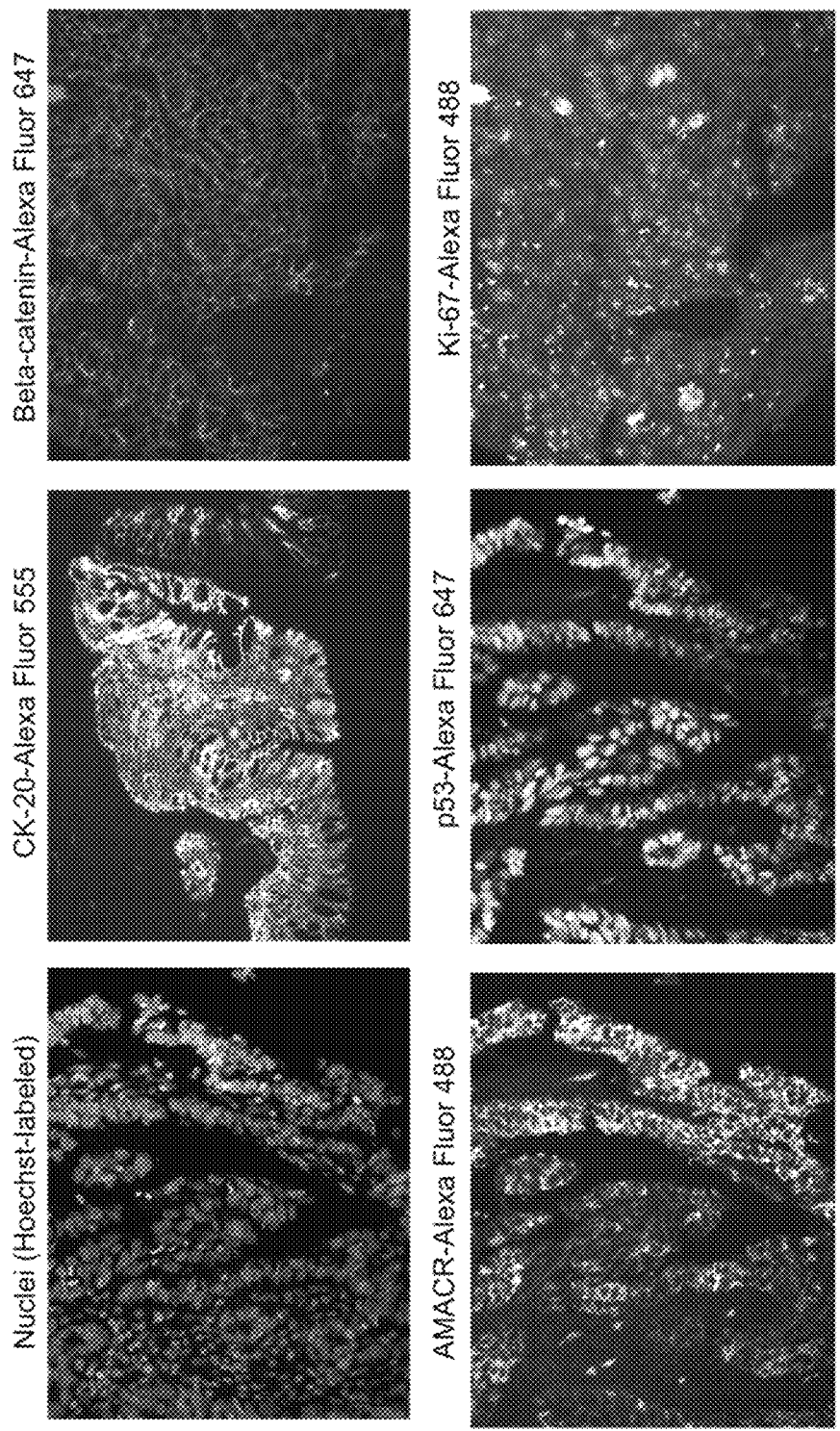
FIG. 2 depicts a multiplexed fluorescence labeling and digital imaging of nuclei and biomarkers in sections of dysplastic Barrett's esophagus biopsies.
Figure 3:
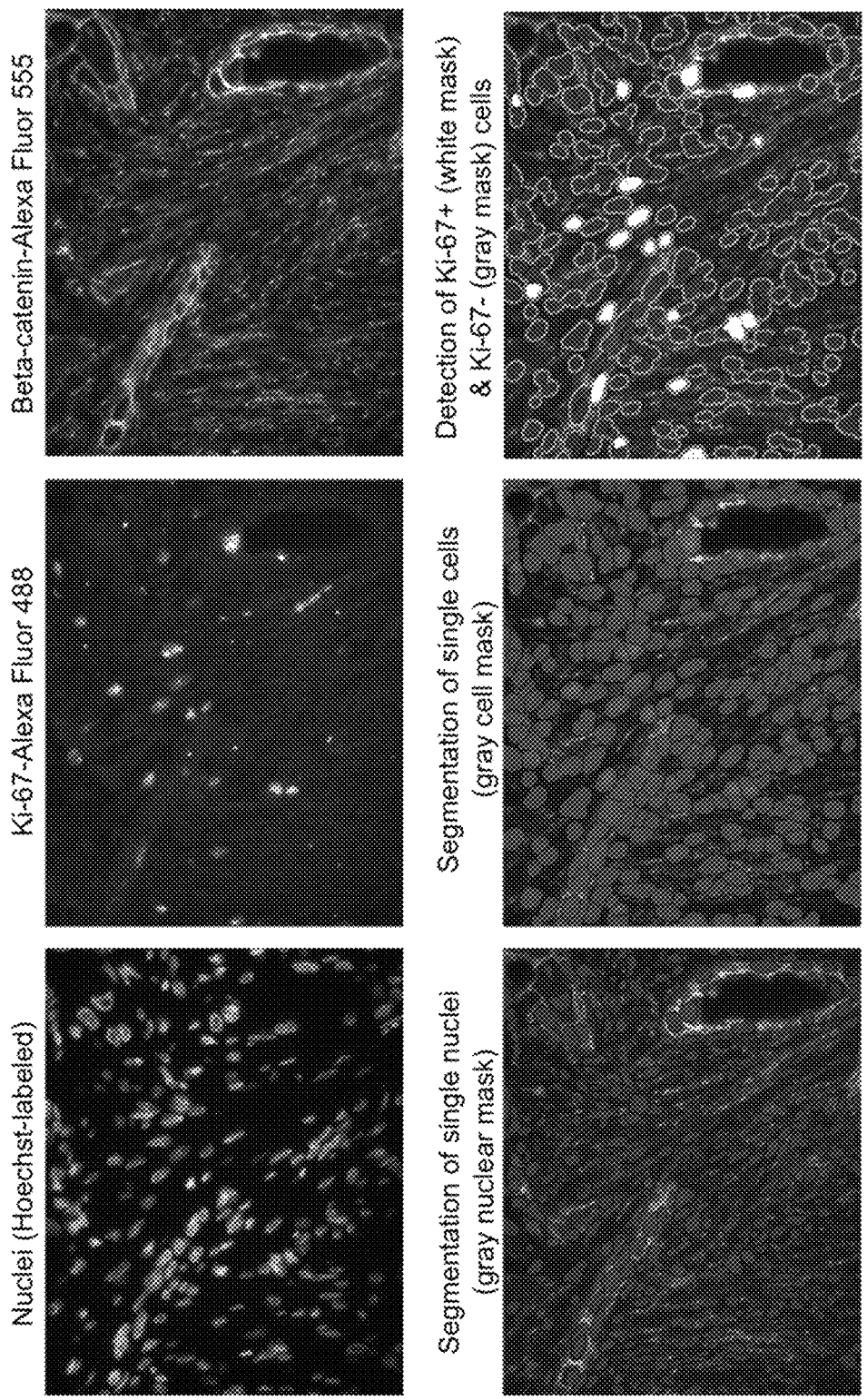
FIG. 3 depicts digital image analysis to segment nuclei (dark grey nuclei masks) and cells as individual objects (dark grey cell masks) and to identify Ki-67-positive (white masks) and Ki-67-negative cells (dark grey masks) within a tissue sample.
Figure 4:
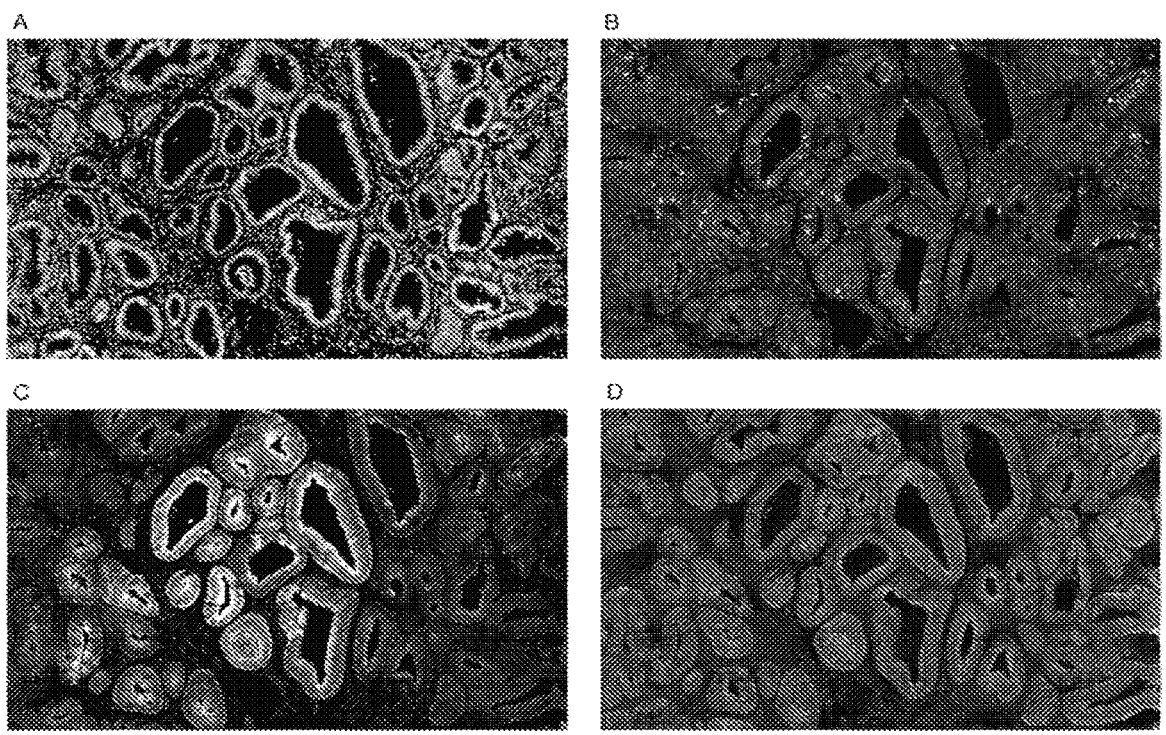
FIG. 4 depicts Digital Fluorescence Images of Barrett's Esophagus with High Grade Dysplasia Biopsy Tissue Section Stained with Biomarker Subpanel 1. A: Hoechst labeling (nuclei), B: Ki-67-Alexa Fluor 488, C: CK-20-Alexa Fluor 555, D: Beta-catenin-Alexa Fluor 647.
Figure 5:
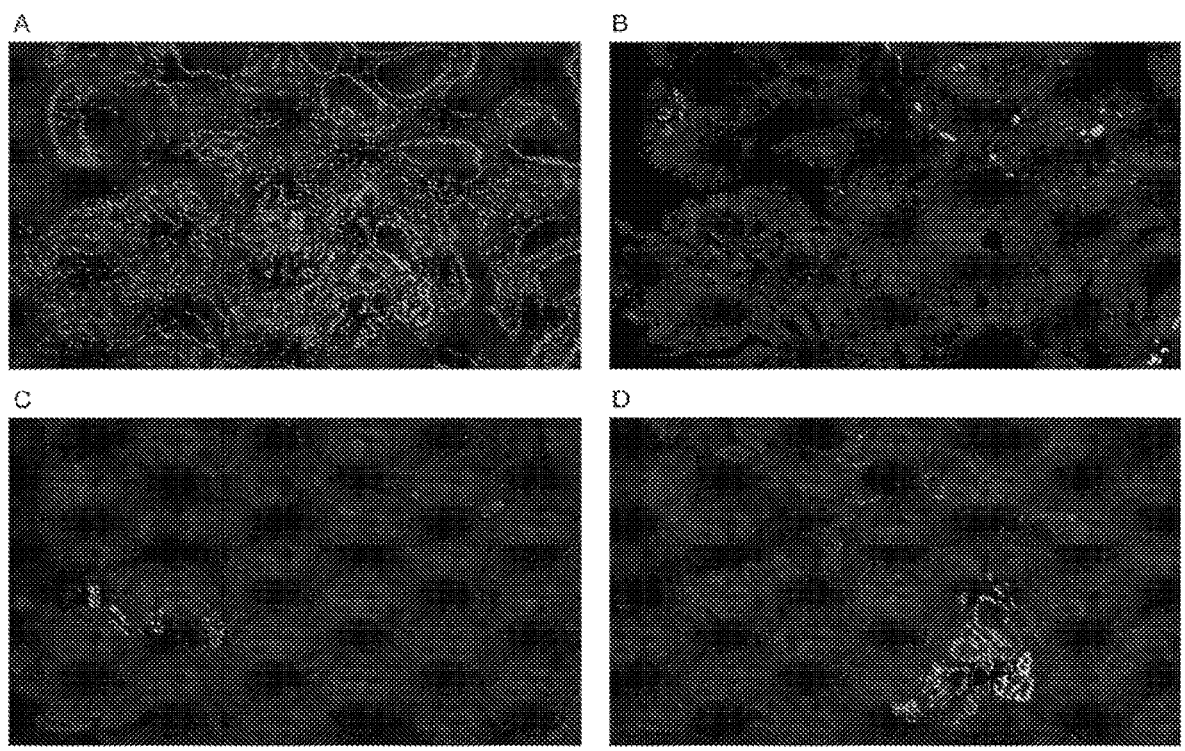
FIG. 5 depicts Digital Fluorescence Images of Esophageal Adenocarcinoma in a Background of Barrett's Esophagus Biopsy Tissue Section Stained with Biomarker Subpanel 2. A: Hoechst labeling (nuclei), B: p16-Alexa Fluor 488, C: AMACR-Alexa Fluor 555, D: p53-Alexa Fluor 647.
Figure 6:
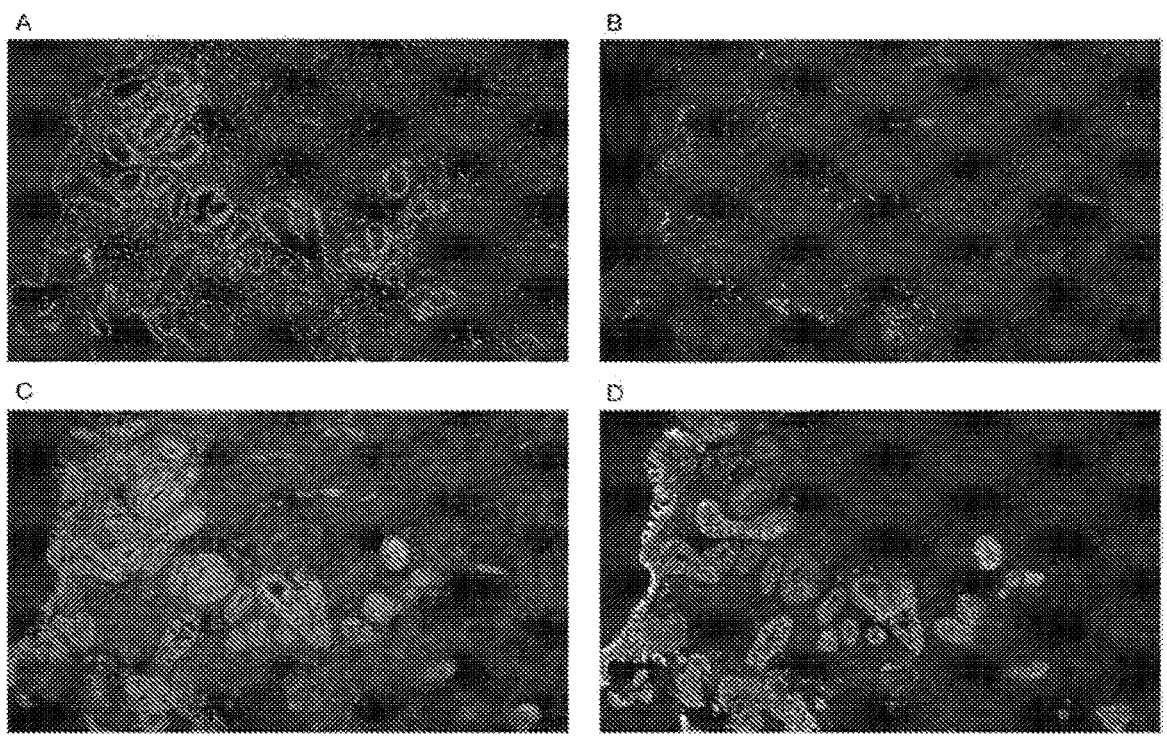
FIG. 6 depicts Digital Fluorescence Images of a Barrett's Esophagus with Low Grade Dysplasia Biopsy Tissue Section Stained with Biomarker Subpanel 3. A: Hoechst labeling (nuclei), B: CD68-Alexa Fluor 488, C: NF-κB-Alexa Fluor 555, D: COX-2-Alexa Fluor 647.
Figure 7:
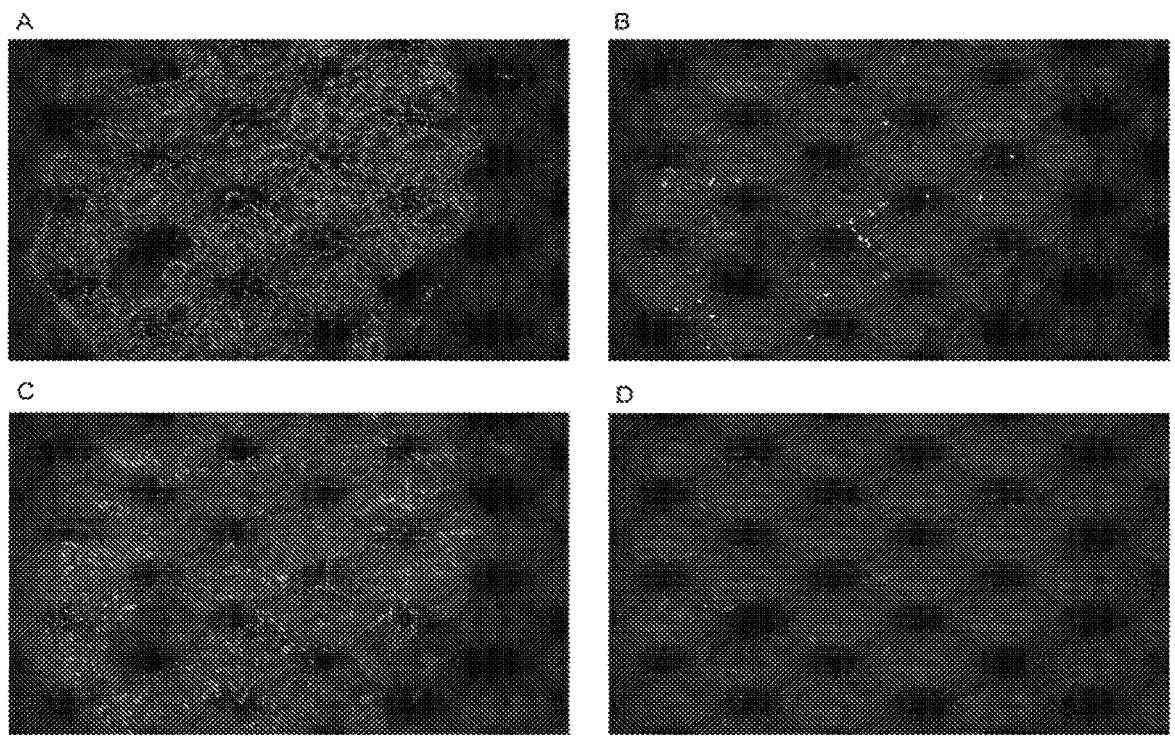
FIG. 7 depicts Digital Fluorescence Images of a Barrett's Esophagus Without Dysplasia Biopsy Tissue Section Stained with Biomarker Subpanel 4. A: Hoechst labeling (nuclei), B: HIF1-alpha-Alexa Fluor 488, C: CD45RO-Alexa Fluor 555, D: CD1a-Alexa Fluor 647.
Figure 8:
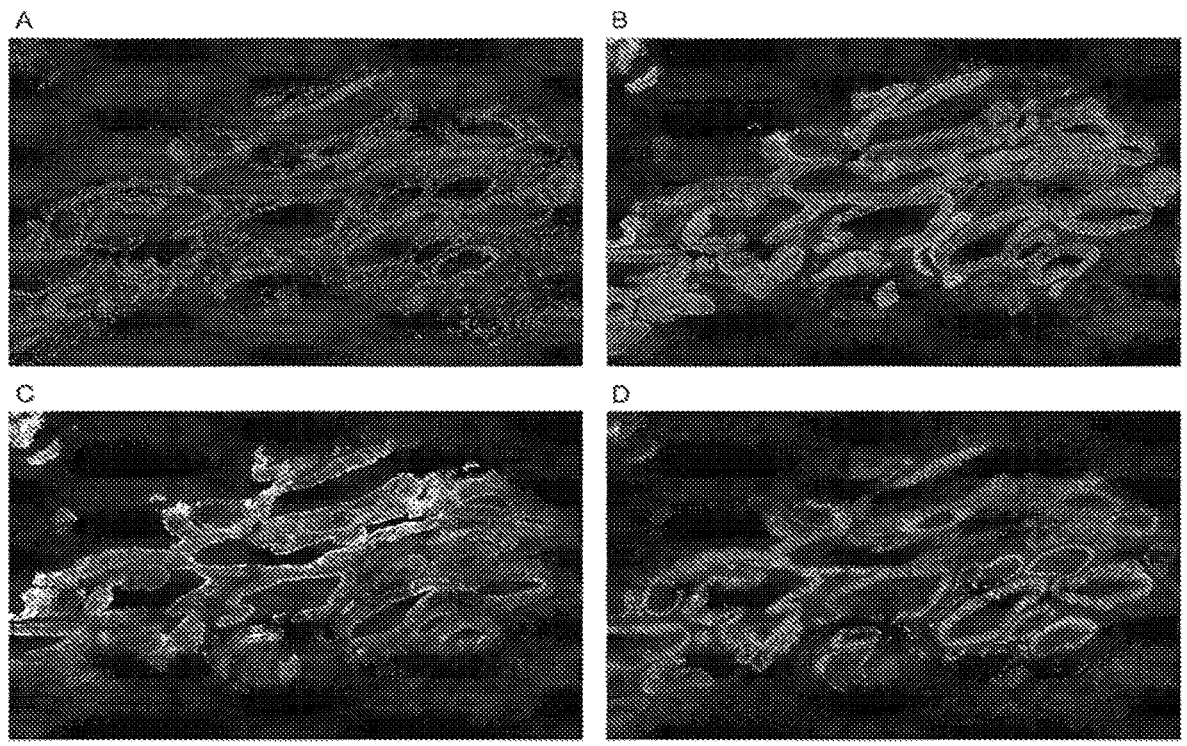
FIG. 8 depicts Digital Fluorescence Images of a Barrett's Esophagus With High Grade Dysplasia Biopsy Tissue Section Stained with Biomarker Subpanel 5. A: Hoechst labeling (nuclei), B: HER2/neu-Alexa Fluor 488, C: CK-20-Alexa Fluor 555, D: CDX-2-Alexa Fluor 647.

A description of example embodiments of the invention follows.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods. As used herein, the terms "increase" and "decrease" mean, respectively, to cause a statistically significantly (i.e., p<0.15) increase or decrease of at least 1%, 2%, or 5%.

As used herein, the recitation of a numerical range for a variable is intended to convey that the invention may be practiced with the variable equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 0 and 2 takes the values 0, 1 or 2 if the variable is inherently discrete, and takes the values 0.0, 0.1, 0.01, 0.001, $10^{-12}$, $10^{-11}$, $10^{-10}$, $10^{-9}$, $10^{-8}$, $10^{-7}$, $10^{-6}$, $10^{-5}$, $10^{-4}$ or any other real values$\geq 0$ and $\leq 2$ if the variable is inherently continuous.

As used herein, unless specifically indicated otherwise, the word "or" is used in the inclusive sense of "and/or" and not the exclusive sense of "either/or."

The term "amino acid" refers to a molecule containing both an amino group and a carboxyl group bound to a carbon which is designated the α-carbon. Suitable amino acids include, without limitation, both the D- and L-isomers of the naturally occurring amino acids, as well as non-naturally occurring amino acids prepared by organic synthesis or other metabolic routes. In some embodiments, a single "amino acid" might have multiple sidechain moieties, as available per an extended aliphatic or aromatic backbone scaffold. Unless the context specifically indicates otherwise, the term amino acid, as used herein, is intended to include amino acid analogs, naturally occurring amino acids, and non-naturally amino acids.

The term "antibody" refers to an immunoglobulin molecule or fragment thereof having a specific structure that interacts or binds specifically with a molecule comprising an antigen. As used herein, the term "antibody" broadly includes full-length antibodies and may include certain antibody fragments thereof. Also included are monoclonal and polyclonal antibodies, multivalent and monovalent antibodies, multispecific antibodies (for example bi-specific antibodies), chimeric antibodies, human antibodies, humanized antibodies and antibodies that have been affinity matured. An antibody binds selectively or specifically to a biomarker of a gastrointestinal disorder if the antibody binds preferentially to an antigen expressed by a cell and has less than 25%, or less than 10%, or less than 1% or less than 0.1% cross-reactivity with a polypeptide expressed by a cell within the gastrointestinal tissue or cells derived from another tissue that migrates from one tissue to the gastrointestinal tissue. Usually, the antibody will have a binding affinity (dissociation constant (Kd) value), for the antigen or epitope of no more than $10^{-6}$M, or $10^{-7}$M, or less than about $10^{-8}$M, or $10^{-9}$M, or $10^{-10}$M, or $10^{-11}$M or $10^{-12}$M. Binding affinity may be assessed using any method known by one of ordinary skill in the art, such as surface plasma resonance, immunoaffinity assays, or ELISAs.

As used herein, the term "biomarker" means any analyte, metabolite, nucleic acid, amino acid sequence or fragments thereof, polyprotein, protein complex, molecule, or chemical compound that is produced, metabolized, catabolized, secreted, phagocytosed, or expressed by a cell or tissue and that provides a useful measure of the presence, absence, or quantity of a certain cell type or descriptive feature indicative of, characteristic of, or suggestive of a diagnosis of a particular disease or disorder.

As used herein, the term "epithelial biomarker" means any marker of epithelial cell subset, e.g. normal gland or surface epithelium cell, metaplastic gland or surface epithelium cell, dysplastic gland or surface epithelium cell, cancer cell of epithelial origin, or marker of epithelial cell function, e.g. proliferation, cell cycle control, tumor suppressor gene, oncogene, adhesion, migration, fatty acid metabolism, apoptosis, inflammation.

As used herein, the term "stromal biomarker" means any marker of stromal cell type, e.g. endothelial cell, fibroblast, or stromal cell function, e.g. angiogenesis, tissue remodeling.

As used herein, the term "immune biomarker" means any marker of immune cell subset, e.g. T lymphocyte, B lymphocyte, supressor cell, regulatory T cell, dendritic cell, macrophage, granulocyte, or immune cell function, e.g. cytokines, chemokines, activation, cell-cell contact, proliferation, inflammation.

As used herein, the term "nucleic acid biomarker" means any specific locus of a gene or DNA sequence measured with locus-specific probes, e.g. 9p21, 8q24.12-13, 17q11.2-q12. It also includes centromeres measured with centromere enumeration probes, e.g. chromosome 8, 9, 17. It also includes anything that binds to nucleic acid and can aid in the visualization of the nucleus (e.g. Hoechst, 4',6-diamidino-2-phenylindole (DAPI)).

As used herein, the term "morphometric marker" means any measurement of structures, shapes, parts, sizes and textures of cells and tissues. Examples of morphometric markers include nuclear area, nuclear equivalent diameter, nuclear solidity, nuclear eccentricity, gland to stroma ratio, nuclear area to cytoplasmic area ratio, glandular nuclear size, glandular nuclear size and intensity gradient, and nuclear texture. The term "nuclear equivalent diameter" means a scalar that specifies the diameter of a circle with the same area as the nuclear region and can be computed as sqrt(4*Area/pi). It is an estimate of the diameter of nuclei, which are non-circular, irregularly-shaped objects. The term "nuclear solidity" means a scalar specifying the proportion of the pixels in the convex hull that are also in the nuclear region. It is equal to the ratio of nucleararea:convexarea of nuclei based on fluorescent labeling of nuclei. The term "nuclear eccentricity" is a scalar that specifies the eccentricity of the nuclear ellipse that has the same second-moments as the nuclear region. The eccentricity is the ratio of the distance between the foci of the ellipse and its major axis length. The value is between 0 and 1. The term "nuclear texture" is the spatial arrangements of fluorescently-labeled pixels in nuclei area.

As used herein, the term "stem cell biomarker" means any marker to distinguish stem cells from non-stem cells or marker of stem cell function.

In some embodiments, the disease is a gastrointestinal disorder. In some embodiments, the biomarker is chosen from one or more of the molecules identified in Table 1. In some embodiments, the biomarkers can be the measure of receptor expression levels, transcription factor activation; location or amount or activity of a protein, polynucleotide, organelle, and the like; the phosphorylation status of a protein, etc. In one embodiment, a biomarker is a nucleic acid (e.g., DNA, RNA, including micro RNAs, snRNAs, mRNA, rRNA, etc.), a receptor, a cell membrane antigen, an intracellular antigen, and extracellular antigen, a signaling molecule, a protein, and the like without limitation, lipids, lipoproteins, proteins, cytokines, chemokines, growth factors, peptides, nucleic acids, genes, and oligonucleotides, together with their related complexes, metabolites, mutations, variants, polymorphisms, modifications, fragments, subunits, degradation products, elements, and other analytes or sample-derived measures. A biomarker can also include a mutated protein or proteins, a mutated nucleic acid or mutated nucleic acids, variations in copy numbers, and/or transcript variants, in circumstances in which such mutations, variations in copy number and/or transcript variants are useful for generating a predictive model, or are useful in predictive models developed using related markers (e.g., non-mutated versions of the proteins or nucleic acids, alternative transcripts, etc.).

The term "biomaterial or biomaterials" means any protein, tissue, molecule, extracellular matrix component, biostructure, membrane, subcellular compartment or any combination of the above that is derived from a cell and/or is spatially positioned outside of cell in a cell sample.

As used herein, the terms "a biomarker expression profile" means a collection of data collected by a user related to the quantity, intensity, presence, absence, or spatial distribution of a biomarker or set of biomarkers assigned to a cell or biomaterial or subcellular compartment, each within a cell sample.

As used herein, the term "cell sample" means a composition comprising an isolated cell or plurality of cells. In some embodiments, the cell sample comprises an individual cell. In some embodiments, the cell sample is a composition comprising a plurality of cells. In some embodiments, the cell sample is a tissue sample taken from a subject with a gastrointestinal disorder. In one embodiment, the cell sample is a tissue sample. In some embodiments, the cell sample comprises a plurality of cells from the gastrointestinal tract. In some embodiments, the cell sample is a plurality of esophageal cells. In some embodiments, the cell sample is freshly obtained, formalin fixed, alcohol-fixed and/or paraffin embedded. In some embodiments, the cell sample is a biopsy isolated from a subject who has been diagnosed or is suspected or identified as having one or more gastrointestinal disorders. In one embodiment, the cell sample a biopsy isolated from a subject who has been diagnosed or is suspected or identified as having Barrett's esophagus. In another embodiment, the cell sample comprises a tissue from a brushing, punch biopsy, or surgical resection of a subject. In one embodiment of the invention, the one or more tissue samples are isolated from one or more animals. For example, in one embodiment, the one or more animals are one or more humans. In a particular embodiment, one or more cell samples are isolated from a human patient at one or more time points, such that at least one tissue sample is isolated from each time point from the same patient. In some embodiments, a cell sample can include a single cell or multiple cells or fragments of cells or an aliquot of body fluid, taken from a subject, by means including venipuncture, excretion, ejaculation, massage, biopsy, needle aspirate, lavage sample, scraping, surgical incision, or intervention or other means known in the art. In another embodiment, the invention includes obtaining a cell sample associated with a subject, where the sample includes one or more biomarkers. The sample can be obtained by the subject or by a third party, e.g., a medical professional. Examples of medical professionals include physicians, emergency medical technicians, nurses, first responders, psychologists, medical physics personnel, nurse practitioners, surgeons, dentists, and any other obvious medical professional as would be known to one skilled in the art. A sample can include peripheral blood cells, isolated leukocytes, or RNA extracted from peripheral blood cells or isolated leukocytes. The sample can be obtained from any bodily fluid, for example, amniotic fluid, aqueous humor, bile, lymph, breast milk, interstitial fluid, blood, blood plasma, cerumen (earwax), Cowper's fluid (pre-ejaculatory fluid), chyle, chyme, female ejaculate, menses, mucus, saliva, urine, vomit, tears, vaginal lubrication, sweat, serum, semen, sebum, pus, pleural fluid, cerebrospinal fluid, synovial fluid, intracellular fluid, and vitreous humour. In an example, the sample is obtained by a blood draw, where the medical professional draws blood from a subject, such as by a syringe. The bodily fluid can then be tested to determine the value of one or more descriptive features using the interpretation function or methods described herein. The value of the one or more descriptive features can then be evaluated by the same party that performed the method using the methods of the invention or sent to a third party for evaluation using the methods of the invention. In one embodiment of the invention, the method comprises obtaining or isolating at least two cell samples from one or more subjects. In one embodiment of the invention, the method comprises obtaining or isolating at least three cell samples from one or more subjects. In one embodiment of the invention, the method comprises obtaining or isolating at least four cell samples from one or more subjects. Any suitable tissue sample can be used in the methods described herein. For example, the tissue can be epithelium, muscle, organ tissue, nerve tissue, tumor tissue, and combinations thereof. In one embodiment, the cell sample is not derived from blood, sera, or blood cells. In one embodiment, the cell sample is not derived from cells of the liver, pancreas, gallbladder, bladder, skin, heart, lungs, kidneys, spleen, bone marrow, adipose tissue, nervous system, circulatory system, or lymphatic system. Samples of tissue can be obtained by any standard means (e.g., biopsy, core puncture, dissection, and the like, as will be appreciated by a person of skill in the art). In some embodiments, at least one cell sample is labeled with a histological stain, to produce a histologically stained cell sample. As used in the invention described herein, histological stains can be any standard stain as appreciated in the art, including but not limited to, alcian blue, Fuchsin, haematoxylin and eosin (H&E), Masson trichrome, toluidine blue, Wright's/Giemsa stain, and combinations thereof. In some embodiment, as will be appreciated by a person of skill in the art, traditional histological stains are not fluorescent. At least one other section is labeled with a panel of fluorescently labeled reagents to produce a fluorescently labeled section. As used in the invention described herein, the panel of fluorescently labeled reagents comprises a number of reagents, such as fluorescently labeled antibodies, fluorescently labeled peptides, fluorescently labeled polypeptides, fluorescently labeled aptamers, fluorescently labeled oligonucleotides (e.g. nucleic acid probes, DNA, RNA, cDNA, PNA, and the like), fluorescently labeled chemicals and fluorescent chemicals (e.g., Hoechst 33342, propidium iodide, Draq-5, Nile Red, fluorescently labeled phalloidin, 4',6-diamidino-2-phenylindole (DAPI)), and combinations thereof.

"Cellular systems biology" is defined as the of the interacting cellular and molecular networks of normal, tumor, immune, stromal and stem cells in tissues and bodily fluids that give rise to normal function and disease. Cells in tissues, as complex systems, exhibit properties that are not anticipated from the analysis of individual components, known as emergent properties that require analysis of many factors to characterize cellular and molecular states. In some embodiments, correlation between measurements in individual cells is required to identify and interpret cellular responses to drug treatment. A cellular systems biological profile can be utilized to capture or compile a set of epidemiological data about a patient or subject population. In some embodiments, the subject population is a patient population at an elevated risk for developing Barrett's esophagus, suffering from Barrett's esophagus, or having been diagnosed with Barrett's esophagus. All kits and methods of the present invention may also be used to compile data around epidemiological data about a patient or subject population. All kits and methods of the present invention may also be used to acquire and track the progression of a particular disease or disorder of a subject. In some embodiments, the subject population is a patient population at an elevated risk for developing Barrett's esophagus, suffering from Barrett's esophagus, or having been diagnosed with Barrett's esophagus. In some embodiments, particular expression levels of biomarkers are tracked and patient histories are compiled in order to more finely characterize a patient's disease as falling into a particular subclass of Barrett's esophagus.

"Clinical factor" is defined as a measure of a condition of a subject, e.g., disease activity or severity. "Clinical factor" encompasses all biomarkers of a subject's health status, including non-sample markers, and/or other characteristics of a subject, such as, without limitation, age and gender, and clinical history related to other ailments, disorders, diseases, or the risk associated with developing such ailment, disorder, or disease. A clinical factor can be a score, a value, or a set of values that can be obtained from evaluation of a cell sample (or plurality of samples) from a subject or a subject under a determined condition. A clinical factor can also be predicted by biomarkers and/or other parameters such as gene expression surrogates.

As used herein, the term "classifying Barrett's esophagus" means assigning a diagnostic subcategory or risk score to a subject. Diagnostic subcategories include:
  Barrett's esophagus, no dysplasia
  Barrett's esophagus, reactive atypia
  Barrett's esophagus, indefinite for dysplasia
  Barrett's esophagus, low grade dysplasia
  Barrett's esophagus, high grade dysplasia
  Esophageal adenocarcinoma As used herein, the term "control" means healthy esophageal tissue, Barrett's esophagus tissue with no dysplasia, Barrett's esophagus tissue from a subject that did not progress to low grade or high grade dysplasia, or esophageal carcinoma.

As used herein, the term "converting" means subjecting the one or more descriptive features to an interpretation function or algorithm for a predictive model of disease. In some embodiments, the disease is Barrett's esophagus or a subclass of Barrett's esophagus. In some embodiments, the interpretation function can also be produced by a plurality of predictive models. In one of the possible embodiments, the predictive model would include a regression model and a Bayesian classifier or score. In one embodiment, an interpretation function comprises one or more terms associated with one or more biomarker or sets of biomarkers. In one embodiment, an interpretation function comprises one or more terms associated with the presence or absence or spatial distribution of the specific cell types disclosed herein. In one embodiment, an interpretation function comprises one or more terms associated with the presence, absence, quantity, intensity, or spatial distribution of the morphological features of a cell in a cell sample. In one embodiment, an interpretation function comprises one or more terms associated with the presence, absence, quantity, intensity, or spatial distribution of descriptive features of a cell in a cell sample.

As used herein, "transmutes said digital imaging data into a digital imaging signal" means the process of a data processor that receives digital imaging data and converts the digital code of said digital imaging data into a code compatible with the software used to create an image of a cell sample visible to a user.

As used herein, "descriptive features" are defined as values associated with data measurements, a series of data measurements, observations, or a series of observations about a cell sample, typically evidenced by the presence, absence, quantity, localization or spatial proximity to other descriptive features or biomarkers relative space within a cell sample. Examples of descriptive features include values calculated through an image interpretation function, measured or quantified by standard or known microscopy techniques, but are not limited to values associated with the presence, absence, localization, or spatial distribution of one or more biomarkers. Examples of descriptive features include values calculated through an image interpretation function, measured or quantified by standard or known microscopy techniques, but are not limited to values associated with the presence, absence, localization, or spatial distribution of one or more biomarkers chosen from: protein post-translational modifications such as phosphorylation, proteolytic cleavage, methylation, myristoylation, and attachment of carbohydrates; translocations of ions, metabolites, and macromolecules between compartments within or between cells; changes in the structure and activity of organelles; and alterations in the expression levels of macromolecules such as coding and non-coding RNAs and proteins. In some embodiments, descriptive features comprise values associated with one or a combination of more than one of the following morphological features of a cell or cell sample chosen from: the presence of goblet cells; the presence of cytological and architectural abnormalities; the presence of cell stratification; the presence of multilayered epithelium; the maturation of the surface epithelium; the degree of budding, irregularity, branching, and atrophy in crypts; the proportion of low grade crypts to high grade crypts; the presence of splaying and duplication of the muscularis mucosa; the presence, number and size of thin-walled blood vessels, lymphatic vessels, and nerve fibers; the frequency of mitoses; the presence of atypical mitoses; the size and chromicity of nuclei; the presence of nuclear stratification; the presence of pleomorphism; the nucleus: cytoplasm volume ratio; the presence of villiform change; the presence of the squamocolumnar junction (Z-line) and its location in relation to the gastroesophageal junction; the presence of ultra-short segment Barrett's esophagus; the intestinal differentiation in nongoblet columnar epithelial cells; the presence of longated, crowded, hyperchromatic, mucin-depleted epithelial cells; the degree of loss of cell polarity; the penetration of cells through the original muscularis mucosa; the infiltration of dysplastic cells beyond the basement membrane into the lamina propria. In some embodiments, the descriptive feature may represent a numerical value estimated by an operator of the apparati or compositions disclosed herein using methods of quantifying such biomarkers as it is known in the art. In some embodiments, the descriptive feature comprises a value or values associated with the presence, absence, proximity, localization relative to one or more biomarkers, or quantity of one or more of the following cell types: epithelial cells, multi-layered-epithelial cells, endothelial cells, peripheral mononuclear lymphocytes, T cells, B cells, natural killer cells, eosinophils, mast cells, macrophages, dendritic cells, neutrophils, fibroblasts, goblet cells, dysplastic cells, and non-goblet columnar epithelial cells. In some embodiments, the descriptive feature comprises value related to the presence, absence, localization or relative proximity to other descriptive features or biomarkers, or quantity of one or more of the following biomarkers inside or outside a cell: p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha. The detection of a biomarker in one or more sections is a read-out of one or more descriptive features of a cellular systems biology profile. In some embodiments, a "descriptive feature" refers to a characteristic and/or a value which relates to a measurement or series of measurements related to a particular biomarker (which can indicate the location, function, spatial distribution, presence or absence of the biomarker made within a cell sample. Biological functions include, but are not limited to: protein posttranslational modifications such as phosphorylation, proteolytic cleavage, methylation, myristoylation, and attachment of carbohydrates; translocations of ions, metabolites, and macromolecules between compartments within or between cells; changes in the structure and activity of organelles; and alterations in the expression levels of macromolecules such as coding and non-coding RNAs and proteins, morphology, state of differentiation, and the like. A single biomarker can provide a read-out of more than one feature. For example, Hoechst dye detects DNA, which is an example of a biomarker. A number of features can be identified by the Hoechst dye in the cell sample such as nucleus size, cell cycle stage, number of nuclei, presence of apoptotic nuclei, etc.

As used herein, the term "derived from" in the context of the relationship between a cell or amino acid sequence and a related biomarker or related amino acid sequence describes a biomarker or related amino acid sequence that may be homologous to or structurally similar to the related chemical structure or related amino acid sequence.

As used herein, the term "digitally addressable" means an image that can be viewed, manipulated, or accessed by the user with software.

As used herein, the terms "gastrointestinal disorder" refers to any disease or abnormality related to the alimentary canal including but not necessarily limited to one or more of the following conditions: abdominal pain, gastroesophageal reflux disease (GERD), constipation, diarrhea, diverticulosis, gastrointestinal bleeding, stomach cancer, esophageal cancer, intestinal cancer, colon cancer, Barrett's esophagus, irritable bowel disease, infectious colitis, ulcerative colitis, Crohn's disease, ischemic colitis, radiation colitis, irritable bowel syndrome, acute perforation, ileus, appendicitis, intra-abdominal abscesses, intestinal obstruction, gastritis, autoimmune metaplastic atrophic gastritis, ulcers in the stomach, peptic ulcer disease, dyspepsia, gastrointestinal stromal tumors, small bowel tumors, levator syndrome, pilonidal disease, proctits, fistulkas, fissures, incontinence The terms "highly correlated gene expression" or "highly correlated marker expression" refer to biomarker expression values that have a sufficient degree of correlation to allow their interchangeable use in a predictive model of Barrett's esophagus. For example, if gene x having expression value X is used to construct a predictive model, highly correlated gene y having expression value Y can be substituted into the predictive model in a straightforward way readily apparent to those having ordinary skill in the art and the benefit of the instant disclosure. Assuming an approximately linear relationship between the expression values of genes x and y such that $Y=a+bX$, then X can be substituted into the predictive model with $(Y-a)/b$. For non-linear correlations, similar mathematical transformations can be used that effectively convert the expression value of gene y into the corresponding expression value for gene x. The terms "highly correlated marker" or "highly correlated substitute marker" refer to markers that can be substituted into and/or added to a predictive model based on, for instance, the above criteria. A highly correlated marker can be used in at least two ways: (1) by substitution of the highly correlated biomarker(s) for the original biomarker(s) and generation of a new model for predicting Barrett's esophagus risk; or (2) by substitution of the highly correlated biomarker(s) for the original biomarker (s) in the existing model for predicting a subject's propensity to develop, risk to develop, or diagnosis or Barrett's esophagus or a subclass of Barrett's esophagus.

As used herein, the term "instructions" refers to materials and methods for staining tissue slides with the probes, imaging the probes on the tissue slides, analyzing the images to extract the biomarker data and/or the processing the data into a score.

As used herein, the term "location" refers to a subcellular compartment or tissue compartment. Subcellular compartments include the nucleus, cytoplasm, plasma membrane, and nuclear membrane. Tissue compartments include the surface epithelium, glands, stroma, and tumor.

As used herein, the term "probe" refers to any molecule that binds or intercalates to a biomarker, either covalently or non-covalently. In some embodiments, the probes include probe sets which include one or more probes that bind a single biomarker. The term "probe set" is sometime interchangeable for a panel of two or more probes that allow the detection of one or more biomarkers. In some embodiments the probe or probes are fluorescently labeled. In some embodiments, each fluorescently labeled probe is specific for at least one biomarker. In one embodiment of the invention, the panel of fluorescently labeled probes detects at least about two different biomarkers. In one embodiment of the invention, the panel of fluorescently labeled probes detects at least about three different biomarkers. In one embodiment of the invention, the panel of fluorescently labeled probes detects at least about four different biomarkers. In one embodiment of the invention, the panel of fluorescently labeled probes detects at least about five different biomarkers. In another embodiment of the invention, the panel of fluorescently labeled probes detects at least about four to about six, to about ten, to about twelve different biomarkers or more. In another embodiment of the invention, the panel of fluorescently labeled probes detects at least about three different biomarkers. In a further embodiment, each fluorescently labeled probe has different fluorescent properties, which are sufficient to distinguish the different fluorescently labeled probes in the panel.

As used herein, the term "ratio" means the ratio of one biomarker's quantity to a different biomarker's quantity in the same or different subcellular compartment or tissue compartment. It can also mean the ratio of one biomarker's quantity in a subcellular compartment to quantity of same biomarker in another subcellular compartment within the same cell. It can also mean the ratio of one biomarker's quantity in a tissue compartment to quantity of same biomarker in another tissue compartment within the same biopsy.

As used herein, the term "risk of progression" means the probability of progressing to low grade dysplasia, high grade dysplasia, or esophageal adenocarcinoma.

The term "score" refers to a single value that can be used as a component in a predictive model for the diagnosis, prognosis, or clinical treatment plan for a subject, wherein the single value is calculated by combining the values of descriptive features through an interpretation function or algorithm. In some embodiments, the subject is suspected of having, is at risk of developing, or has been diagnosed with a gastrointestinal disorder. In another embodiment the subject is suspected of having or is at risk of developing Barrett's esophagus or a subclass of Barrett's esophagus. Risk scores are scores of 1-100, with 1 indicating lowest risk of progression and 100 indicating highest risk of progression. Risk classes are be low, intermediate and high.

The term "subclass of Barrett's esophagus" refers to any presentation of Barrett's esophagus classified as having any common combination of one or more descriptive features. In some embodiments, a subclass of Barrett's esophagus refers to one of the following conditions: Barrett's esophagus, no dysplasia, no progression in 5 years; Barrett's esophagus, no dysplasia, progression to low/high grade dysplasia in 5 years; Barrett's esophagus, indefinite for dysplasia, no progression in 5 years; Barrett's esophagus, indefinite for dysplasia, progression to low/high grade dysplasia or adenocarcinoma in 5 years; Barrett's esophagus, reactive atypia; Barrett's esophagus, low grade dysplasia, no progression in 5 years; Barrett's esophagus, low grade dysplasia, progression to high grade dysplasia or adenocarcinoma in 5 years; Barrett's esophagus, high grade dysplasia; Esophageal adenocarcinoma arising in a background of Barrett's esophagus.

In some embodiments, a subclass of Barrett's esophagus refers to one of the following conditions: low-grade dysplasia, high-grade dysplasia, reactive atypia, or indeterminate Barrett's esophagus. In some embodiments of the invention, the compositions and systems described herein are designed to stratify patient groups more precisely and diagnose the different subclasses of Barrett's esophagus more accurately.

The term "optical scanner" is used throughout the specification to describe any device or series of devices that generates image data from a cell sample or set of cell samples. In some embodiments, optical scanner is used to describe any device or series of devices that generates digital image data from a cell sample or set of cell samples. In some embodiments, the optical scanner may be a microscope attached to a optical device that generates digital image data, which, when sent to image forming apparatus such as a laser printer, a barcode reader, a confocal scanning laser microscope, or an imaging display (monitor), can produce an image visible to a user.

The term "subject" is used throughout the specification to describe an animal from which a cell sample is taken. In some embodiment, the animal is a human. For diagnosis of those conditions which are specific for a specific subject, such as a human being, the term "patient" may be interchangeably used. In some instances in the description of the present invention, the term "patient" will refer to human patients suffering from a particular disease or disorder. In some embodiments, the subject may be a human suspected of having or being identified as at risk to develop a gastrointestinal disorder. In some embodiments, the subject may be a human suspected of having or being identified as at risk to develop Barrett's esophagus. In some embodiments, the subject may be a mammal which functions as a source of the isolated cell sample. In some embodiments, the subject may be a non-human animal from which a cell sample is isolated or provided. The term "mammal" encompasses both humans and non-humans and includes but is not limited to humans, non-human primates, canines, felines, murines, bovines, equines, and porcines.

The terms "treating" and "to treat", mean to alleviate symptoms, eliminate the causation either on a temporary or permanent basis, or to prevent or slow the appearance of symptoms. The term "treatment" includes alleviation, elimination of causation (temporary or permanent) of, or prevention of symptoms and disorders associated with any condition. The treatment may be a pre-treatment as well as a treatment at the onset of symptoms.

In one embodiment of the invention, provided is a method for producing a cellular systems biology profile of one or more cell samples. As used herein, "cellular systems biology" (also referred to herein as systems cell biology), is the investigation of the integrated and interacting networks of genes, proteins, and metabolites that are responsible for normal and abnormal cell functions. In some embodiments, a cellular systems biology profile refers to a systemic characterization of cells in the context of a cell sample architecture such that the cells have particular characteristics dependent upon the relationships of different cells within a cell sample and the biological or medical state of the tissue when isolated from a subject. It is the interactions, relationships, and spatial orientation of the biomarkers of or biomaterials derived from a cell or cells from a cell sample that gives rise to the descriptive features that are used to construct a profile. The interrelationships within a cellular systems biology profile are defined or calculated, for example, either arithmetically (e.g., ratios, sums, or differences between descriptive features) or statistically (e.g., hierarchical clustering methods or principal component analyses of combinations of descriptive values). In a particular embodiment, a cellular systems biology profile defines the interrelationships between a combination of at least about two descriptive features collected from a cell or cells within a cell sample. In a particular embodiment, a cellular systems biology profile defines the interrelationships between a combination of at least about three descriptive features collected from a cell or cells within a cell sample. In a particular embodiment, a cellular systems biology profile defines the interrelationships between a combination of at least about four descriptive features collected from a cell or cells within a cell sample. In a particular embodiment, a cellular systems biology profile defines the interrelationships between a combination of at least about five descriptive features collected from a cell or cells within a cell sample. In another embodiment, a cellular systems biology profile is the combination of at least about six, seven, eight, nine, ten, eleven, twelve, or more descriptive features or values assigned to the descriptive features.

The presence, absence, localization or spatial distribution of, proximity to other biomarkers, or quantity of one or more biomarkers of the invention can be indicated as a value. A value can be one or more numerical values resulting from evaluation of a cell sample under a condition. The values can be obtained, for example, by experimentally obtaining measurements from a cell sample by using one of the systems or compositions disclosed herein. The values can be obtained, for example, by experimentally obtaining digital imaging data from a cell sample by using one of the systems or compositions disclosed herein. The values can be obtained, for example, by experimentally obtaining measurements from a cell sample by performing one of the methods described herein. Alternatively, one of ordinary skill in the art can obtain a digital imaging data from a service provider such as a laboratory, or from a database or a server on which the digital imaging data has been stored, e.g., on a storage memory.

System Components

The invention relates to a system comprising: a cell sample; a plurality of probes and/or stains; one or more optical scanners; one or more data processors; one or more data storage units; one or more monitors; wherein the one or more optical scanners, the one or more data processors, the one or more monitors, and the one or more data storage units are in digital communication with each other by a means to transmit digital data. In some embodiments the system comprises a cell sample isolated from a subject with a gastrointestinal disorder. In some embodiments, the system comprises a cell sample isolated from a subject with Barrett's esophagus or a subclass of Barrett's esophagus. In some embodiments, the cell sample is isolated from a subject suspected of having, being at risk for developing, or diagnosed with a gastrointestinal disorder. In some embodiments, the cell sample is isolated from a subject suspected of having, being at risk for developing, or diagnosed with Barrett's esophagus or a subclass of Barrett's esophagus.

Also described herein is a system for predicting Barrett's esophagus in a subject, the system including: a data storage unit or memory for storing one or more descriptive features associated with a cell sample obtained from the subject, wherein the descriptive features including quantitative expression or spatial distribution data for at least one biomarker set selected from the group consisting of the biomarker sets in term 1, term 2, and term 3; wherein terms 1 through 3 include any combination of one or more biomarkers p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha.

Also described herein is a system for predicting Barrett's esophagus in a subject, the system including: a data storage unit or memory for storing one or more descriptive features associated with a cell sample obtained from the subject, wherein the descriptive features including quantitative expression or spatial distribution data for at least one biomarker sets selected from the group consisting of the biomarker sets in term 1, term 2, term 3, and term 4; wherein terms 1 through 4 include any combination of one or more biomarkers p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha; and one or more data processors are operably coupled to the data storage unit, units, or memory for determining a score with an interpretation function wherein the score is predictive of a risk of developing or being diagnosed with Barrett's esophagus in the subject; and wherein at least one of the terms relates to the spatial distribution of one or more biomarkers. In some embodiments, the one or more data processors are remotely operated over a network. In some embodiments, the one or more data processors are remotely operated over a digital network.

Also described herein is a system for predicting Barrett's esophagus in a subject, the system including: a data storage unit or memory for storing one or more descriptive features associated with a cell sample obtained from the subject, wherein the descriptive features including quantitative expression or spatial distribution data for at least one biomarker set selected from the group consisting of the biomarker sets in term 1, term 2, and term 3; wherein term 1 includes Ki-67, term 2 includes beta-catenin, and term 3 includes the presence of nuclei stained by Hoescht stain, and wherein terms 1, 2, and 3 optionally include any one or more of the following biomarkers: alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha. In some embodiments, any of the methods described herein may contain a descriptive feature identified through computer recognition of the presence, absence, quantity, intensity, or spatial distribution of morphological components of the cell. In some embodiments, the terms of the biomarker sets may be added to calculate the score.

Also described herein is a system for predicting Barrett's esophagus in a subject, the system including: a data storage unit or memory for storing one or more descriptive features associated with a cell sample obtained from the subject, wherein the descriptive features including quantitative expression or spatial distribution data for at least one biomarker sets selected from the group consisting of the biomarker sets in term 1, term 2, term 3, and term 4; wherein terms 1 through 4 include any combination of one or more biomarkers p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha; and one or more data processors are operably coupled to the data storage unit, units, or memory for determining a score with an interpretation function wherein the score is predictive of a risk of developing or being diagnosed with Barrett's esophagus in the subject; and wherein at least one of the terms relates to the spatial distribution of one or more biomarkers.

Also described herein is a system for predicting Barrett's esophagus in a subject, the system including: a data storage unit or memory for storing one or more descriptive features associated with a cell sample obtained from the subject, wherein the descriptive features include quantitative expression or spatial distribution data for at least one biomarker sets selected from the group consisting of the marker sets in term 1, term 2, term 3, term 4, and term 5; wherein terms 1 through 5 include any combination of one or more biomarkers p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha; and a data processor communicatively coupled to the data storage unit, units, or memory for determining a score with an interpretation function wherein the score is predictive of Barrett's esophagus in the subject; and wherein at least one of the terms relates to the spatial distribution of one or more biomarkers.

Also described herein is a system for predicting Barrett's esophagus in a subject, the system including: a data storage unit or memory for storing one or more descriptive features associated with a cell sample obtained from the subject, wherein the descriptive features include quantitative expression or spatial distribution data for at least one biomarker sets selected from the group consisting of the marker sets in term 1, term 2, term 3, term 4, term 5, and term 6; wherein terms 1 through 6 include any combination of one or more biomarkers p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha; and a data processor communicatively coupled to the data storage unit, units, or memory for determining a score with an interpretation function wherein the score is predictive of Barrett's esophagus in the subject; and wherein at least one of the terms relates to the spatial distribution of one or more biomarkers.

Also described herein is a system for predicting Barrett's esophagus in a subject, the system including: a data storage unit or memory for storing one or more descriptive features associated with a cell sample obtained from the subject, wherein the descriptive features include quantitative expression or spatial distribution data for at least one biomarker sets selected from the group consisting of the marker sets in term 1, term 2, term 3, term 4, term 5, term 6, and term 7; wherein terms 1 through 7 include any combination of one or more biomarkers p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha; and a data processor communicatively coupled to the data storage unit, units, or memory for determining a score with an interpretation function wherein the score is predictive of Barrett's esophagus in the subject; and wherein at least one of the terms relates to the spatial distribution of one or more biomarkers.

Also described herein is a system for predicting Barrett's esophagus in a subject, the system including: a data storage unit, units or memory for storing one or more descriptive features associated with a cell sample obtained from the subject, wherein the descriptive features include quantitative expression data for at least one biomarker sets selected from the group consisting of the marker sets in term 1, term 2, term 3, term 4, optionally term 5, optionally term 6, and optionally term 7; wherein terms 1 through 7 include any combination of one or more biomarkers p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha; and a data processor communicatively coupled to the data storage unit, units, or memory for determining a score with an interpretation function wherein the score is predictive of Barrett's esophagus in the subject.

Also described herein is a computer-readable storage medium storing computer-executable program code, the program code including: program code for storing a dataset of descriptive features associated with a cell sample obtained from the subject, wherein the first dataset includes quantitative expression data for at least one marker set selected from the group consisting of the marker sets in term 1, term 2, term 3, optionally term 4, optionally term 5, optionally term 6, and optionally term 7; wherein terms 1 through 7 include any combination of one or more biomarkers p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha; and program code for determining a score with an interpretation function wherein the score is predictive of Barrett's esophagus in the subject.

In some embodiments, the invention relates to software on an electronic medium or system comprising such software used to correlate the cluster groups of biomarker, morphologic and clinical data features into indices useful to distinguish one or more particular cell types from a mixture of cell types in a cell sample automatically.

In some embodiments, the invention relates to software on an electronic medium or system comprising such software used. to correlate the cluster groups of biomarker, morphologic and clinical data features into indices useful to predict the responsiveness a patient to a particular therapy.

In some embodiments, the invention relates to software on an electronic medium or system comprising such software used to correlate the cluster groups of biomarker, morphologic and clinical data features into indices useful to predict one or more clinical treatment schedules for a patient automatically.

In some embodiments, the invention relates to software on an electronic medium or system comprising such software used to correlate the cluster groups of biomarker, morphologic and clinical data features into indices useful to predict the risk of developing one or more diseases or conditions automatically.

Generation and Analysis of Digital Imaging Data

The quantity of one or more biomarkers of the invention can be indicated as a value. A value can be one or more numerical values resulting from evaluation of a sample under a condition. The values can be obtained, for example, by experimentally obtaining measurements from a cell sample by an performing an assay in a laboratory, or alternatively, obtaining a dataset from a service provider such as a laboratory, or from a database or a server on which the dataset has been stored, e.g., on a storage memory. In an embodiment, a cell sample is obtained or provided by a subject. In some embodiments, the methods or compositions comprising the cell sample or set of cell samples comprise the identification of the subject as having a gastrointestinal disorder. In some embodiments, methods of generating or analyzing the cell sample or set of cell samples comprise the identification of the subject as having an increased risk to develop a gastrointestinal disorder. In some embodiments, methods of generating or analyzing the cell sample or set of cell samples comprise the identification of the subject as having a reduced risk to develop a gastrointestinal disorder as compared to the general population. In some embodiments, methods of generating or analyzing the cell sample or set of cell samples comprise the identification of the subject as not having a gastrointestinal disorder. In some embodiments, methods of generating or analyzing the cell sample or set of cell samples comprise the identification of the subject as having a Barrett's esophagus. Once identified, the cell samples are provided to perform an analysis of the cell or plurality of cells, biomaterial or biomaterials within the cell sample. In one embodiment of the invention, a cell sample or a dataset of descriptive features derived from the cell sample are analyzed by one or more data processors that either, individually or collectively: (i) analyzes the digital image data to identify, measure, or quantify one or more descriptive features from the plurality of probes and/or stains; and (ii) converts the one or more descriptive features into a score, wherein (ii) optionally comprises integrating stored data about a subject or group of subjects to convert the one or more descriptive features into a score. In some embodiments, the invention relates to a system that comprises: (a) a cell sample; (b) a plurality of probes and/or stains that bind to biomarkers of the cell sample; and (c) Datasets associated with descriptive features one or more data processors that either, individually or collectively: (i) analyzes the digital image data to identify, measure, or quantify one or more descriptive features from the plurality of probes and/or stains; and (ii) converts the one or more descriptive features into a score, wherein (ii) optionally comprises integrating stored data about a subject or group of subjects to convert the one or more descriptive features into a score.

Descriptive features of the tissue are determined by performing microscopy on a cell sample or set of cell samples in parallel or in sequence. In some embodiments, the descriptive features may be imaged and quantified by brightfield microscopy or fluorescent microscopy or a device that performs both brightfield and fluorescent microscopy by use of one or more wavelength filters. In some embodiments, the microscope is in operable communication to one or more data processors.

In one embodiment, the invention relates to a system or apparatus that comprises one or more data processors, each in operable communication with at least one optical scanner, that: (a) receives digital image data; and (b) may optionally transmute said digital imaging data into a digital imaging signal, which can be create a digital image of the cell sample; and (c) analyzes the digital image data to identify, measure, or quantify one or more descriptive features from a plurality of probes and/or stains that bind to biomarkers of the cell sample. In some embodiments, the system or apparatus optionally comprises one or more data storage units, each in operable communication with at least one processor. The analysis of the digital image data is performed by the one or more data processors that creates datasets associated with the presence, absence, quantity or spatial distribution of two or more biomarkers.

In an embodiment, a descriptive feature can include one clinical factor or a plurality of clinical factors. In an embodiment, a clinical factor can be included within a dataset. A dataset can include one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more, or thirty or more overlapping or distinct clinical factor(s). A clinical factor can be, for example, the condition of a subject in the presence of a disease or in the absence of a disease. Alternatively, or in addition, a clinical factor can be the health status of a subject. Alternatively, or in addition, a clinical factor can be age, gender, chest pain type, neutrophil count, ethnicity, disease duration, diastolic blood pressure, systolic blood pressure, a family history parameter, a medical history parameter, a medical symptom parameter, height, weight, a body-mass index, resting heart rate, and smoker/non-smoker status. Clinical factors can include whether the subject has stable chest pain, whether the subject has been diagnosed with a hiatal hernia, whether the subject has GERD, whether the subject has an gastritis, whether the subject has been previously diagnosed with Barrett's esophagus, whether the subject has had a gastrointestinal procedure, whether the subject has diabetes, whether the subject has an inflammatory condition, whether the subject has an infectious condition, whether the subject is taking a steroid, whether the subject is taking an immunosuppressive agent, and/or whether the subject is taking a chemotherapeutic agent.

The compiled dataset is converted into a score or scores, which then can be used to correlate the descriptive features of the cell sample into a biological profile or predictive outcome for the subject.

Biomarkers and Descriptive Features

The quantity of one or more biomarkers of the invention can be indicated as a descriptive feature, provided in terms of a value. The quantity is the amount of any specific biomarker in a cellular or tissue compartment. The signal intensity for each biomarker in the tissue images is directly proportional to the biomarker quantity. A value can be one or more numerical values resulting from analysis of a cell sample under a condition. The values can be obtained, for example, by obtaining an image of a cell sample.

In an embodiment, the quantity of one or more markers can be one or more numerical values associated with expression levels of: p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha; resulting from evaluation of a cell sample under a condition. This nomenclature is used to refer to human genes in accordance with guidelines provided by the Human Genome Organization (HUGO) Gene Nomenclature Committee (HGNC). Further information about each human gene, such as accession number(s) and aliases, can be found by entering the gene name into the search page on the HGNC Search genenames.org website. For example, entering the term "CD45" into the Simple Search field of the HGNC website on Feb. 14, 2011 returns the approved gene name of PTPRC (protein tyrosine phosphatase, receptor type C, the sequence accession IDs of Y00062 and NM_002838 and the previous symbols of CD45.

Also described herein is a computer-implemented method for scoring a cell sample or plurality of cell samples obtained from a subject, including: obtaining a first dataset associated with the first sample, wherein the first dataset includes quantitative expression data for at least two markers selected from the group consisting of p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha; and determining, by a computer processor, a first score from the first dataset using an interpretation function, wherein the first score is predictive of Barrett's esophagus in the subject or class of subjects.

In an embodiment, a biomarker's associated value can be included in a digital imaging data associated with a sample obtained from a subject. A dataset can include the marker expression value or quantity of two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more, or thirty or more marker(s). For example, a dataset can include values corresponding to the presence, absence, quantity, location, or spatial relationship between and among: 9p21, 8q24.12-13, 17q11.2-q12 or centromeres.

In an embodiment, one or more markers can be divided into terms. Terms can include one marker, but generally include three or more markers. Terms can be included in a digital imaging data associated with a cell sample obtained or isolated from a subject. The dataset can include one or more terms, two or more terms, three or more terms, four or more terms, five or more terms, six or more terms, seven or more terms, eight or more terms, nine or more terms, or ten or more terms. In an embodiment, a term can include one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more, or thirty or more marker(s). In an embodiment, the markers are divided into distinct terms: term 1, term 2, term 3, term 4, term 5, term 6, and term 7. In another embodiment, certain terms correspond to certain biomarkers. One of several image analysis environments can be used to extract biomarkers and descriptive features from digital images as described in Mulrane, L., Rexhepaj, E., Penney, S., Callanan, J. J., Gallagher, W. M. (2008) Automated image analysis in histopathology: a valuable tool in medical diagnostics. Expert Review of Molecular Diagnostics, 8, 707-725.

In some embodiments, the system or apparatus comprises a plurality of probes and/or stains that bind one or more of the biomarkers in Table 1. All of the combinations of the biomarkers in Table 1 are contemplated by the invention.

TABLE 1

Table of TissueCipher Biomarkers (Normal = normal esophageal tissue without Barrett's metaplasia). Biomarkers are categorized according to their major functions.

| Biomarker Categories | Specific Biomarkers | NCBI Gene ID, full name | Other designations/ also known as | Biomarker measurements and relevant ranges |
|---|---|---|---|---|
| Proliferation | MKI67 (Ki-67) | 4288, antigen recognized by monoclonal antibody Ki-67 | Antigen KI-67 | 1-99% cells positive for Ki-67, measure proliferation index of epithelial, immune and stromal cells, average intensity 1.25-100 fold higher versus normal |
| Cell Type Masks | CD45 | 5788, Protein tyrosine phosphatase, receptor type, C | LCA; LY5; B220; CD45; T200; CD45R; GP180; PTPRC | 1-99% cells positive for CD45, provide mask of immune cells within tissue |
| | Cytokeratin-20 (CK-20) | 54474, Keratin 20 | K20; CD20; CK20; CK-20; KRT21; MGC35423; KRT20 | 1-99% positive for cytokeratin-20, provide mask of epithelial cells or dysplastic cells within tissue |
| Differentiation | CDX2 | 1045, CDX2 caudal type homeobox 2 | CDX3; CDX-3; CDX2 | 1-99% cells positive for CDX2, average intensity 1.25-100 fold higher versus normal |
| Apoptosis | p53 | 7157, tumor protein p53 | OTTHUMP00000221340; antigen NY-CO-13; cellular tumor antigen p53; p53 tumor suppressor; phosphoprotein p53; transformation-related protein 53 | 1-99% cells positive for p53, average intensity 1.25-100 fold higher versus normal |
| | Fas | 355, FAS Fas (TNF receptor superfamily, member 6) | APT1; CD95; FAS1; APO-1; FASTM; ALPS1A; TNFRSF6; FAS | 1-99% cells positive for Fas, average intensity 1.25-100 fold higher versus normal, ratio of Fas:FasL across tissue and in single cells |

TABLE 1-continued

Table of TissueCipher Biomarkers (Normal = normal esophageal tissue without Barrett's metaplasia). Biomarkers are categorized according to their major functions.

| Biomarker Categories | Specific Biomarkers | NCBI Gene ID, full name | Other designations/ also known as | Biomarker measurements and relevant ranges |
|---|---|---|---|---|
| | FasL | 356, FASLG Fas ligand (TNF superfamily, member 6) | FASL; CD178; CD95L; CD95-L; TNFSF6; APT1LG1; FASLG | 1-99% cells positive for FasL, average intensity 1.25-100 fold higher versus normal, ratio of Fas:FasL across tissue and in single cells |
| Cell Cycle Control | p16 | 1029, cyclin-dependent kinase inhibitor 2A (melanoma, p 16, inhibits CDK4) | ARF; MLM; P14; P16; P19; CMM2; INK4; MTS1; TP16; CDK4I; CDKN2; INK4A; MTS-1; P14ARF; P19ARF; P16INK4; P16INK4A; P16-INK4A; CDKN2A | 1-99% cells negative for p16, average intensity 1.25-100 fold less than normal |
| | Cyclin D1 | 595, CCND1 cyclin D1 | BCL1; PRAD1; U21B31; D11S287E; CCND1 | 1-99% cells positive for Cyclin D1, average intensity 1.25-100 fold higher versus normal |
| | C-MYC | v-myc myelocytomatosis viral oncogene homolog (avian) | MRTL; c-Myc; bHLHe39; MYC | 1-99% cells positive for C-MYC, average intensity 1.25-100 fold higher versus normal |
| Growth Factor Receptors | HER2/neu | 2064, ERBB2 v-erb-b2 erythroblastic leukemia viral oncogene homolog 2, neuro/glioblastoma derived oncogene homolog (avian) | NEU; NGL; HER2; TKR1; CD340; HER-2; MLN 19; HER-2/neu; ERBB2 | 1-99% cells positive for HER2/neu, average intensity 1.25-100 fold higher versus normal |
| | EGFR | 1956, EGFR epidermal growth factor receptor | ERBB; HER1; mENA; ERBB1; PIG61; EGFR | 1-99% cells positive for EGFR, average intensity 1.25-100 fold higher versus normal |
| Metabolism | Alpha-methylacyl-CoA racemase (AMACR) | 23600, Alpha-methylacyl-CoA racemase | RM; RACE; CBAS4; AMACR; p504s | 1-99% cells positive for AMACR, average intensity 1.25-100 fold higher versus normal |
| Inflammation | Nuclear factor-kappa-B p65 subunit (NF-kB p65) | 5970, v-rel reticuloendotheliosis viral oncogene homolog A (avian) | Nuclear factor NF-kappa-B p65 subunit; nuclear factor of kappa light polypeptide gene enhancer in B-cells 3; transcription factor p65; v-rel avian reticuloendotheliosis viral oncogene homolog A (nuclear factor of kappa light polypeptide gene enhancer in B-cells 3 (p65)); v-rel reticuloendotheliosis viral oncogene homolog A, nuclear factor of kappa light polypeptide gene enhancer in B-cells 3, p65 | Ratio of nuclear:cytoplasmic/non-nuclear NF-κB p65 0.1-100 |
| | Cyclo-oxygenase 2 (COX-2) | 5743, Prostaglandin-endoperoxide synthase 2 (prostaglandin G/H synthase and cyclooxygenase) | PGH synthase 2; PHS 11; cyclooxygenase 2b; cyclooxygenase-2; prostaglandin G/H synthase 2; prostaglandin G/H synthase and cyclooxygenase; prostaglandin H2 synthase 2 | 1-99% cells positive for COX-2, average intensity 1.25-100 fold higher versus normal |
| Immune Responses | CD68 | 968, CD68 molecule | CD68 antigen; macrophage antigen CD68; macrosialin; scavenger receptor class D, member 1 | 1-99% cells positive, ratio of CD68+ cells to CK-20+ cells or p53+ cells |

TABLE 1-continued

Table of TissueCipher Biomarkers (Normal = normal esophageal tissue without Barrett's metaplasia). Biomarkers are categorized according to their major functions.

| Biomarker Categories | Specific Biomarkers | NCBI Gene ID, full name | Other designations/ also known as | Biomarker measurements and relevant ranges |
|---|---|---|---|---|
| | CD1a | 909, CD1a molecule | CD1A antigen, a polypeptide; T-cell surface antigen T6/Leu-6; T-cell surface glycoprotein CD1a; cluster of differentiation 1 A; cortical thymocyte antigen CD1A; differentiation antigen CD1-alpha-3; epidermal dendritic cell marker CD1a; hTa1 thymocyte antigen | 1-50 % cells positive for CD1a |
| | CD4 | 920, CD4 molecule | CD4 antigen (p55); CD4 receptor; T-cell surface antigen T4/Leu-3; T-cell surface glycoprotein CD4 | 1-50% cells positive for CD4, 1-50% cells positive for both CD4 and FOXP3 |
| | Forkhead box P3 (FOXP3) | 50943, Forkhead box P3 | JM2; AIID; IPEX; PIDX; XPID; DIETER; MGC141961; MGC141963; FOXP3 | 1-50% cells positive for FOXP3, 1-50% cells positive for both FOXP3 and CD4 |
| | IL-6 | 3569, IL6 interleukin 6 (interferon, beta 2) | HGF; HSF; BSF2; IL-6; IFNB2; IL6 | 1-99% cells positive for IL-6, intensity of IL-6 1.25-100 fold higher versus normal |
| Angiogenesis | HIF-1α | 3091, HIF1A hypoxia inducible factor 1, alpha subunit (basic helix-loop-helix transcription factor) | HIF1; MOP1; PASD8; bHLHe78; HIF-1 alpha; HIF1-ALPHA; HIF1A. | 1-99% cells positive for HIF-1α, intensity of HIF-1α 1.25-100 fold higher versus normal |
| Adhesion, Invasion, Metastasis | uPA | 5328, PLAU plasminogen activator, urokinase | ATF; UPA; URK; uPA; PLAU | 1-99% cells positive for uPA, intensity of IL-6 1.25-100 fold higher versus normal |
| | Matrix metalloproteinae 1 (MMP1) | 4312, matrix metallopeptidase 1 (interstitial collagenase) | Fibroblast collagenase; interstitial collagenase; matrix metalloprotease 1 | 1-99% cells positive for MMP1, average intensity 1.25-100 fold higher versus normal |
| | Beta-catenin | 1499, catenin (cadherin-associated protein), beta 1, 88kDa | CTNNB; FLJ25606; FLJ37923; DKFZp686D02253; CTNNB1 | 1-99% cells positive for beta-catenin, ratio of nuclear: non-nuclear signal 0.1-100, average intensity 1.25-100 fold higher versus normal |
| Stromal Processes | Fibroblast activation protein alpha (FAPα) | 2191, fibroblast activation protein, alpha | 170 kDa melanoma membrane-bound gelatinase; OTTHUMP00000207304; integral membrane serine protease; seprase | 1-99% cells positive for FAPα, intensity of FAPα 1.25-100 fold higher versus normal |
| | Thrombospondin-1 (TSP1) | 7057, Thrombospondin-1 | Thrombospondin-1, p180 | 1-99% cells positive for TSP 1, intensity of TSP1 1.25-100 fold higher versus normal |
| Amplification, gains and losses of gene loci | 9p21 | 1029, cyclin-dependent kinase inhibitor 2A (melanoma, p 16, inhibits CDK4) | P16 (CDKN2A) gene loci on chromosome 9 | 0-2 signals per nuclei |
| | 8q24.12-13 | 4609, v-myc myelocytomatosis viral oncogene homolog (avian) | C-MYC gene loci on chromosome 8 | 0-200 signals per nuclei |
| | 17q11.2-q12 | 2064, RBB2 v-erb-b2 erythroblastic leukemia viral oncogene homolog 2, neuro/glioblastoma derived oncogene homolog (avian) | HER2 gene loci on chromosome 17 | 0-100 signals per nuclei |

TABLE 1-continued

Table of TissueCipher Biomarkers (Normal = normal esophageal tissue without Barrett's metaplasia). Biomarkers are categorized according to their major functions.

| Biomarker Categories | Specific Biomarkers | NCBI Gene ID, full name | Other designations/ also known as | Biomarker measurements and relevant ranges |
| --- | --- | --- | --- | --- |
| | Chromosome enumeration probe 9 | n/a | CEP9 | 0-4 signals per nuclei, identification and enumeration of chromosome 9, used for normalization of 9p21 signals |
| | Chromosome enumeration probe 8 | n/a | CEP8 | 0-4 signals per nuclei, identification and enumeration of chromosome 8, used for normalization of 8q24.12-13 signals |
| | Chromosome enumeration probe 17 | n/a | CEP17 | 0-4 signals per nuclei, identification and enumeration of chromosome 17, used for normalization of 17q11.2-q12 signals |

Analysis of Digital Imaging Data

The invention relates to optical scanning equipment, digital imaging equipment, or other scanner that generates digital imaging data about the presence, absence, location, quantity, and/or intensity of at least one probe or stain that binds a biomarker of the cell sample; and one or more data processors that, either individually or collectively: (i) receives the digital image data from the optical scanner and, optionally, transmutes said digital imaging data into a digital imaging signal; and (ii) analyzes the digital image data to identify, measure, or quantify one or more descriptive features from at least one probe and/or stain. In some embodiments, the data processor comprises optical scanning equipment and digital imaging equipment that generates digital imaging data about the presence, absence, location, quantity, and/or intensity of at least one probe or stain that binds a biomarker of the cell sample; and one or more data processors that, either individually or collectively: (i) receives the digital image data from the optical scanner and, optionally, transmutes said digital imaging data into a digital imaging signal; and (ii) analyzes the digital image data to identify, measure, or quantify one or more descriptive features from the plurality of probes and/or stains. In another embodiment, the invention relates to a single device that comprises digital imaging equipment such as an optical scanner and a data processor that collectively: (a) generate digital imaging data about the presence, absence, location, quantity, and/or intensity of at least one probe or stain that binds a biomarker of the cell sample; (b) receive the digital image data from the optical scanner and, optionally, transmutes said digital imaging data into a digital imaging signal which becomes projected on a monitor for viewing by an operator; and (c) analyze the digital image data to identify, measure, or quantify one or more descriptive features from the plurality of probes and/or stains.

In some embodiments, the analysis of the digital image data is performed by algorithms developed by devices that perform known algorithms and, optionally create an image by progressive scan, line scan, area transference or optical matrix scan. In some embodiments, the analysis of the digital image data is performed by one of many commercially available devices in the art such as: Scan Scope Systems (Aperio Technologies Inc.), Aphelion (ADCIS), Aureon Pathomatrix or Aureon DiscoveryPath (Aureon Laboratories), the BLISS workstation (Bacus Laboratories), TMAx (Beecher Instruments), GenoMx VISION (Biogenex), PATHIAM or TissueAnalytics System (Biolmagene, Inc.), Automated Cellular Imagain System III (Dako), CELLENGER (Definiens), AQUA (HistoRx), Discovery-1 or Discovery TMA (Molecular Devices, Corp), VisioMorph (Visopharm), HistoQuant (3DHistech), algorithms designed by SlidePath.

In some embodiments analysis of a digital image may be performed by any one of the methods described in U.S. Pat. Nos. 7,893,988, 7,860,292, 7,844,125, 7,826,649, 7,787,674, 7,738,688, 7,689,024, 7,668,362, 7,646,495, 7,602,524, 7,518,652, 7,502,519, 7,463,761, 7,457,446, 7,428,324, 7,257,268, 7,116,440, 7,035,478; each of which are incorporated by reference in their entirety.

In some embodiments analysis of a digital image may be performed by any one of the methods described in U.S. patent application Ser. No. 11/709,601 (US Application No. 20080008349), US Application No. 20080137937, or US Application No. 20080292153 which are incorporated by reference in their entirety.

In some embodiments, the analysis of the digital image data is performed by measuring patterns present in the pixel values of digital images using a computer-implemented network structure. The network structure includes a process hierarchy, a class network and a data network. The data network represents information associated with each pixel location in the form of image layers, thematic layers and object networks. The analysis system performs both pixel-oriented processing and object-oriented processing by using that combination of data representations that yields the fastest result. Pixel-oriented and object-oriented processing is combined so that fewer computations and less memory are used to analyze an acquired digital image. The data network includes image layers of pixel values associated with pixel locations that are linked to objects of object networks. Each object network has various layers of objects (also called object "levels"). The objects of the data network are classified into classes of the class network. The data network also includes thematic layers. Thematic layers are used in combination with the image layers and the object networks to analyze digital images. There is a one-to-one relationship between a pixel location and the thematic class of a thematic layer. For example, in one application, operations are performed on the pixel values associated with an object depending on the thematic class linked to each pixel location that is linked to the object. However, the analysis system can also analyze digital images without using thematic layers.

In a specification mode and before the pixel values are acquired, the user of the analysis system specifies the class network and the process hierarchy. The classes of the class network describe categories of objects that the user expects to find in the digital image. The user also specifies thematic classes that describe categories of pixel values. The process hierarchy describes how the digital image is to be analyzed in order to find a target object. The process hierarchy defines the process steps performed on the pixel values and objects. In the specification mode, the user also specifies types of links that are to connect process steps, classes and objects of the data network to each other. A link between two nodes describes the relationship between the two nodes.

In an execution mode, the analysis system performs the process steps on the acquired pixel values. By performing the process steps, pixel locations associated with particular pixel values are linked to objects, and the objects are categorized as belonging to specific classes of the class network. Pixel locations associated with particular pixel values are also categorized as belonging to one of the thematic classes. The analysis system links the process steps, classes and objects to each other in a manner that enables the analysis system to detect a target object that is defined by a class. For example, the analysis system can recognize where a predefined pattern occurs in the digital image.

Object-oriented image analysis can better recognize patterns in complex digital images than can pure pixel-oriented statistical processing. However, object-oriented processing is computationally more intensive and therefore slower than pure statistical processing. The more accurate pattern recognition of object-oriented image analysis can be retained, while at the same time reducing the amount of computations required, by combining object-oriented and pixel-oriented processing. For example, an object in a digital image can be analyzed by performing statistical processing only on pixel values associated with pixel locations that are linked to specific objects of an object network. In step one, a user of the analysis system specifies class network by defining the likelihood that objects of data network will belong to each particular class of class network. The user of the analysis system is, for example, a research doctor who is applying his expert knowledge to train the analysis system in the specification mode. In step two, the user specifies process hierarchy. The user specifies not only the individual process steps, but also the order in which the process steps are to be executed in the execution mode. In step three, the user specifies a filter and the user specifies the parameters of the filter. An example of a filter parameter is the size of the object to be filtered. The size can be defined as the border length of the object or the diameter of the object, measured in pixel units. In step four, the analysis system acquires the pixel values of first image layer. In step five, the analysis system runs in the execution mode and generates a data network by selectively linking pixel locations to objects according to the class network and the process hierarchy. Each object is generated by linking to the object pixel locations associated with pixel values having similar characteristics. In step six, a new image layer is generated by performing pixel-oriented processing only on those pixel values of first image layer whose pixel locations are linked to specific objects of first object network. In this manner, the computations required to analyze target patterns in the digital image are reduced, and the speed at which the patterns are recognized and measured is increased.

Morphological analysis of the tissue may be conducted by either visualizing the tissue or using an algorithm to measure the biomarker expression and other measurements from the analysis above to the morphology of the tissue consider importance of such measurements with respect to their spatial distribution. For instance, in one embodiment, a cell sample is provided from a healthy subject or a subject that has been identified as not having or having a low risk of developing Barrett's esophagus. Another cell sample is provided from a subject suspected as having Barrett's esophagus or identified as having Barrett's esophagus. In one embodiment, any of the methods provided herein comprise providing a cell sample taken from a subject identified as having Barrett's esophagus. The morphological aspects of the two cell samples are compared so that the relative frequency of biomarkers are assessed. In some embodiments, at least one or more of the following morphological aspects of the cell samples are compared: the presence of goblet cells; the presence of cytological and architectural abnormalities; the presence of cell stratification; the presence of multilayered epithelium; the maturation of the surface epithelium; the degree of budding, irregularity, branching, and atrophy in crypts; the proportion of low grade crypts to high grade crypts; the presence of splaying and duplication of the muscularis mucosa; the presence, number and size of thin-walled blood vessels, lymphatic vessels, and nerve fibers; the frequency of mitoses; the presence of atypical mitoses; the size and chromicity of nuclei; the presence of nuclear stratification; the presence of pleomorphism; the nucleus:cytoplasm volume ratio; the presence of villiform change; the presence of the squamocolumnar junction (Z-line) and its location in relation to the gastroesophageal junction; the presence of ultra-short segment Barrett's esophagus; the intestinal differentiation in nongoblet columnar epithelial cells; the presence of longated, crowded, hyperchromatic, mucin-depleted epithelial cells; the degree of loss of cell polarity; the penetration of cells through the original muscularis mucosa; the infiltration of dysplastic cells beyond the basement membrane into the lamina propria. In some embodiments, the spatial relationships among certain morphological aspects are compared. For example, a cell sample taken from a healthy subject or a subject identified as not having Barrett's esophagus may have very limited or completely absent intestinal differentiation in nongoblet columnar epithelial cells. In contrast, a cell sample taken from a subject suspected as having or having been identified as having Barrett's esophagus will have a moderate or high degree of intestinal differentiation in nongoblet columnar epithelial cells in spatially clustered positions among points in the tissue as compared to the cell sample from the healthy subject or the subject identified as not having Barrett's esophagus.

In some embodiments, the scores will be determined based upon the presence, absence, relative quantity, or spatial distribution of one of the following morphological features in the cell sample provided as compares to a cell sample taken from a subject having been identified as being at an increased risk of developing Barrett's esophagus or another gastrointestinal disorder. In some embodiments, the scores will be determined based upon the presence, absence, or spatial distribution, or relative quantity of one of the following morphological features as compared to a cell sample taken from a subject having been identified having Barrett's esophagus or another gastrointestinal disorder: the presence of goblet cells; the presence of cytological and architectural abnormalities; the presence of cell stratification; the presence of multilayered epithelium; the maturation of the surface epithelium; the degree of budding, irregularity, branching, and atrophy in crypts; the proportion of low grade crypts to high grade crypts; the presence of splaying and duplication of the muscularis mucosa; the presence, number and size of thin-walled blood vessels, lymphatic vessels, and nerve fibers; the frequency of mitoses; the presence of atypical mitoses; the size and chromicity of nuclei; the presence of nuclear stratification; the presence of pleomorphism; the nucleus:cytoplasm volume ratio; the presence of villiform change; the presence of the squamocolumnar junction (Z-line) and its location in relation to the gastroesophageal junction; the presence of ultra-short segment Barrett's esophagus; the intestinal differentiation in nongoblet columnar epithelial cells; the presence of longated, crowded, hyperchromatic, mucin-depleted epithelial cells; the degree of loss of cell polarity; the penetration of cells through the original muscularis mucosa; the infiltration of dysplastic cells beyond the basement membrane into the lamina propria.

Conversion of Data into Scores

In some embodiments of the invention, the operator of the system, devices, apparatuses and compositions of the present invention are used to identify one or more scores which can be correlated with clinical data from a subject to predict a clinical outcome, a clinical treatment, a responsiveness to a particular treatment, or a diagnosis of a subclass of a disease. In some embodiments, a subject or set of subjects is diagnosed with a particular subclass of Barrett's esophagus. After patterns are measured, a score or scores is assigned to the intensity or quantity of the identified patterns depending upon what descriptive features are identified in one or more cell samples provided. In some embodiments, spatial distribution of biomarkers and their relation to cell samples taken from subject or subject identified as not having Barrett's esophagus or other gastrointestinal disorder are reviewed to determine a score. An algorithm is then used to compile each score or set of scores for each cell sample and output the likelihood that a cell sample taken from a subject having been identified with a gastrointestinal disorder may have a particular subclass of Barrett's esophagus. In some embodiments, the method may comprises predicting whether a subject identified as having Barrett's esophagus may have Barrett's esophagus, no dysplasia, no progression in 5 years; Barrett's esophagus, no dysplasia, progression to low/high grade dysplasia in 5 years; Barrett's esophagus, indefinite for dysplasia, no progression in 5 years; Barrett's esophagus, indefinite for dysplasia, progression to low/high grade dysplasia or adenocarcinoma in 5 years; Barrett's esophagus, reactive atypia; Barrett's esophagus, low grade dysplasia, no progression in 5 years; Barrett's esophagus, low grade dysplasia, progression to high grade dysplasia or adenocarcinoma in 5 years; Barrett's esophagus, high grade dysplasia; or Esophageal adenocarcinoma arising in a background of Barrett's esophagus.

In one embodiment, the function used to correlate a score to a particular diagnosis of a gastrointestinal disorder is based on a predictive model. In an embodiment, the predictive model is selected from the group consisting of a partial least squares model, a logistic regression model, a linear regression model, a linear discriminant analysis model, a ridge regression model, and a tree-based recursive partitioning model. In an embodiment, the predictive model performance is characterized by an area under the curve (AUC) ranging from 0.68 to 0.70. In an embodiment, the predictive model performance is characterized by an AUC ranging from 0.70 to 0.79. In an embodiment, the predictive model performance is characterized by an AUC ranging from 0.80 to 0.89. In an embodiment, the predictive model performance is characterized by an AUC ranging from 0.90 to 0.99.

An example of a formula for a 4 feature classifier is:

$$P_{progression} = 1/e^{-z}$$

$$z = \beta_0 + \chi_1\beta_1 + \chi_2\beta_2 + \chi_3\beta_3 + \chi_4\beta_4$$

Where:
$P_{progression}$=probability of progression to low grade dysplasia, high grade dysplasia or esophageal adenocarcinoma
$\chi$=a feature
$\chi_1$=0.99 quantile fo p53 cell mean intensity
$\chi_2$=0.99 quantile of HIF1alpha cell mean intensity
$\chi_3$=0.05 quantile of beta-catenin cell mean intensity
$\chi_4$=0.5 quantile of COX-2 plasma membrane:nucleus ratio
$\beta$=regression coefficient for each biomarker feature obtained via fitting a generalized linear model using a logit link function Methods The invention relates to the use of the system, devices, apparatuses, kits and compositions to perform one or more steps of all of the methods discloses herein.

The invention relates to a method of determining a risk of progression of Barrett's esophagus in a subject, comprising: a) detecting a subset of biomarkers in a sample from the subject, wherein two or more biomarkers in said subset are selected from the group consisting p53, HIF-1alpha, beta-catenin, and COX-2; and b) determining at least one or more descriptive features listed in Table 4 or 5 associated with said biomarkers, wherein the presence, absence, location, ratio, or quantity of descriptive features determines a score, relative to a control, wherein the score correlates to the risk of progression of Barrett's esophagus in the subject. In another embodiment, at least one or more biomarkers selected from the group consisting of p16, Ki-67, alpha-methylacyl-CoA racemase (AMACR, P504S), matrix metalloproteinase 1, CD1a, NF-kappa-B, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, and FasL. In another embodiment, at least one or more biomarkers selected from the group consisting of AMACR, CD1a, CD45RO, CD68, CK-20, Ki-67, NF-κB, and p16. In another embodiment, the subject has an increased risk of progression to low grade dysplasia, high grade dysplasia or esophageal cancer. In another embodiment, the subject is diagnosed with no dysplasia, reactive atypia, indefinite for dysplasia, low grade dysplasia, or high grade dysplasia. In another embodiment, the method further comprises detecting the subset of biomarkers using probes that specifically bind to each of said biomarkers. In another embodiment, at least 10, at least 20, at least 30, at least 40, at least 50, or 60 descriptive features are determined from Table 4. In another embodiment, at least 10, at least 20, at least 30, at least 40, at least 50, at least 60, at least 70, at least 80, or 89 descriptive features are determined from Table 5.

The invention also relates to a method of classifying Barrett's esophagus in a subject, comprising: a) detecting a subset of biomarkers in a sample from the subject, wherein two or more biomarkers are selected from the group consisting of HIF-1alpha, p53, CD45RO, p16, AMACR, CK-20, CDX-2, HER2/neu, CD1a, COX-2, NF-κB, and a nucleic acid biomarker; and b) determining at least one or more descriptive features listed in Table 6 associated with said biomarkers, wherein the presence, absence, location, ratio, or quantity of descriptive features determines a score, relative to a control, wherein the score correlates to the classification of Barrett's esophagus. In another embodiment, at least one or more biomarkers selected from the group consisting of Ki-67, beta-catenin, matrix metalloproteinase 1, CD68, CD4, forkhead box P3, thrombospondin-1, C-myc, fibroblast activation protein alpha, cyclin D1, EGFR, Interleukin-6, PLAU plasminogen activator urokinase (uPA), Fas, and FasL. In another embodiment, the classification of Barrett's esophagus comprises no dysplasia, reactive atypia, low grade dysplasia, and high grade dysplasia. In another embodiment, the method further comprises detecting the subset of biomarkers using probes that specifically bind to each of said biomarkers. In another embodiment, at least 10, at least 20, at least 30, at least 40, at least 50, at least 60, at least 70, or 71 descriptive features are determined from Table 6.

In another embodiment, the methods further comprise the sample comprising a brushing, biopsy, or surgical resection of cells and/or tissue from the subject. In another embodiment, the methods further comprise descriptive features that are identified in subcellular and/or tissue compartments. In another embodiment, the methods further comprise descriptive features that further comprise one or more morphometric markers selected from the group consisting of nuclear area, nuclear equivalent diameter, nuclear solidity, nuclear eccentricity, gland to stroma ratio, nuclear area to cytoplasmic area ratio, glandular nuclear size, glandular nuclear size and intensity gradient, and nuclear texture. In another embodiment, the methods further comprise the sample that is at room temperature or frozen. In another embodiment, the methods further comprise the sample that is freshly obtained, formalin fixed, alcohol fixed, or paraffin embedded. In another embodiment, the methods further comprise probes that are fluorescent and/or comprise a fluorescent tag, preferably wherein each probe is labeled with a different fluorophore. In other embodiment, the methods further comprise the subset of biomarkers that comprise at least 3 biomarkers and wherein the 3 biomarkers are an epithelial biomarker, immune biomarker and/or a stromal biomarker. In another embodiment, the methods further detect a stem cell biomarker. In another embodiment, the methods further comprise the detection of 2 or more, 3 or more, 4 or more, 5 or more, 8 or more, or 12 or more biomarkers simultaneously. In another embodiment, the methods further comprise that the subject is a human.

The invention relates to a method of quantifying one or more biomarkers in a cell sample comprising: providing a cell sample, contacting a plurality of probes and or stains with cell sample either serially or simultaneously, and determining relative quantity of probes bound to a plurality of biomarkers using the system comprising: (a) a cell sample; (b) a plurality of probes and/or stains that bind to biomarkers of the cell sample; (c) one or more optical scanners that generates digital imaging data about the presence, absence, location, quantity, and/or intensity of at least one probe or stain that binds a biomarker of the cell sample; (d) one or more data processors, each in operable communication with at least one optical scanner, that, either individually or collectively:

(i) receives the digital image data from the optical scanner and, optionally, transmutes said digital imaging data into a digital imaging signal; and (ii) analyzes the digital image data to identify, measure, or quantify one or more descriptive features from the plurality of probes and/or stains; and (iii) converts the one or more descriptive features into a score, wherein (iii) optionally comprises integrating stored data about a subject or group of subjects to convert the one or more descriptive features into a score; (e) one or more monitors, each in operable communication with at least one data processor, that comprises a screen and that receives a component of the digital images, or, optionally, receives the digital imaging signal from the data processor and projects a digitally addressable image onto its screen; and (f) one or more data storage units, each in operable communication with at least one processor.

The invention also relates to a method of diagnosing Barrett's esophagus comprising: (a) providing a cell sample of tissue; (b) contacting a plurality of probes with cell sample; (c) identifying one or more descriptive features; (d) determining one or more scores based upon the presence, absence, or quantity of descriptive features; and (e) correlating the score to a subclass of Barrett's esophagus. In some embodiments one or more steps of the method is/are performed using any one or more of the compositions, apparatuses, devices, kits or systems disclosed herein.

Cell samples are obtained from a biopsy (such as a punch biopsy), cut and fixed onto a slide or slides, and then each slide or slides is digitally imaged and digitally analyzed by on or more of the methods described herein to identify the presence, absence, relative quantity and/or spatial distribution of biomarkers in the cell sample.

The invention also relates to a method of determining patient responsiveness to a therapy for gastrointestinal tract disorders comprising: (a) providing a plurality of cell samples; (b) contacting a plurality of probes with each cell sample; (c) identifying one or more descriptive features of each cell sample; (d) determining one or more scores of each cell sample based upon the presence, absence, or quantity of descriptive features; and (e) predicting patient responsiveness to a therapy to treat or prevent a gastrointestinal disorder based upon the score.

The invention also relates to a method of compiling a cellular systems biological profile of a subject r set of subjects comprising: (a) providing one or more cell samples from a set of subjects; (b) contacting a plurality of probes with the one or more cell samples; (c) identifying one or more descriptive features for each cell sample; (d) determining one or more scores for each cell sample based upon the presence, absence, or quantity of descriptive features; and (e) compiling the scores for each subject.

A method of classifying gastrointestinal tract tissues, comprising: determining, testing, calculating, or assessing a biomarker expression profile of each cell sample; and classifying the cells in clusters determined by similarity of biomarker expression profile. In some embodiments, the method of classifying gastrointestinal tract tissues comprises determining a biomarker expression profile by using a kit described herein.

A method of determining, testing, calculating, or assessing patient responsiveness to a therapy for gastrointestinal tract disorders comprising:
(a) providing a plurality of a cell sample;
(b) contacting a plurality of probes with the cell sample;
(c) identifying one or more descriptive features;

(d) determining one or more scores based upon the presence, absence, or quantity of descriptive features; and (e) predicting patient responsiveness to a therapy to treat or prevent a gastrointestinal disorder based upon the score.

The invention also relates to a method of monitoring differentiation, morphology, or tumor progression of subject comprising: providing two or more cell samples from said subject; determining an expression profile of each of the cell samples; classifying the cell samples into clusters determined by similarity of biomarker expression profile; ordering the clusters by similarity of biomarker expression profile; and determining a time course of biomarker expression levels for each of the plurality of biomarkers at different stages of differentiation, morphology, or tumor progression in the cell samples. In some embodiments, the method of comprises determining an expression profile using a kit described herein.

The invention also relates to a method for identifying differentially expressed biomarkers, comprising: determining a biomarker expression profile of each of a set of cell samples at different differentiation, morphology, or tumor stages; classifying the cells in clusters determined by similarity of biomarker expression profile; ordering the clusters by similarity of biomarker expression profile; and determining a time course of biomarker levels for each of the plurality of biomarkers at different stages of differentiation, morphology, or tumor stages in the cell samples; and identifying differentially expressed biomarkers. In some embodiments, the method of identifying differentially expressed biomarkers comprises using a kit described herein.

The invention also relates to a method of identifying a specific cell type within a cell sample that contains a plurality of cells comprising: determining a biomarker expression profile of a plurality of cells; classifying the plurality of cells in clusters determined by similarity of biomarker expression profile; and determining the nature and function of the plurality of cells. In some embodiments, the method of identifying a specific cell type within a cell sample that contains a plurality of cells comprises using a kit described herein.

Also described herein is a method for predicting Barrett's esophagus in a subject, including: obtaining a cell sample from the subject, wherein the sample includes a plurality of analytes; contacting the cell sample with a probe and/or dye or a probe set; generating a plurality of complexes between the probe and/or probe set and the plurality of analytes; detecting the presence, absence, quantity, or spatially distribution of the plurality of complexes to obtain a dataset of descriptive features associated with the cell sample, wherein the first dataset includes quantitative expression data for at least one biomarker set selected from the group consisting of the marker sets in term 1, term 2, term 3, and optionally term 4, and optionally term 5, and optionally term 6, and optionally term 7; wherein terms 1 through terms 7 any combination of one or more biomarkers selected from the following: p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha; and determining a score from the dataset using an interpretation function, wherein the score is predictive of Barrett's esophagus in the subject.

Kits

The invention also relates to a kit comprising (a) a set of probes including one or a plurality of probes for determining a dataset associated with descriptive feature or features for at least one biomarker from a cell sample obtained from the subject; and (b) instructions for using the one probe or plurality of probes to determine one or more descriptive features from the cell sample; and, optionally, (c) software stored in a computer-readable format (such as a hard drive, flash drive, CD, DVD, disk, diskette, etc.) to convert any one or more descriptive features into a score. In some embodiments, the invention relates to a kit comprising (a) a set of probes including one or a plurality of probes for determining a dataset associated with descriptive feature or features for at least one biomarker from a cell sample obtained from the subject; and (b) software stored in a computer-readable format to convert any one or more descriptive features into a score.

The invention also relates to a kit for the prognosis of a particular clinical outcome of Barrett's esophagus comprising: (a) a set of probes including one or a plurality of probes for determining a dataset associated with descriptive feature or features for at least one biomarker from a cell sample obtained from the subject; and (b) instructions for using the one probe or plurality of probes to determine one or more descriptive features from the cell sample, wherein the instructions include instructions for determining a score from the dataset wherein the score is predictive of a particular clinical outcome of Barrett's esophagus in the subject. In some embodiments, the invention relates to a kit for the prognosis of a particular clinical outcome of Barrett's esophagus comprising: (a) a set of probes including one or a plurality of probes for determining a dataset associated with descriptive feature or features for at least one biomarker from a cell sample obtained from the subject and chosen from the following: p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL, HIF-1alpha; epithelial cells, multilayered-epithelial cells, endothelial cells, peripheral mononuclear lymphocytes, T cells, B cells, natural killer cells, eosinophils, stem cells, mast cells, macrophages, dendritic cells, neutrophils, fibroblasts, goblet cells, dysplastic cells, non-goblet columnar epithelial cells, 9p21, 8q24.12-13, or centromeres; and (b) instructions for using the one probe or plurality of probes to determine one or more descriptive features from the cell sample, wherein the instructions include instructions for determining a score from the dataset wherein the score is predictive of a particular clinical outcome of Barrett's esophagus in the subject.

In some embodiments, the invention relates to a kit for the prognosis of a particular clinical outcome of Barrett's esophagus comprising: (a) a set of probes including one or a plurality of probes for determining a dataset associated with descriptive feature or features for at least one biomarker from a cell sample obtained from the subject and chosen from the following: p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL, HIF-1alpha; epithelial cells, multilayered-epithelial cells, endothelial cells, peripheral mononuclear lymphocytes, T cells, B cells, natural killer cells, eosinophils, stem cells, mast cells, macrophages, dendritic cells, neutrophils, fibroblasts, goblet cells, dysplastic cells, non-goblet columnar epithelial cells, 9p21, 8q24.12-13, 17q11.2-q12, or centromeres; and (b) instructions for using the one probe or plurality of probes to determine one or more descriptive features from the cell sample, wherein the instructions include instructions for determining a score from the dataset wherein the score is predictive of a particular clinical outcome of Barrett's esophagus in the subject.

In another embodiment, the invention relates to a kit for determining a risk of progression of Barrett's esophagus in a subject comprising: a) one or more probes that is capable of detecting at least two or more biomarkers from the group consisting of p53, HIF-1alpha, beta-catenin, and COX-2; and b) instructions for using the probes to determine one or more descriptive features to generate a score from a cell and/or tissue sample of a subject. In another embodiment, the kit further comprises probes that are capable of detecting at least one or more biomarkers detected are selected from the group consisting of p16, Ki-67, alpha-methylacyl-CoA racemase (AMACR, P504S), matrix metalloproteinase 1, CD1a, NF-kappa-B, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, and FasL. In another embodiment, the kit further comprises probes that are capable of detecting at least one or more biomarkers selected from the group consisting of AMACR, CD1a, CD45RO, CD68, CK-20, Ki-67, NF-κB, and p16. In another embodiment, the score is predictive of the clinical outcome of Barrett's esophagus in the subject and/or diagnostic of the subclass of Barrett's esophagus in the subject. In another embodiment, the probes comprise antibody probes that specifically bind to said biomarkers. In another embodiment, the probes are fluorescent and/or comprise a fluorescent tag. In another embodiment, at least 10, at least 20, at least 30, at least 40, at least 50, or 60 descriptive features are determined from Tables 4. In another embodiment, at least 10, at least 20, at least 30, at least 40, at least 50, at least 60, at least 70, at least 80, or 89 descriptive features are determined from Table 5. In another embodiment, the score is predictive of the clinical outcome of Barrett's esophagus in the subject and/or diagnostic of the subclass of Barrett's esophagus in the subject. In another embodiment, the probes comprise antibody probes that specifically bind to said biomarkers. In another embodiment, the probes are fluorescent and/or comprise a fluorescent tag.

The invention also relates to a kit for the diagnosis of a particular subclass of Barrett's esophagus comprising: (a) a set of probes including one or a plurality of probes for determining a dataset associated with descriptive feature or features for at least one biomarker from a cell sample obtained from the subject; and (b) instructions for using the one probe or plurality of probes to determine one or more descriptive features from the cell sample, wherein the instructions include instructions for determining a score from the dataset wherein the score is predictive of a diagnosis of the subject for a subclass of Barrett's esophagus. In some embodiments, the invention relates to a kit for the diagnosis of a particular subclass of Barrett's esophagus comprising: (a) a set of probes including one or a plurality of probes for determining a dataset associated with descriptive feature or features for at least one biomarker from a cell sample obtained from the subject and chosen from the following: p16, p53, Ki-67, beta-catenin, alpha-methylacyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL, HIF-1alpha; epithelial cells, multilayered-epithelial cells, endothelial cells, peripheral mononuclear lymphocytes, T cells, B cells, natural killer cells, eosinophils, stem cells, mast cells, macrophages, dendritic cells, neutrophils, fibroblasts, goblet cells, dysplastic cells, non-goblet columnar epithelial cells, 9p21, 8q24.12-13, 17q11.2-q12, or centromeres; and (b) instructions for using the one probe or plurality of probes to determine one or more descriptive features from the cell sample, wherein the instructions include instructions for determining a score from the dataset wherein the score is predictive of a diagnosis of the subject for a subclass of Barrett's esophagus. The invention comprises kits for the diagnosis of a particular clinical outcome. In another embodiment, the score is predictive of the clinical outcome of Barrett's esophagus in the subject and/or diagnostic of the subclass of Barrett's esophagus in the subject. In another embodiment, the probes comprise antibody probes that specifically bind to said biomarkers. In another embodiment, the probes are fluorescent and/or comprise a fluorescent tag.

In another embodiment, the invention relates to a kit for classifying Barrett's esophagus in a subject, comprising: a) one or more probes that is capable of detecting at least two or more biomarkers from the group consisting of HIF-1alpha, p53, CD45RO, p16, AMACR, CK-20, CDX-2, HER2, CD1a, COX-2, NF-κB, Ki-67, CD-68, Beta-catenin, and nucleic acid; and b) instructions for using the probes to determine one or more descriptive features to generate a score from a cell and/or tissue sample of a subject.

In another embodiment, the kit further comprises probes that are capable of detecting at least one or more biomarkers selected from the group consisting of Ki-67, beta-catenin, matrix metalloproteinase 1, CD68, CD4, forkhead box P3, thrombospondin-1, C-myc, fibroblast activation protein alpha, cyclin D1, EGFR, Interleukin-6, PLAU plasminogen activator urokinase (uPA), Fas, and FasL. In another embodiment, at least 10, at least 20, at least 30, at least 40, at least 50, at least 60, at least 70, or 71 descriptive features are determined from Table 6. In another embodiment, the score is predictive of the clinical outcome of Barrett's esophagus in the subject and/or diagnostic of the subclass of Barrett's esophagus in the subject. In another embodiment, the probes comprise antibody probes that specifically bind to said biomarkers. In another embodiment, the probes are fluorescent and/or comprise a fluorescent tag.

Also described herein is a kit for predicting the responsiveness to a therapy for treating or preventing Barrett's esophagus or a gastrointestinal disorder in a subject, comprising: (a) a set of probes including a plurality of probes for determining a dataset from a cell sample obtained from the subject for at least two biomarkers selected from the group consisting of p16, p53, Ki-67, beta-catenin, alpha-methyl-acyl-CoA racemase (AMACR, P504S), matrix metalloproteinase 1, CD1a, NF-kappa-B p65, cyclo-oxygenase-2, CD68, CD4, forkhead box P3, CD45, thrombospondin-1, C-myc, cytokeratin-20, fibroblast activation protein alpha, cyclin D1, HER2/neu, EGFR, Interleukin-6, PLAU plasminogen activator urokinase (uPA), CDX2, Fas, FasL and HIF-1alpha; and (b) instructions for using the plurality of probes to determine the dataset from the sample, wherein the instructions include instructions for determining a score from the dataset, wherein the score is predictive of a subject's responsiveness a therapy.

All of the aforementioned kits may optionally comprise any probe, dye, or set of probes and/or dyes specific for an analyte that corresponds to the presence, absence, quantity, or spatial distribution of the of one or more of the following cell types: epithelial cells, multilayered-epithelial cells, endothelial cells, peripheral mononuclear lymphocytes, T cells, B cells, natural killer cells, eosinophils, stem cells, mast cells, macrophages, dendritic cells, neutrophils, fibroblasts, goblet cells, dysplastic cells, and non-goblet columnar epithelial cells. Biomarkers or analytes associated to each cell type are known throughout the art.

All of the aforementioned kits may optionally comprise any probe, dye, or set of probes and/or dyes specific for a chromosomal feature that corresponds to the presence, absence, quantity, or spatial distribution of one or more of the following chromosomal features: 9p21, 8q24.12-13, 17q11.2-q12, or centromeres.

All of the aforementioned kits may optionally comprise software stored in a computer-readable format (such as a hard drive, flash drive, CD, DVD, disk, diskette, etc.) to convert any one or more descriptive features into a score.

Although the present invention has been described in connection with certain specific embodiments for instructional purposes, the present invention is not limited thereto. For example, although embodiments of the analysis system and computer-implemented network structure have been described above in relation to the computer-aided detection of certain biomarkers or subcellular organelles, the analysis system and network structure can equally be applied to detecting and analyzing target patterns in digital imagery of other spatially positioned objects on a digital image. For example, the analysis system can be used to detect and analyze anatomical regions of subcellular compartments, as well as the frequency of different spatially positioned regions of an image. When analyzing cell samples depicted in digital images captured from photographic microscopes, thematic classes can be assigned to pixel locations that represent probed or un-probed cellular structures or biomaterials. Accordingly, various modifications, adaptations, and combinations of various features of the described embodiments can be practiced without departing from the scope of the invention as set forth in the claims. Any and all journal articles, patent applications, issued patents, or other cited references are incorporated by reference in their entirety.

Example 1

Development of Tests to Predict Risk for Esophageal Adenocarcinoma in Patients with Barrett's Esophagus.

Project Goal: Develop a diagnostic and prognostic test or tests for Barrett's Esophagus predicting risk of developing esophageal cancer.

Clinical Need for Test: More than 339,000 upper GI biopsies are performed in the US annually, and risk stratification is difficult for clinicians. Approximately 50% of patients first diagnosed with Esophageal Cancer (13,000 new cases/year in the US) are negative for dysplasia on their previous endoscopy procedure, which means many patients at risk for cancer are simply missed by current endoscopic surveillance. Furthermore, many biopsy results for Barrett's are reported as indefinite, leading to uncertainty in risk for developing cancer.

Indicated Use for Test: Patients undergoing endoscopy suspected of having Barrett's Esophagus, and for which biopsy material will be available for analysis. Actionable Result: Classifier will identify patients at low, high, or intermediate risk for esophageal cancer. Physician responsible for care can determine if procedure such as Radio Frequency Ablation (RFA), Endoscopic Mucosal Resection (EMR), or other treatment method should be applied.

Assay Optimization and Build Training Patient Cohort

The multiplexed fluorescence staining conditions that produce optimal signal:noise and correct staining pattern for 14 protein biomarkers (Table 2) were determined. Image analysis algorithms were developed to i) identify individual biopsy sections on slides containing multiple biopsies, ii) remove autofluorescence from digital images of esophageal tissue sections, iii) segment individual nuclei, cytoplasms and plasma membranes in digital images of esophageal tissue sections, iv) segment surface epithelium and glands from stroma in digital images of esophageal tissue sections and v) extract quantitative biomarker features from subcellular compartments (nuclei, cytoplasm, plasma membrane) and tissue compartments (epithelium, glands, stroma). Example images of biomarkers in esophageal tissues and image analysis masks are shown in Phase 2, below.

TABLE 2

Diagnostic-Prognostic Biomarker Panel

| Biomarker Category | Biomarker |
|---|---|
| Epithelial/ Tumor Biomarkers | Cytokeratin-20 (CK-20) |
| | CDX-2 |
| | p53 |
| | p16 |
| | Ki-67 |
| | Beta-catenin |
| | α-methylacyl coenzyme A racemase (AMACR) |
| | HER/neu |
| Immune Biomarkers | CD68 |
| | CD45RO |
| | CD1a |
| Stromal/ Inflammatory Biomarkers | HIF-1 alpha |
| | Nuclear factor kappa B p65 (NF-κB) |
| | Cyclooxygenase 2 (COX-2) |

Training Cohort

The training cohort analyzed so far is described in Table 3. The training cohort is being expanded to include cases from approximately 200 cases.

TABLE 3

Summary of Training Cohort

| Diagnostic Subcategory | Number of Cases | Prognostic Subcategory | Number of Cases |
|---|---|---|---|
| Barrett's esophagus, no dysplasia | 17 | No progression | 7 |
| | | Progression to LGD | 8 |
| | | Progression to HGD/EAC | 2 |
| Barrett's esophagus, reactive atypia | 14 | No progression | 6 |
| | | Progression to LGD | 4 |
| | | Progression to HGD/EAC | 4 |
| Barrett's esophagus, indefinite for dysplasia | 14 | No progression | 5 |
| | | Progression to LGD | 5 |
| | | Progression to HGD/EAC | 4 |

TABLE 3-continued

Summary of Training Cohort

| Diagnostic Subcategory | Number of Cases | Prognostic Subcategory | Number of Cases |
|---|---|---|---|
| Barrett's esophagus, low grade dysplasia | 16 | No progression | 7 |
|  |  | Progression to LGD | 1 |
|  |  | Progression to HGD/EAC | 8 |
| Barrett's esophagus, high grade dysplasia | 11 | n/a | 11 |
| Esophageal Adenocarcinoma | 6 | n/a | 6 |
| Total Number of Cases | 78 |  |  |

No progression: patients who did not progress from no dysplasia, reactive atypia or indefinite for dysplasia to low grade dysplasia (LGD), high grade dysplasia (HGD) or esophageal adenocarcinoma (EAC)
Progression to LGD: patients who progressed from no dysplasia, reactive atypia or indefinite for dysplasia to low grade dysplasia and patients who had multiple diagnoses of low grade dysplasia
Progression to HGD/EAC: patients who presented with high grade dysplasia and patients who progressed from no dysplasia, reactive atypia, indefinite for dysplasia or low grade dysplasia to high grade dysplasia or esophageal adenocarcinoma Training Study to Evaluate the Diagnostic and Prognostic Significance of the Test and to Develop Diagnostic and Prognostic Classifiers The 14 protein biomarkers and morphology described in Table 2 have been evaluated in the initial training cohort of 78 patients in Table 3.

Methods: Multiplexed Fluorescence Biomarker Labeling and Imaging in Esophageal Tissues Glass slides were prepared with 5 micrometer thick sections of formalin-fixed, paraffin-embedded esophageal biopsies. Slides were baked at 60° C. for 30 minutes to melt paraffin and immersed in Aqua DePar (Biocare Medical) for 10 minutes at 75° C. to remove paraffin from tissue sections. Slides were then immersed in antigen retrieval buffer (1 mM EDTA 10 mM Tris 0.05% Tween 20, pH9) at 99° C. for 20 minutes followed by room temperature for 20 minutes. Slides were washed twice for 5 minutes each wash in tris-buffered saline 0.025% Tween 20 at room temperature and then Image-iT FX signal enhancer (Invitrogen) was applied for 30 minutes at room temperature. The signal enhancer was replaced with blocking buffer and slides were incubated for 30 minutes at room temperature.

Blocking buffer was then replaced with a cocktail of 3 primary antibody cocktails as follows for each subpanel:

Subpanel 1: rabbit IgG anti-Ki-67, mouse IgG2a anti-cytokeratin-20, mouse IgG1 anti-beta-catenin;
Subpanel 2: rabbit IgG anti-AMACR, mouse IgG2a anti-p16, mouse IgG2b p53;
Subpanel 3: rabbit IgG anti-COX2, mouse IgG3 anti-CD68, mouse IgG1 anti-NFkB p65;
Subpanel 4: rabbit IgG anti-HIF-1alpha, mouse IgG2a anti-CD45RO, mouse IgG1 anti-CD1a;
Subpanel 5: rabbit IgG anti-HER2, mouse IgG2a anti-cytokeratin-20, mouse IgG1 anti-CDX-2.

Slides were incubated with the primary antibody cocktails for 1 hour at room temperature.

Slides were then washed thrice for 4 minutes each wash in tris-buffered saline 0.025% Tween 20 and blocking buffer was re-applied. Blocking buffer was replaced with a fluorophore-conjugated species-specific, isotype-specific secondary antibody cocktail for each subpanel as follows: Subpanel 1: Alexa Fluor 488-goat anti-rabbit IgG, Alexa Fluor 555-goat anti-mouse IgG2a, Alexa Fluor 647-goat anti-mouse IgG1; Subpanel 2: Alexa Fluor 488-goat anti-rabbit IgG, Alexa Fluor 555-goat anti-mouse IgG2a, Alexa Fluor 647-goat anti-mouse IgG2b; Subpanel 3: Alexa Fluor 488-goat anti-mouse IgG3, Alexa Fluor 555-goat anti-mouse IgG1, Alexa Fluor 647-goat anti-rabbit IgG; Subpanel 4: Alexa Fluor 488-goat anti-rabbit IgG, Alexa Fluor 555-goat anti-mouse IgG2a, Alexa Fluor 647-goat anti-mouse IgG1; Subpanel 5: Alexa Fluor 488-goat anti-rabbit IgG, Alexa Fluor 555-goat anti-mouse IgG2a, Alexa Fluor 647-goat anti-mouse IgG1. Slides were incubated with the secondary antibody cocktails for 1 hour at room temperature.

Slides were washed thrice for 4 minutes each wash in tris-buffered saline and then 10 mg/ml Hoechst 33342 (diluted in deionized water) was applied to the slides for 3 minutes followed by washing in deionized water for 3 minutes. Slides were then air-dried and mounted with coverslips using Prolong Gold Antifade medium (Invitrogen). Additional serial sections were also stained with Hematoxylin and Eosin using standard histology methods.

Fluorescently-stained slides were scanned at 20× magnification on a ScanScope FL with a DAPI/FITC/TRITC/Cy5 quadband filter (Aperio Technologies, Vista, CA). Optimal exposure times were determined for each biomarker panel and the same exposure settings for each biomarker panel were applied to all slide scans. Example digital images of each fluorescent channel for biomarker subpanels 1-5 are shown in FIGS. 4-8. Hematoxylin and Eosin-stained slides were scanned at 20× on NanoZoomer Digital Pathology slide scanner (Hamamatsu Corporation, K.K., Japan).

Image Analysis to Extract Quantitative Biomarker Data

Figure 9:
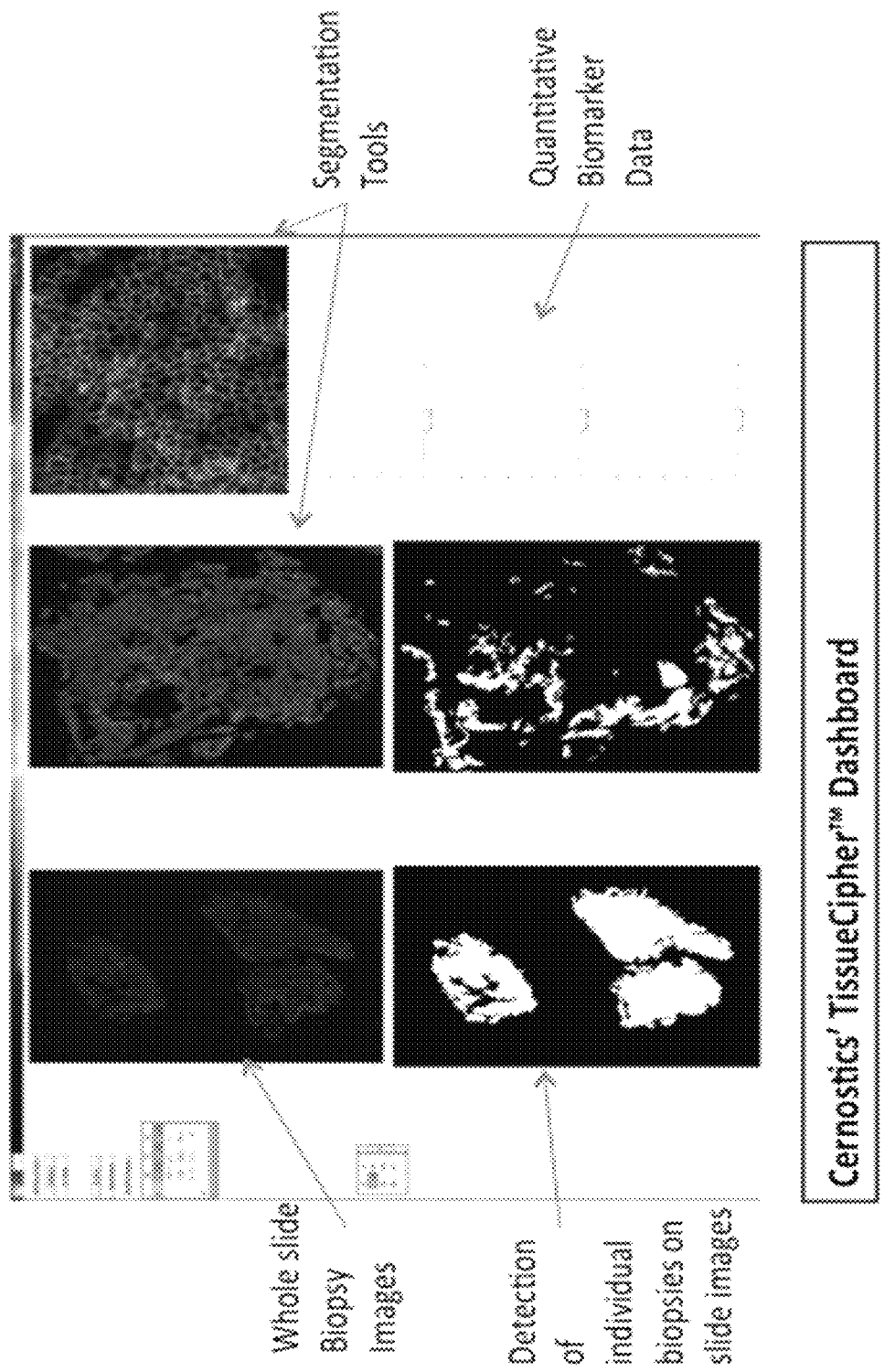
FIG. 9 depicts a Dashboard for Digital Tissue Image Segmentation and Data Extraction.

Image analysis was performed on whole slide digital images of Barrett' esophagus biopsies using Matlab software to develop specific image analysis algorithms. These algorithms were developed by Cernostics. The Cernostics image processing workflow consists of the following components: image detection, image validation, low order image object segmentation, feature measurement, and high order image object segmentation. A screenshot of Cernostics' dashboard for image processing, segmentation and data extraction is shown in FIG. 9. Image detection consists of an algorithm for automatic detection of tissue sections in the whole slide image. Each tissue section has auto-fluorescence from erythrocytes removed by an automated detection algorithm. Each tissue section is then submitted to a nuclei detection algorithm, which is in turn used to estimate cell cytoplasm. A plasma membrane mask is calculated for markers known to express in the plasma membrane. Cell, nuclei, and plasma membrane image masks are then used to calculate image object features which consist of morphological shape measurements, marker expressions in the different cell compartments, and ratios of marker expressions in the different cell compartments. The x-y coordinates of each image object feature is recorded to enable spatial analyses of biomarker expression. For each tissue section higher order masks to identify gland, epithelium, stroma, and inflammation are calculated. Patterns of marker expression are then localized to these higher order image objects. The image analysis calculates the mean intensity of each biomarker in each cell or cell compartment. The single cell distribution is summarized for each patient case in the indicated percentiles. Comparison of quantiles between diagnostic classes and risk classes is more sensitive than comparing means in detecting samples with over-expression or loss of expression of biomarkers in small numbers of cells. Example image analysis masks are shown in FIG. 10.

Figure 10:
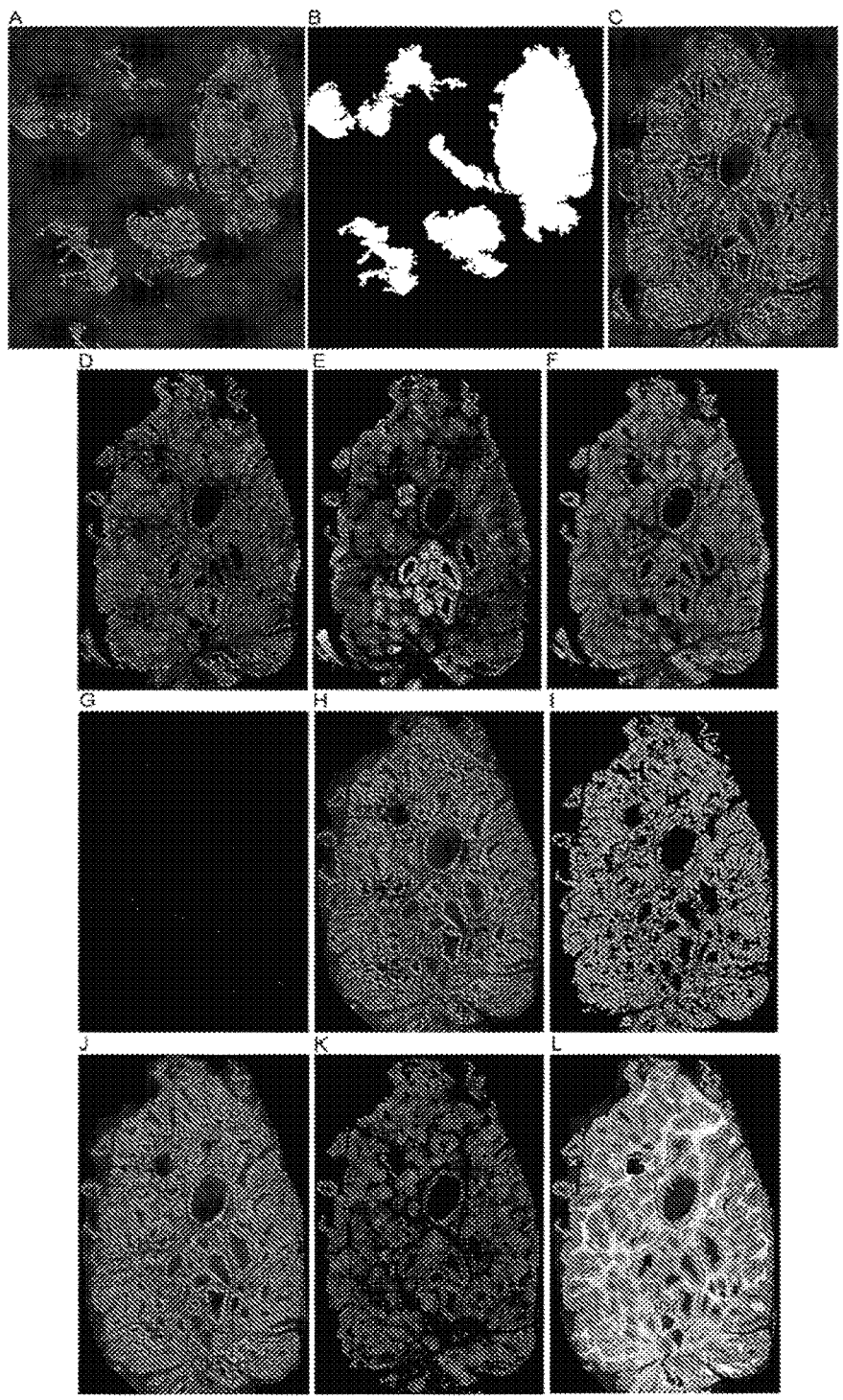
FIG. 10 depicts Four Channel Fluorescence Biomarker Images and Image Segmentation for Quantitative Biomarker and Morphology Analysis.

In FIG. 10, an esophageal biopsy slide stained for Subpanel 1 (Hoechst, Ki-67-Alexa Fluor 488, CK-20-Alexa Fluor 555, Beta-catenin-Alexa Fluor 647) was scanned at 20× magnification (A). Image analysis was applied to identify and segment individual biopsies on the slide (B). Whole biopsy images of the upper right biopsy are shown in the four fluorescence channels C: Hoechst, D: Ki-67, E: CK-20, F: Beta-catenin. Image analysis was used to identify and remove autofluorescence (G), apply a nuclear edge mask (H), nuclear area mask (I), cell mask (J), plasma membrane mask (K) and gland and stroma masks (L).

Statistical Analyses: Prognostic Significance—Stratifying Cases According to Risk of Progressing to LGD, HGD or EAC 276 features (mean intensity in cells or cell compartments, ratios of one biomarker intensity between two cell compartments, ratios of two biomarkers between one or two cell compartments, nuclear size, shape and intensity) were screened one at a time by logistic regression to produce a univariate ranking of features that are significantly different between non-progressors and progressors. 60 features with a p-value≤0.05 in the comparison of No Progression cases versus Progression to HGD/EAC cases are summarized in Table 4. The statistically significant features in Table 4 are derived from the following biomarkers: AMACR, Beta-catenin, CD1a, CD45RO, CD68, COX2, HIF1alpha, Ki-67, NF-κB, p16, p53. 89 features with a p-value≤0.05 in the comparison of No Progression cases versus Progression to LGD and Progression to HGD/EAC case are summarized in Table 5. The statistically significant features in Table 5 are derived from the following biomarkers: AMACR, Beta-catenin, CD1a, CD45RO, CD68, CK-20, COX2, HIF1alpha, Ki-67, NF-κB, p16, p53.

The top 50 features were selected and entered into a stepwise logistic regression procedure. The best model was chosen using Akaike's information criterion. The resulting linear predictor utilizes the following features:
  p53 cellular mean intensity 99th percentile
  HIF-1alpha cellular mean intensity 99th percentile
  Beta-catenin cell mean intensity 5th percentile
  COX2 plasma membrane: nucleus ratio 50th percentile The features represent tumor/epithelial, inflammation and angiogenesis processes in the Barrett's esophagus tissue system.

Figure 11:
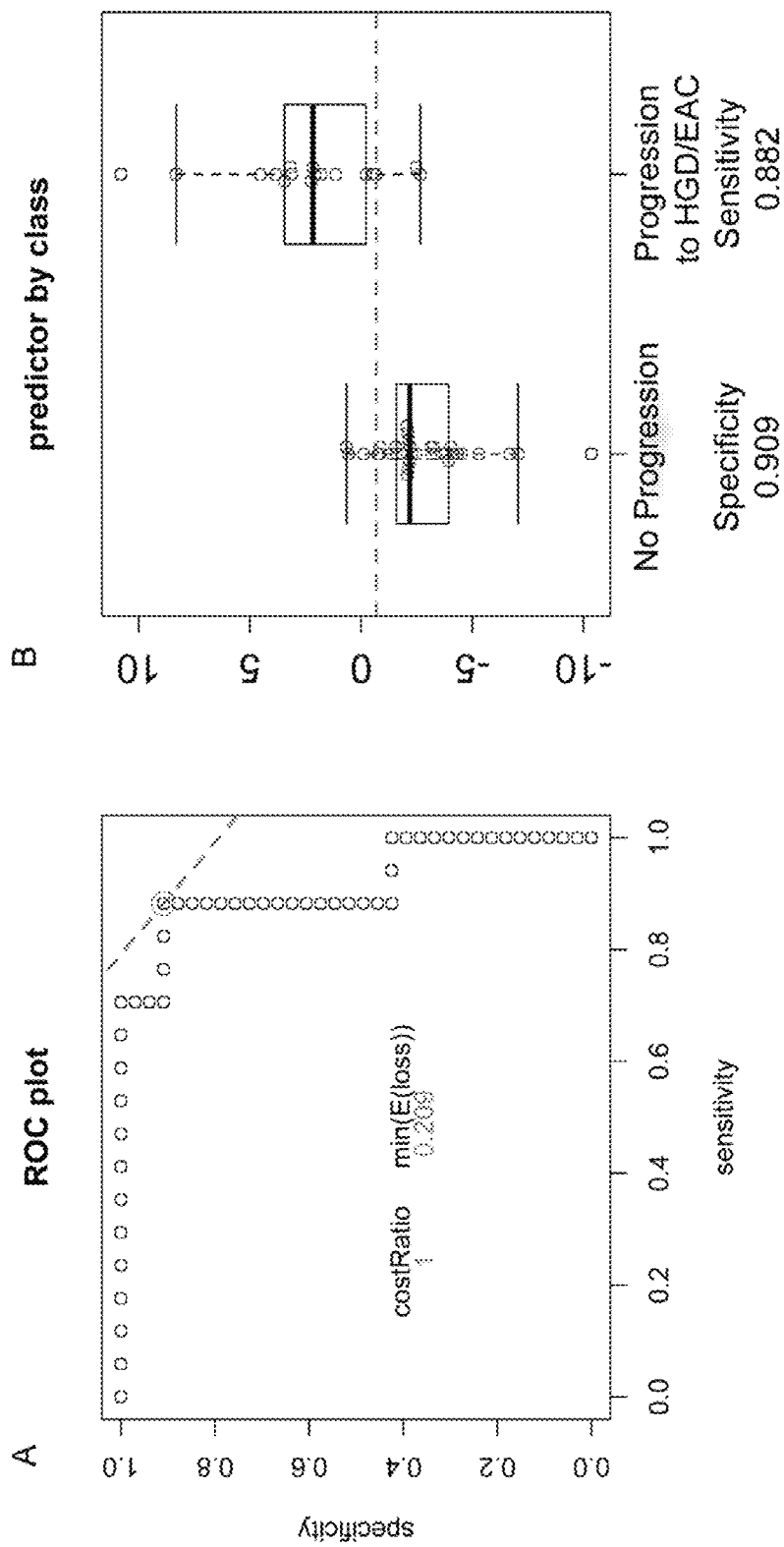
FIG. 11 depicts Receiver Operator Characteristics Curve Plot and Box Plot for Multivariate Predictive Classifier to Stratify No Progressors from Progressors to HGD/EAC.

A Receiver Operating Characteristics (ROC) curve for the multivariate predictor and box plots are shown in FIG. 11 with an example cutoff that produces 90.9% specificity and 88.2% sensitivity in stratifying the no progression group and the progression to HGD/EAC group. In FIG. 11, the top 50 features from a univariate ranking of features to discriminate "no progression" cases from "progression to HGD/EAC" cases were selected and entered into a stepwise logistic regression procedure. The best model was chosen using Akaike's information criterion. The ROC plot (left) shows the sensitivity and specificity as a function of prognostic threshold. The larger circle and dotted line and the table insert show the result of an example decision analysis optimizing the trade-off between false-positives and false-negatives. The cost ratio is 1 and the prevalence odds ratio is 1. The plot on the right shows box plots for the linear predictor with the dotted line at an example cutoff that produces 90.9% specificity and 88.2% sensitivity. The no progression group consists of patients who did not progress to any type of dysplasia or cancer. The Progression to HGD/EAC group consists of Barrett's esophagus with low grade dysplasia, no dysplasia, reactive atypia or indefinite for dysplasia who progressed to high grade dysplasia or esophageal adenocarcinoma.

Figure 12:
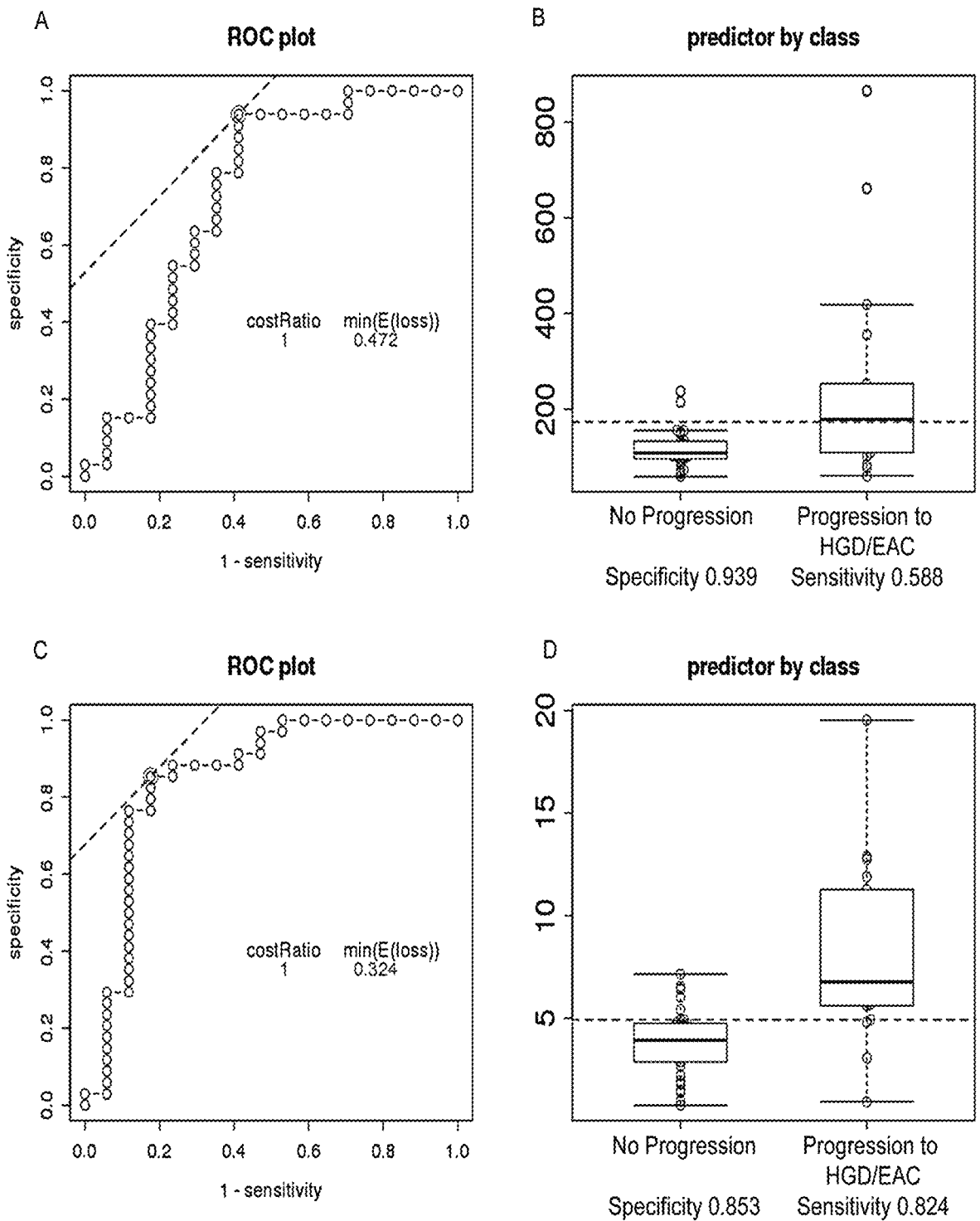
FIG. 12 depicts Receiver Operator Characteristics Curves and Box Plots for Example Univariate Predictive Features to Stratify No Progressors from Progressors to HGD/EAC.

ROC curves and box plots for the top two features by univariate ranking (p53 and HIF1-alpha:CD1a) are shown in FIG. 12. In FIG. 12, the ROC plots show the sensitivity and specificity for p53 (A) and HIF1-alpha:CD1a ratio (C) as a function of predictive threshold. The larger circle and dotted line and the table insert show the result of an example decision analysis optimizing the trade-off between false-positives and false-negatives. The cost ratio is 1 and the prevalence odds ratio is 1. Plots B and D show box plots for the linear predictors with the dotted line at an example cutoff that produces 93.9% specificity and 58.8% sensitivity for p53 and 85.3% specificity and 82.4% sensitivity for HIF1-alpha:CD1a ratio. The no progression group consists of patients who did not progress to any type of dysplasia or cancer. The Progression to HGD/EAC group consists of Barrett's esophagus with low grade dysplasia, no dysplasia, reactive atypia or indefinite for dysplasia who progressed to high grade dysplasia or esophageal adenocarcinoma. P values after Bonferroni adjustment are 0.0128 for p53 and 0.0017 for HIF1alpha-CD1a.

Diagnostic Significance—Stratifying Cases According to Sub-Diagnosis/Classification of Barrett's Esophagus 205 features (mean intensity in cells or cell compartments, ratios of one biomarker intensity between two cell compartments, ratios of two biomarkers between one or two cell compartments, nuclear size, shape and intensity) were screened one at a time by logistic regression to produce a univariate ranking of features that are significantly different between Barrett's esophagus cases with no dysplasia or reactive atypia versus Barrett's esophagus cases with low grade dysplasia or high grade dysplasia. Table 6 summarizes the 71 features that had a p value of ≤0.05 in this analysis. The statistically significant features described in Table 6 are derived from the following biomarkers and morphometrics: nuclei area, nuclei equivalent diameter, nuclei solidity, nuclei eccentricity, DNA (Hoechst) intensity, HIF1alpha, p53, CD45RO, p16, AMACR, CK-20, CDX-2, HER2, CD1a, COX-2, NF-κB.

Table 7 lists significant diagnostic and prognostic biomarker features and subcellular localizations.

TABLE 4

Univariate Ranking of P Values from Logistic Regression of No Progression Cases versus Progression to HGD/EAC Cases.

| Feature Name (with percentile) | Estimate | Std. Error | z value | Pr(>\|z\|) (p value from linear regression (Wald test) | Effect | CI-lower (for effect) | CI-upper (for effect) | Pvalue_LR (deviance/ likelihood ratio p value) |
|---|---|---|---|---|---|---|---|---|
| HIF1alpha membrane:CD1a nucleus ratio 0.99 | 0.650 | 0.218 | 2.976 | 0.003 | 1.915 | 1.248 | 2.938 | 0.0000042 |
| p53 Nuclei mean intensity 0.99 | 0.014 | 0.005 | 2.859 | 0.004 | 1.014 | 1.004 | 1.024 | 0.0000305 |
| p53 Cytoplasm mean Intensity 0.99 | 0.014 | 0.005 | 2.478 | 0.013 | 1.014 | 1.003 | 1.025 | 0.0001976 |

TABLE 4-continued

Univariate Ranking of P Values from Logistic Regression of No Progression
Cases versus Progression to HGD/EAC Cases.

| Feature Name (with percentile) | Estimate | Std. Error | z value | Pr(>\|z\|) (p value from linear regression (Wald test) | Effect | CI-lower (for effect) | CI-upper (for effect) | Pvalue_LR (deviance/ likelihood ratio p value) |
|---|---|---|---|---|---|---|---|---|
| p53 Cell mean intensity 0.99 | 0.015 | 0.006 | 2.374 | 0.018 | 1.015 | 1.003 | 1.028 | 0.0003323 |
| HIF1alpha Nuclei mean intensity 0.99 | 0.020 | 0.007 | 2.661 | 0.008 | 1.020 | 1.005 | 1.035 | 0.0007769 |
| p53 Nuclei mean Intensity 0.95 | 0.016 | 0.008 | 2.091 | 0.037 | 1.016 | 1.001 | 1.032 | 0.0009684 |
| CD1a Cell mean intensity 0.01 | −0.289 | 0.102 | −2.837 | 0.005 | 0.749 | 0.613 | 0.914 | 0.0011908 |
| CD1a Cytoplasm_meanIntensity 0.01 | −0.233 | 0.081 | −2.874 | 0.004 | 0.792 | 0.676 | 0.929 | 0.0012823 |
| CD1a Cell mean intensity 0.05 | −0.207 | 0.078 | −2.661 | 0.008 | 0.813 | 0.697 | 0.947 | 0.0013442 |
| p53 AMACR_Cell_PlasmaNucRatio 0.99 | 0.349 | 0.142 | 2.465 | 0.014 | 1.418 | 1.074 | 1.872 | 0.0015026 |
| CD1a_Cytoplasm_meanIntensity 0.05 | −0.214 | 0.081 | −2.647 | 0.008 | 0.808 | 0.689 | 0.946 | 0.0015588 |
| HIF1alpha cytoplasm: CD1a membrane ratio 0.99 | 0.032 | 0.012 | 2.722 | 0.006 | 1.032 | 1.009 | 1.056 | 0.0018362 |
| p53 membrane: AMACR nucleus ratio 0.95 | 0.763 | 0.368 | 2.075 | 0.038 | 2.145 | 1.043 | 4.410 | 0.0020232 |
| CD1a Nuclei mean intensity 0.01 | −0.197 | 0.076 | −2.597 | 0.009 | 0.821 | 0.708 | 0.953 | 0.0036836 |
| CD1a Nuclei mean intensity 0.05 | −0.147 | 0.058 | −2.539 | 0.011 | 0.864 | 0.771 | 0.967 | 0.0039722 |
| HIF1alpha Cytoplasm mean intensity 0.99 | 0.022 | 0.009 | 2.432 | 0.015 | 1.022 | 1.004 | 1.040 | 0.0040797 |
| p53 Cytoplasm mean intensity 0.95 | 0.015 | 0.009 | 1.614 | 0.107 | 1.015 | 0.997 | 1.033 | 0.0042746 |
| p53_Cell_meanIntensity.0.95 | 0.016 | 0.009 | 1.708 | 0.088 | 1.016 | 0.998 | 1.034 | 0.0044423 |
| p53 cytoplasm: AMACR membrane ratio 0.99 | 0.017 | 0.008 | 2.197 | 0.028 | 1.017 | 1.002 | 1.033 | 0.0048921 |
| HIF1alpha Cell mean intensity 0.99 | 0.021 | 0.008 | 2.455 | 0.014 | 1.021 | 1.004 | 1.038 | 0.0049838 |
| CD68 Nuclei mean intensity 0.99 | 0.021 | 0.010 | 2.167 | 0.030 | 1.021 | 1.002 | 1.041 | 0.0052668 |
| NFKB cytoplasm: CD68 membrane ratio 0.01 | −1.032 | 0.451 | −2.289 | 0.022 | 0.356 | 0.147 | 0.862 | 0.0063369 |
| CD1a cytoplasm: CD45RO membrane 0.05 | −1.928 | 0.859 | −2.244 | 0.025 | 0.146 | 0.027 | 0.783 | 0.0071582 |
| AMACR membrane: P16 nucleus ratio 0.5 | 68.695 | 93.221 | −0.737 | 0.461 | 0.000 | 0.000 | 3.288E+49 | 0.0077902 |
| AMACR membrane: nucleus ratio 0.5 | 35.233 | 47.327 | −0.744 | 0.457 | 0.000 | 0.000 | 9.645E+24 | 0.0082491 |
| Beta-catenin Nuclei mean intensity 0.05 | −0.167 | 0.074 | −2.265 | 0.023 | 0.846 | 0.732 | 0.978 | 0.0085289 |
| HIF1alpha membrane: CD1a nucleus ratio 0.95 | 0.637 | 0.304 | 2.096 | 0.036 | 1.891 | 1.042 | 3.431 | 0.0091023 |
| Beta-catenin Cell mean intensity 0.01 | −0.269 | 0.121 | −2.221 | 0.026 | 0.765 | 0.603 | 0.969 | 0.0091937 |
| CD45RO cytoplasm: HIF1alpha membrane ratio 0.01 | −0.766 | 0.342 | −2.241 | 0.025 | 0.465 | 0.238 | 0.908 | 0.0094542 |
| P16 Cell mean intensity 0.01 | −0.099 | 0.045 | −2.210 | 0.027 | 0.906 | 0.830 | 0.989 | 0.0108643 |
| CD1a cytoplasm: CD45RO membrane ratio 0.01 | −3.866 | 1.844 | −2.097 | 0.036 | 0.021 | 0.001 | 0.777 | 0.0114551 |
| Beta-catenin Cell mean intensity 0.05 | −0.171 | 0.079 | −2.155 | 0.031 | 0.843 | 0.722 | 0.985 | 0.0115135 |
| NFKB cytoplasm: CD68 membrane ratio 0.05 | −0.393 | 0.199 | −1.973 | 0.048 | 0.675 | 0.457 | 0.997 | 0.0123236 |
| p53 cytoplasm: AMACR membrane 0.95 | 0.026 | 0.014 | 1.937 | 0.053 | 1.027 | 1.000 | 1.055 | 0.0154614 |
| CD68 cytoplasm mean intensity 0.99 | 0.019 | 0.009 | 2.100 | 0.036 | 1.019 | 1.001 | 1.037 | 0.0162049 |
| p53 cytoplasm:nuclear membrane ratio 0.01 | −1.159 | 0.559 | −2.074 | 0.038 | 0.314 | 0.105 | 0.938 | 0.0163040 |
| COX2 membrane: NFKB nucleus ratio 0.95 | 0.765 | 0.338 | 2.263 | 0.024 | 2.149 | 1.108 | 4.170 | 0.0179868 |
| CD68 cell mean intensity 0.99 | 0.019 | 0.010 | 1.962 | 0.050 | 1.019 | 1.000 | 1.039 | 0.0185398 |
| COX2 membrane:nucleus ratio 0.99 | 0.265 | 0.144 | 1.842 | 0.065 | 1.304 | 0.983 | 1.729 | 0.0210546 |

TABLE 4-continued

Univariate Ranking of P Values from Logistic Regression of No Progression Cases versus Progression to HGD/EAC Cases.

| Feature Name (with percentile) | Estimate | Std. Error | z value | Pr(>\|z\|) (p value from linear regression (Wald test) | Effect | CI-lower (for effect) | CI-upper (for effect) | Pvalue_LR (deviance/ likelihood ratio p value) |
|---|---|---|---|---|---|---|---|---|
| COX2 membrane:nucleus ratio 0.5 | 2.707 | 1.212 | 2.232 | 0.026 | 14.977 | 1.391 | 161.214 | 0.0216124 |
| Beta-catenin cytoplasm mean intensity 0.05 | −0.140 | 0.071 | −1.977 | 0.048 | 0.869 | 0.756 | 0.999 | 0.0217620 |
| COX2 cytoplasm: membrane ratio 0.01 | −1.467 | 0.815 | −1.801 | 0.072 | 0.231 | 0.047 | 1.138 | 0.0233622 |
| CD68 cytoplasm:membrane ratio 0.05 | −0.645 | 0.340 | −1.900 | 0.057 | 0.524 | 0.270 | 1.021 | 0.0244353 |
| CD45R0 membrane:HIF1alpha nucleus ratio 0.99 | 0.299 | 0.184 | 1.622 | 0.105 | 1.348 | 0.940 | 1.935 | 0.0250856 |
| AMACR cell mean intensity 0.01 | −0.240 | 0.127 | −1.887 | 0.059 | 0.787 | 0.613 | 1.009 | 0.0258754 |
| Beta-catenin nuclei mean intensity 0.01 | −0.147 | 0.074 | −1.980 | 0.048 | 0.863 | 0.747 | 0.999 | 0.0307526 |
| Ki67 nuclei mean intensity 0.99 | 0.009 | 0.004 | 2.036 | 0.042 | 1.009 | 1.000 | 1.018 | 0.0321749 |
| CD68 cytoplasm:membrane ratio 0.01 | −1.353 | 0.711 | −1.903 | 0.057 | 0.258 | 0.064 | 1.041 | 0.0325397 |
| Ki67 nuclear membrane: Beta-catenin nucleus ratio 0.5 | −1106.110 | 13441 9.988 | −0.008 | 0.993 | 0.000 | 0.000 | Inf | 0.0333813 |
| Ki67 nuclear membrane:total nucleus ratio 0.5 | −1609.207 | 17209 4.078 | −0.009 | 0.993 | 0.000 | 0.000 | Inf | 0.0333813 |
| HIF1alpha cytoplasm:CD1a membrane ratio 0.95 | 0.026 | 0.013 | 2.003 | 0.045 | 1.027 | 1.001 | 1.054 | 0.0343305 |
| COX2_Cell_CytoPlasmaRatio .0.05 | −0.596 | 0.368 | −1.617 | 0.106 | 0.551 | 0.268 | 1.135 | 0.0351331 |
| Beta-atenin cytoplasm mean intensity 0.01 | −0.132 | 0.070 | −1.888 | 0.059 | 0.876 | 0.764 | 1.005 | 0.0410004 |
| p53 Cell mean intensity 0.01 | −0.263 | 0.140 | −1.879 | 0.060 | 0.769 | 0.584 | 1.011 | 0.0426466 |
| COX2 membrane:nucleus ratio 0.95 | 0.889 | 0.459 | 1.937 | 0.053 | 2.432 | 0.990 | 5.980 | 0.0430243 |
| Ki67 nuclear membrane:total nucleus ratio 0.99 | −0.834 | 0.461 | −1.812 | 0.070 | 0.434 | 0.176 | 1.071 | 0.0459256 |
| COX2 membrane:NFKB nucleus ratio 0.5 | 3.248 | 1.696 | 1.915 | 0.055 | 25.746 | 0.927 | 714.915 | 0.0505738 |
| COX2 Cytoplasm:membrane ratio 0.5 | −0.054 | 0.029 | −1.872 | 0.061 | 0.947 | 0.895 | 1.003 | 0.0510762 |
| P16 Cytoplasm:membrane ratio 0.05 | 0.222 | 0.131 | 1.687 | 0.092 | 1.248 | 0.965 | 1.615 | 0.0510880 |
| p53 Cell mean intensity.0.05 | −0.159 | 0.091 | −1.750 | 0.080 | 0.853 | 0.714 | 1.019 | 0.0526574 |

TABLE 5

Univariate Ranking of P Values from Logistic Regression of No Progression Cases versus Progression to LGD and Progression to HGD/EAC Cases.

| Feature name (with percentile) | Estimate | Std. Error | z value | Pr(>\|z\|) (p value from linear regression (Wald test) | Effect | CI-lower (for effect) | CI-upper (for effect) | Pvalue_LR (deviance/ likelihood ratio p value) |
|---|---|---|---|---|---|---|---|---|
| p16 Cytoplasm:Plasma membrane Ratio 0.01 | 1.264 | 0.432 | 2.925 | 0.003 | 3.538 | 1.517 | 8.252 | 0.0003597 |
| p16 Cytoplasm:Plasma membrane Ratio 0.05 | 0.371 | 0.143 | 2.591 | 0.010 | 1.449 | 1.094 | 1.917 | 0.0006047 |
| AMACR cytoplasm: p16 Plasma membrane Ratio 0.05 | 0.726 | 0.278 | 2.609 | 0.009 | 2.066 | 1.198 | 3.565 | 0.0006340 |
| AMACR cytoplasm:p16Plasma membrane Ratio 0.01 | 2.183 | 0.779 | 2.802 | 0.005 | 8.869 | 1.927 | 40.826 | 0.0009991 |
| p53 Nuclei mean intensity 0.99 | 0.010 | 0.004 | 2.402 | 0.016 | 1.010 | 1.002 | 1.018 | 0.0011155 |
| CD1a cell mean intensity 0.05 | −0.160 | 0.057 | −2.824 | 0.005 | 0.852 | 0.763 | 0.952 | 0.0011196 |
| CD1a Nuclei mean intensity 0.05 | −0.129 | 0.045 | −2.848 | 0.004 | 0.879 | 0.804 | 0.961 | 0.0015972 |

TABLE 5-continued

Univariate Ranking of P Values from Logistic Regression of No Progression Cases versus Progression to LGD and Progression to HGD/EAC Cases.

| Feature name (with percentile) | Estimate | Std. Error | z value | Pr(>\|z\|) (p value from linear regression (Wald test) | Effect | CI-lower (for effect) | CI-upper (for effect) | Pvalue_LR (deviance/ likelihood ratio p value) |
|---|---|---|---|---|---|---|---|---|
| COX2 plasma membrane:NFKB nucleus Ratio 0.95 | 0.798 | 0.279 | 2.863 | 0.004 | 2.222 | 1.286 | 3.837 | 0.0019325 |
| CD1a Cell mean intensity 0.01 | −0.212 | 0.076 | −2.805 | 0.005 | 0.809 | 0.698 | 0.938 | 0.0019355 |
| p53 plasma membrane:AMACR nucleus Ratio 0.99 | 0.310 | 0.130 | 2.384 | 0.017 | 1.364 | 1.057 | 1.760 | 0.0025299 |
| COX2 cytoplasm:plasma membrane Ratio 0.01 | −1.515 | 0.634 | −2.388 | 0.017 | 0.220 | 0.063 | 0.762 | 0.0026297 |
| CD1a Cytoplasm mean intensity 0.05 | −0.148 | 0.056 | −2.652 | 0.008 | 0.862 | 0.773 | 0.962 | 0.0027675 |
| p53 nuclear membrane:AMACR nucleus Ratio 0.95 | 0.735 | 0.339 | 2.170 | 0.030 | 2.085 | 1.074 | 4.048 | 0.0029764 |
| p53 Cytoplasm mean intensity 0.99 | 0.009 | 0.004 | 2.135 | 0.033 | 1.009 | 1.001 | 1.018 | 0.0030656 |
| p16 Plasma membrane:nucleus Ratio 0.95 | −1.746 | 0.665 | −2.627 | 0.009 | 0.174 | 0.047 | 0.642 | 0.0032675 |
| p53 Cell mean intensity 0.99 | 0.011 | 0.005 | 2.149 | 0.032 | 1.011 | 1.001 | 1.020 | 0.0036121 |
| p16 Cell mean intensity 0.05 | −0.052 | 0.020 | −2.615 | 0.009 | 0.949 | 0.913 | 0.987 | 0.0038135 |
| COX2 Plasma membrane:nucleus Ratio 0.5 | 2.821 | 1.039 | 2.716 | 0.007 | 16.798 | 2.194 | 128.626 | 0.0038420 |
| COX2 cytoplasm:plasma membrane Ratio 0.5 | −0.067 | 0.025 | −2.690 | 0.007 | 0.935 | 0.891 | 0.982 | 0.0046218 |
| COX2 Plasma membrane: nucleus Ratio 0.95 | 1.000 | 0.379 | 2.637 | 0.008 | 2.718 | 1.293 | 5.714 | 0.0049389 |
| p16 Cell mean intensity 0.01 | −0.088 | 0.035 | −2.481 | 0.013 | 0.916 | 0.855 | 0.982 | 0.0053106 |
| p53 cytoplasm:AMACR membrane Ratio 0.99 | 0.016 | 0.007 | 2.255 | 0.024 | 1.016 | 1.002 | 1.031 | 0.0054591 |
| p16 Nuclei mean intensity 0.05 | −0.040 | 0.016 | −2.514 | 0.012 | 0.961 | 0.932 | 0.991 | 0.0058166 |
| CK20 cytoplasm:Ki67 nuclear membrane Ratio 0.99 | 0.006 | 0.002 | 2.575 | 0.010 | 1.006 | 1.001 | 1.010 | 0.0058939 |
| CD1a Cytoplasm mean intensity 0.01 | −0.150 | 0.059 | −2.565 | 0.010 | 0.861 | 0.767 | 0.965 | 0.0059660 |
| Ki67 Nuclei mean intensity 0.99 | 0.009 | 0.004 | 2.492 | 0.013 | 1.009 | 1.002 | 1.016 | 0.0068895 |
| COX2 cytoplasm:plasma membrane Ratio 0.05 | −0.568 | 0.273 | −2.081 | 0.037 | 0.567 | 0.332 | 0.968 | 0.0073582 |
| CK20 cytoplasm:Ki67 nuclear membrane 0.01 | −1.038 | 0.423 | −2.456 | 0.014 | 0.354 | 0.155 | 0.811 | 0.0079558 |
| CD1a Nuclei mean intensity 0.01 | −0.135 | 0.054 | −2.493 | 0.013 | 0.873 | 0.785 | 0.971 | 0.0080586 |
| CD68 cytoplasm:COX2 plasma membrane Ratio 0.01 | −0.911 | 0.453 | −2.008 | 0.045 | 0.402 | 0.165 | 0.979 | 0.0083563 |
| CK20 plasma membrane: Ki67 nucleus Ratio 0.99 | 0.089 | 0.037 | 2.419 | 0.016 | 1.093 | 1.017 | 1.174 | 0.0083992 |
| Ki67 nuclear membrane:nucleus Ratio 0.99 | −0.929 | 0.385 | −2.411 | 0.016 | 0.395 | 0.185 | 0.840 | 0.0086131 |
| p16 plasma membrane:p53 nucleus 0.95 | −0.361 | 0.157 | −2.300 | 0.021 | 0.697 | 0.513 | 0.948 | 0.0088832 |
| CD68 cytoplasm:COX2 plasma membrane Ratio 0.5 | −0.032 | 0.013 | −2.457 | 0.014 | 0.968 | 0.944 | 0.993 | 0.0092092 |
| NFKB cytoplasm:CD68 plasma membrane Ratio 0.01 | −0.672 | 0.282 | −2.381 | 0.017 | 0.511 | 0.294 | 0.888 | 0.0094753 |
| COX2 plasma membrane:NFKB nucleus 0.5 | 3.402 | 1.440 | 2.363 | 0.018 | 30.027 | 1.787 | 504.662 | 0.0097278 |

TABLE 5-continued

Univariate Ranking of P Values from Logistic Regression of No Progression Cases versus Progression to LGD and Progression to HGD/EAC Cases.

| Feature name (with percentile) | Estimate | Std. Error | z value | Pr(>\|z\|) (p value from linear regression (Wald test) | Effect | CI-lower (for effect) | CI-upper (for effect) | Pvalue_LR (deviance/ likelihood ratio p value) |
|---|---|---|---|---|---|---|---|---|
| p53 Nuclei mean intensity 0.95 | 0.011 | 0.006 | 1.720 | 0.085 | 1.011 | 0.998 | 1.024 | 0.0107267 |
| CD1a Nuclei mean intensity 0.5 | −0.046 | 0.021 | −2.228 | 0.026 | 0.955 | 0.917 | 0.994 | 0.0109146 |
| HIF1alpha cytoplasm: plasma membrane Ratio 0.05 | 0.181 | 0.085 | 2.125 | 0.034 | 1.199 | 1.014 | 1.417 | 0.0111103 |
| CK20 cytoplasm:Ki67 nuclear membrane Ratio 0.95 | 0.009 | 0.004 | 2.360 | 0.018 | 1.009 | 1.002 | 1.016 | 0.0112116 |
| CK20 plasma membrane: Ki67 nucleus Ratio 0.95 | 0.170 | 0.075 | 2.263 | 0.024 | 1.185 | 1.023 | 1.373 | 0.0125502 |
| HIF1alpha plasma membrane:CD1a nucleus Ratio 0.99 | 0.209 | 0.098 | 2.133 | 0.033 | 1.232 | 1.017 | 1.492 | 0.0146451 |
| p16 Nuclei mean intensity 0.5 | −0.017 | 0.008 | −2.231 | 0.026 | 0.983 | 0.968 | 0.998 | 0.0147046 |
| CD1a Cell mean intensity 0.5 | −0.047 | 0.022 | −2.129 | 0.033 | 0.954 | 0.914 | 0.996 | 0.0147551 |
| p16 Cell mean intensity 0.5 | −0.019 | 0.009 | −2.225 | 0.026 | 0.981 | 0.965 | 0.998 | 0.0148032 |
| AMACR membrane:nucleus Ratio 0.5 | −8.796 | 4.671 | −1.883 | 0.060 | 0.000 | 0.000 | 1.432 | 0.0149746 |
| NFKB cytoplasm:plasma membrane Ratio 0.5 | −0.131 | 0.095 | −1.375 | 0.169 | 0.877 | 0.727 | 1.057 | 0.0154471 |
| p53 cytoplasm:AMACR plasma membrane Ratio 0.95 | 0.026 | 0.013 | 1.986 | 0.047 | 1.026 | 1.000 | 1.052 | 0.0164280 |
| AMACR membrane:P16 nucleus Ratio 0.5 | −16.069 | 8.741 | −1.838 | 0.066 | 0.000 | 0.000 | 2.896 | 0.0174328 |
| CD68 cytoplasm:COX2 plasma membrane Ratio 0.05 | −0.286 | 0.157 | −1.822 | 0.068 | 0.752 | 0.553 | 1.022 | 0.0175976 |
| CD1a Nuclei mean intensity 0.95 | −0.023 | 0.012 | −2.038 | 0.042 | 0.977 | 0.955 | 0.999 | 0.0181563 |
| p53 Cell mean intensity 0.95 | 0.012 | 0.008 | 1.597 | 0.110 | 1.012 | 0.997 | 1.028 | 0.0187632 |
| CD45R0 cytoplasm:HIF1A plasma membrane Ratio 0.05 | 0.104 | 0.052 | 2.011 | 0.044 | 1.110 | 1.003 | 1.229 | 0.0223427 |
| p53 Cytoplasm mean intensity 0.95 | 0.011 | 0.007 | 1.437 | 0.151 | 1.011 | 0.996 | 1.025 | 0.0228740 |
| P16 Cytoplasm mean intensity 0.5 | −0.017 | 0.008 | −2.086 | 0.037 | 0.984 | 0.968 | 0.999 | 0.0231425 |
| NFKB cytoplasm: membrane Ratio 0.05 | −1.136 | 0.603 | −1.885 | 0.059 | 0.321 | 0.099 | 1.046 | 0.0236419 |
| AMACR Nuclei mean intensity 0.05 | −0.083 | 0.040 | −2.061 | 0.039 | 0.921 | 0.851 | 0.996 | 0.0255629 |
| CD1a Cytoplasm mean intensity 0.5 | −0.040 | 0.021 | −1.969 | 0.049 | 0.960 | 0.923 | 1.000 | 0.0257324 |
| CD68 cytoplasm:COX2 plasma membrane Ratio 0.95 | −0.027 | 0.013 | −2.083 | 0.037 | 0.973 | 0.949 | 0.998 | 0.0270777 |
| COX2 plasma membrane:nucleus Ratio 0.99 | 0.255 | 0.139 | 1.833 | 0.067 | 1.290 | 0.983 | 1.695 | 0.0282164 |
| Ki67 Cytoplasm:nuclear membrane Ratio 0.01 | −0.850 | 0.415 | −2.047 | 0.041 | 0.427 | 0.189 | 0.965 | 0.0290736 |
| AMACR Cytoplasm:membrane Ratio 0.01 | 0.502 | 0.262 | 1.921 | 0.055 | 1.653 | 0.990 | 2.760 | 0.0302793 |
| p16 cytoplasm:p53 nuclear membrane Ratio 0.01 | −0.224 | 0.134 | −1.676 | 0.094 | 0.799 | 0.615 | 1.039 | 0.0315419 |
| CD1a Nuclei mean intensity 0.99 | −0.015 | 0.008 | −1.889 | 0.059 | 0.985 | 0.969 | 1.001 | 0.0320830 |
| CD1a Cell mean intensity 0.95 | −0.020 | 0.011 | −1.844 | 0.065 | 0.980 | 0.960 | 1.001 | 0.0366663 |
| P16 plasma membrane:nucleus Ratio 0.5 | −5.337 | 3.154 | −1.692 | 0.091 | 0.005 | 0.000 | 2.325 | 0.0370970 |

TABLE 5-continued

Univariate Ranking of P Values from Logistic Regression of No Progression Cases versus Progression to LGD and Progression to HGD/EAC Cases.

| Feature name (with percentile) | Estimate | Std. Error | z value | Pr(>\|z\|) (p value from linear regression (Wald test) | Effect | CI-lower (for effect) | CI-upper (for effect) | Pvalue_LR (deviance/ likelihood ratio p value) |
|---|---|---|---|---|---|---|---|---|
| P16 plasma membrane:p53 nucleus Ratio 0.5 | −1.667 | 1.106 | −1.508 | 0.132 | 0.189 | 0.022 | 1.649 | 0.0372701 |
| HIF1alpha cytoplasm:CD1a plasma membrane Ratio 0.99 | 0.016 | 0.008 | 1.955 | 0.051 | 1.016 | 1.000 | 1.032 | 0.0389365 |
| AMACR Nuclei mean intensity 0.99 | −0.013 | 0.007 | −1.902 | 0.057 | 0.987 | 0.974 | 1.000 | 0.0397682 |
| HIF1alpha Nuclei mean intensity 0.5 | −0.024 | 0.013 | −1.948 | 0.051 | 0.976 | 0.952 | 1.000 | 0.0407365 |
| CD68 cytoplasm:plasma membrane Ratio 0.05 | −0.405 | 0.214 | −1.891 | 0.059 | 0.667 | 0.438 | 1.015 | 0.0409237 |
| NFKB membrane:CD68 nucleus ratio 0.5 | 0.690 | 0.354 | 1.950 | 0.051 | 1.994 | 0.997 | 3.989 | 0.0410493 |
| HIF1alpha cytoplasm:CD1a plasma membrane Ratio 0.01 | 0.130 | 0.067 | 1.921 | 0.055 | 1.138 | 0.997 | 1.299 | 0.0427105 |
| AMACR Nuclei mean intensity 0.5 | −0.033 | 0.018 | −1.853 | 0.064 | 0.967 | 0.934 | 1.002 | 0.0439938 |
| CD1a Cytoplasm:Plasma membrane Ratio 0.01 | 0.237 | 0.126 | 1.891 | 0.059 | 1.268 | 0.991 | 1.622 | 0.0452599 |
| NFKB cytoplasm:CD68 plasma membrane Ratio 0.05 | −0.189 | 0.103 | −1.828 | 0.067 | 0.828 | 0.676 | 1.014 | 0.0457721 |
| AMACR Cell mean intensity 0.05 | −0.082 | 0.045 | −1.842 | 0.065 | 0.921 | 0.844 | 1.005 | 0.0459226 |
| CD1a Cytoplasm mean intensity 0.95 | −0.019 | 0.010 | −1.769 | 0.077 | 0.982 | 0.962 | 1.002 | 0.0459685 |
| CD68 Cytoplasm:Plasma membrane Ratio 0.01 | −0.921 | 0.491 | −1.874 | 0.061 | 0.398 | 0.152 | 1.043 | 0.0459773 |
| CD68 Nuclei_mean intensity 0.99 | 0.010 | 0.007 | 1.594 | 0.111 | 1.010 | 0.998 | 1.024 | 0.0484793 |
| p16 plasma:p53 nucleus Ratio 0.99 | −0.128 | 0.068 | −1.872 | 0.061 | 0.880 | 0.770 | 1.006 | 0.0488473 |
| P16 Nuclei mean intensity 0.99 | −0.006 | 0.004 | −1.818 | 0.069 | 0.994 | 0.987 | 1.001 | 0.0495530 |
| AMACR Cell mean intensity 0.5 | −0.035 | 0.019 | −1.803 | 0.071 | 0.966 | 0.930 | 1.003 | 0.0498546 |
| NFKB cytoplasm: plasma membrane Ratio 0.01 | −1.498 | 0.847 | −1.767 | 0.077 | 0.224 | 0.042 | 1.177 | 0.0505213 |
| NFKB cytoplasm: plasma membrane Ratio 0.95 | −0.014 | 0.008 | −1.800 | 0.072 | 0.986 | 0.972 | 1.001 | 0.0535724 |
| CD1a Cell mean intensity 0.99 | −0.012 | 0.007 | −1.720 | 0.085 | 0.988 | 0.975 | 1.002 | 0.0540265 |
| Ki67 nuclear membrane:Nucleus Ratio 0.95 | −1.618 | 0.892 | −1.814 | 0.070 | 0.198 | 0.034 | 1.140 | 0.0543659 |
| beta-catenin plasma membrane:CK20 nucleus Ratio 0.95 | 0.249 | 0.138 | 1.803 | 0.071 | 1.283 | 0.979 | 1.681 | 0.0557799 |
| HIF1alpha Cell mean intensity 0.5 | −0.024 | 0.013 | −1.800 | 0.072 | 0.976 | 0.951 | 1.002 | 0.0587989 |

TABLE 6

Univariate Ranking of Features by P Values from Logistic Regression of Barrett's esophagus no dysplasia and Barrett's esophagus reactive atypia cases versus Barrett's esophagus low grade dysplasia and Barrett's esophagus high grade dysplasia cases.

| Feature | p value |
|---|---|
| Nuclei area | 0.000242 |
| Nuclei area | 0.000261 |
| Nuclei equivalent diameter | 0.000302 |
| Nuclei equivalent diameter | 0.000353 |
| Hoechst cell mean intensity | 0.000436 |
| Nuclei area | 0.000736 |
| HIF1 alpha cytoplasm; membrane ratio | 0.001293 |
| Hoechst cell mean intensity | 0.001588 |

TABLE 6-continued

Univariate Ranking of Features by P Values from Logistic Regression of Barrett's
esophagus no dysplasia and Barrett's esophagus reactive atypia cases versus Barrett's
esophagus low grade dysplasia and Barrett's esophagus high grade dysplasia cases.

| Feature | p value |
| --- | --- |
| Hoechst cell quantile intensity | 0.001975 |
| Hoechst nuclei mean intensity | 0.002379 |
| p53 cytoplasm:nuclear membrane intensity | 0.002448 |
| HIF1 alpha cytoplasm: CD45RO plasma membrane intensity | 0.002557 |
| Hoechst cell mean intensity | 0.002619 |
| Nuclei equivalent diameter | 0.002762 |
| Nuclei area | 0.003403 |
| p16 cytoplasm: plasma membrane ratio | 0.003594 |
| Hoechst cell quantile intensity | 0.003991 |
| Nuclei area | 0.00409 |
| Hoechst nuclei mean intensity | 0.004273 |
| AMACR cytoplasm: p53 nuclear membrane ratio | 0.004531 |
| Nuclei equivalent diameter | 0.004562 |
| Hoechst cell quantile intensity | 0.005236 |
| CD45RO cytoplasm:plasma membrane ratio | 0.005248 |
| CK-20 plasma membrane; CDX-2 nucleus ratio | 0.006393 |
| CDX-2 nuclear membrane: nucleus ratio | 0.006651 |
| Hoechst nuclei quantile intensity | 0.006928 |
| Hoechst nuclei quantile intensity | 0.008597 |
| Nuclei equivalent diameter | 0.0092 |
| Hoechst nuclei mean intensity | 0.009652 |
| AMACR cytoplasm mean intensity | 0.00988 |
| CDX-2 cytoplasm: HER2 plasma membrane ratio | 0.009952 |
| AMACR cell mean intensity | 0.01121 |
| CDX-2 cell mean intensity | 0.011466 |
| AMACR nuclear mean intensity | 0.013133 |
| Hoechst nuclei quantile intensity | 0.014573 |
| CDX-2 cytoplasm mean intensity | 0.016699 |
| HER2 plasma membrane: CK-20 nuclear ratio | 0.017772 |
| Nuclei solidity | 0.018268 |
| Nuclei solidity | 0.018759 |
| CD1a cytoplasm: plasma membrane ratio | 0.019828 |
| HER2 cytoplasm: CK-20 plasma membrane ratio | 0.020837 |
| HER2 cytoplasm: plasma membrane ratio | 0.021122 |
| p53 cell quantile intensity | 0.023041 |
| p53 nuclei quantile intensity | 0.023621 |
| HER2 nuclei mean intensity | 0.024433 |
| p16 cytoplasm: AMACR membrane ratio | 0.024943 |
| p53 cell mean intensity | 0.025204 |
| CDX-2 nuclear mean intensity | 0.025682 |
| HER2 cytoplasm mean intensity | 0.025711 |
| CD45RO cytoplasm: CD1a plasma membrane ratio | 0.026059 |
| CK-20 cytoplasm: plasma membrane ratio | 0.026579 |
| COX-2 cytoplasm: plasma membrane ratio | 0.027833 |
| CDX-2 cell quantile intensity | 0.028296 |
| p53 cytoplasm: p16 membrane ratio | 0.028584 |
| HER2 nuclei quantile intensity | 0.028831 |
| p53 nuclei mean intensity | 0.029849 |
| HER2 cell mean intensity | 0.030829 |
| p53 cytoplasm mean intensity | 0.031419 |
| CDX-2 nuclei quantile intensity | 0.032277 |
| AMACR nuclear quantile intensity | 0.034435 |
| HER2 cell quantile intensity | 0.040346 |
| p53 nuclear membrane: p16 nuclear ratio | 0.042366 |
| p16 plasma membrane nucleus intensity ratio | 0.043742 |
| NF-κB cytoplasm: COX-2 plasma membrane ratio | 0.044321 |
| NF-κB cytoplasm: COX-2 nucleus ratio | 0.045511 |
| AMACR cytoplasm: membrane ratio | 0.046059 |
| Hoechst cell mean intensity | 0.048906 |
| HIF1 alpha cell mean intensity | 0.050217 |
| HIF1 alpha cytoplasm mean intensity | 0.051545 |
| CD45RO cell mean intensity | 0.05373 |
| Nuclei eccentricity | 0.058986 |

TABLE 7

Significant Diagnostic and Prognostic Biomarker Features and Subcellular Localizations

| Biomarker | Significant Features | Subcellular Localizations | Tissue Localizations |
|---|---|---|---|
| Cytokeratin-20 (CK-20) | Mean intensity<br>Quantile intensity<br>Ratio CK-20: Ki-67<br>Ratio CK-20: beta-catenin<br>Ratio CK-20: CDX-2<br>Ratio CK-20: HER2<br>Ratio Cytoplasm: plasma membrane | Plasma membrane<br>Cytoplasm<br>Whole cell | Glands, surface epithelium, tumor |
| CDX-2 | Mean intensity<br>Quantile intensity<br>Ratio CDX-2: HER2<br>Ratio CDX-2: CK-20<br>Ratio Nuclear membrane: nucleus | Nucleus<br>Nuclear membrane<br>Whole cell | Glands, surface epithelium, tumor |
| p53 | Mean intensity<br>Quantile intensity<br>Ratio p53: AMACR<br>Ratio Cytoplasm: nuclear membrane | Nucleus<br>Nuclear membrane<br>Whole cell | Glands, surface epithelium, tumor |
| p16 | Mean intensity<br>Ratio Cytoplasm: membrane<br>Ratio P16: AMACR | Cytoplasm<br>Plasma membrane<br>Whole cell | Glands, surface epithelium, tumor, stroma |
| Ki-67 | Mean intensity<br>Ratio Ki-67: CK-20<br>Ratio Ki-67: Beta-catenin<br>Ratio nuclear membrane: total nucleus | Nucleus<br>Nuclear membrane<br>Whole cell | Glands, surface epithelium, tumor, stroma |
| Beta-catenin | Mean intensity<br>Ratio Beta-catenin: Ki-67<br>Ratio Beta-catenin: CK-20<br>Ratio plasma membrane: cytoplasm<br>Ratio cytoplasm: nucleus<br>Ratio plasma membrane: nucleus | Plasma membrane<br>Cytoplasm<br>Nucleus<br>Whole cell | Glands, surface epithelium, tumor |
| α-methylacyl coenzyme A racemase (AMACR) | Mean intensity<br>Quantile intensity<br>Ratio cytoplasm: membrane<br>Ratio membrane: nuclcus<br>Ratio AMACR: p53<br>Ratio AMACR: p16 | Cytoplasm<br>Mitochondria<br>Peroxisomes<br>Nucleus<br>Plasma membrane<br>Whole cell | Glands, surface epithelium, tumor, stroma |
| HER/neu | Mean intensity<br>Quantile intensity<br>Ratio cytoplasm: plasma membrane<br>Ratio HER2: CDX-2<br>Ratio HER2: CK-20 | Plasma membrane<br>Cytoplasm<br>Whole cell | Glands, surface epithelium, tumor |
| CD68 | Mean intensity<br>Ratio cytoplasm: plasma membrane<br>Ratio CD68: NF-kB<br>Ratio CD68: COX-2 | Plasma membrane<br>Cytoplasm<br>Nuclei<br>Whole cell | Stroma, glands, surface epithelium, tumor |
| CD45RO | Mean intensity<br>Ratio CD45RO: CD1a<br>Ratio CD45RO: HIF1 alpha<br>Ratio cytoplasm: plasma membrane | Plasma membrane<br>Cytoplasm<br>Whole cell | Stroma, glands, surface epithelium, tumor |
| CD1a | Mean intensity<br>Ratio cytoplasm: plasma membrane<br>Ratio CD1a: HIF-1alpha<br>Ratio CD1a: CD45RO | Plasma membrane<br>Cytoplasm<br>Whole cell | Stroma, glands, surface epithelium, tumor |

TABLE 7-continued

Significant Diagnostic and Prognostic Biomarker Features and Subcellular Localizations

| Biomarker | Significant Features | Subcellular Localizations | Tissue Localizations |
|---|---|---|---|
| HIF-1 alpha | Mean intensity<br>Ratio HIF1 alpha: CD1a<br>Ratio HIF1 alpha: CD45RO<br>Ratio cytoplasm: membrane | Nucleus<br>Cytoplasm<br>Plasma membrane<br>Whole cell | Stroma, glands, surface epithelium, tumor |
| Nuclear factor kappa B p65 (NF-κB) | Mean intensity<br>Ratio cytoplasm: plasma membrane<br>Ratio plasma membrane: nucleus<br>Ratio NF-kB: COX-2<br>Ratio NF: kB: CD68 | Cytoplasm<br>Nucleus<br>Plasma membrane<br>Whole cell | Stroma, glands, surface epithelium, tumor |
| Cyclooxygenase 2 (COX-2) | Mean intensity<br>Ratio plasma membrane: nucleus<br>Ratio cytoplasm: plasma membrane<br>Ratio COX-2: NF-kB<br>Ratio COX-2: CD68 | Plasma membrane<br>Nucleus<br>Cytoplasm<br>Whole cell | Stroma, glands, surface epithelium, tumor |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating Barrett's esophagus in a subject with low grade dysplasia, high grade dysplasia, or esophageal adenocarcinoma wherein the method comprises classifying an upper gastrointestinal sample of the subject as having low grade dysplasia, high grade dysplasia, or esophageal adenocarcinoma with a kit comprising:
   a) one or more probes, stains, or antibodies capable of labeling two or more biomarkers and nuclei; wherein the two or more biomarkers are selected from the group consisting of p53, HIF-1alpha, COX-2, and any combination thereof; and
   b) instructions for detecting the two or more biomarkers and nuclei with an optical scanner to generate a score for a medical professional to identify whether to treat the subject; wherein the subject having low grade dysplasia, high grade dysplasia, or esophageal adenocarcinoma is treated with a clinical treatment selected from endoscopic surveillance, endoscopic mucosal resection, radiofrequency ablation, and any combination thereof.

2. The method of claim 1, wherein the instructions comprise:
   a) generating digital image data from the two or more biomarkers and nuclei;
   b) analyzing the digital image data with a computer processor implementing computer-executable program code to produce pixel-based segmentation and object-based classification of subcellular compartments and tissues;
   c) quantifying one or more descriptive features of each biomarker and nuclei, wherein the one or more descriptive features are selected from the group consisting of mean intensity in a cell-based object including cell, cytoplasm, plasma membrane, and nucleus; and ratio of intensity between cell-based objects including cell, cytoplasm, plasma membrane, and nucleus; and
   d) converting the analyzed and quantified digital image data to generate the score by a predictive statistical model developed in a set that comprises disease cases and unaffected controls.

3. The method of claim 2, wherein the score is computed by linear combination of descriptive features weighted by coefficients obtained via linear regression model, and the score is correlated to a risk of progression to high grade dysplasia or esophageal adenocarcinoma.

4. The method of claim 1, wherein the two or more biomarkers further comprises beta-catenin, Ki-67, matrix metalloproteinase 1, CD68, CD45RO, Cytokeratin-20, CDx2, CD1a, p16, HER2/neu, Alpha-methylacyl-CoA racemase (AMACR), nuclear factor-kappa-B (NF-kB), CD4, forkhead box P3, thrombospondin-1, C-myc, fibroblast activation protein alpha, cyclin D1, EGFR, Interleukin-6, PLAU plasminogen activator urokinase (uPA), Fas, or FasL.

5. The method of claim 1, wherein each of the one or more probes, stains, or antibodies may be directly or indirectly conjugated to a fluorophore or histochemical stain or dye, and wherein each probe is detected with a different stain or dye.

6. The method of claim 1, wherein each of the one or more probes, stains, or antibodies comprises a fluorescent probe or comprises a fluorescent tag.

7. The method of claim 1, wherein each of the one or more probes, stains, or antibodies is labeled with a different fluorophore.

8. The method of claim 1, wherein the one or more probes, stains, or antibodies are antibodies that specifically bind to the two or more biomarkers.

9. The method of claim 2, wherein the one or more descriptive features further comprise a clinical factor selected from the group consisting of age, gender, Barrett's segment length as a continuous or categorical variable, Barrett's segment circumference and maximal extent, presence/absence of hiatal hernia, pathologic/histologic diagnosis, body mass index, smoking status, and any combination thereof.

* * * * *